United States Patent
Young et al.

(10) Patent No.: US 12,077,786 B2
(45) Date of Patent: Sep. 3, 2024

(54) METHODS OF CELL SELECTION AND MODIFYING CELL METABOLISM

(71) Applicant: LONZA LTD, Visp (CH)

(72) Inventors: Robert Young, Visp (CH); Christopher Mark Smales, Visp (CH); Colin Mark Jaques, Visp (CH); Andrew J. Racher, Visp (CH); Gurdeep Singh, Visp (CH); James Budge, Visp (CH); Joanne Robool, Visp (CH)

(73) Assignee: LONZA LTD, Visp (CH)

( * ) Notice: Subject to any disclaimer, the term of this patent is extended or adjusted under 35 U.S.C. 154(b) by 572 days.

(21) Appl. No.: 16/966,768

(22) PCT Filed: Feb. 1, 2019

(86) PCT No.: PCT/US2019/016403
§ 371 (c)(1),
(2) Date: Jul. 31, 2020

(87) PCT Pub. No.: WO2019/152876
PCT Pub. Date: Aug. 8, 2019

(65) Prior Publication Data
US 2023/0174971 A1 Jun. 8, 2023

Related U.S. Application Data

(60) Provisional application No. 62/625,773, filed on Feb. 2, 2018.

(51) Int. Cl.
*C12N 9/06* (2006.01)
*C12N 9/02* (2006.01)
(Continued)

(52) U.S. Cl.
CPC ....... *C12N 9/0008* (2013.01); *C12N 15/1075* (2013.01); *C12N 15/63* (2013.01)

(58) Field of Classification Search
CPC .................................................. C12N 9/0008
See application file for complete search history.

(56) References Cited

U.S. PATENT DOCUMENTS

| | | |
|---|---|---|
| 5,344,923 A | 9/1994 | Verma et al. |
| 5,633,162 A | 5/1997 | Keen et al. |

(Continued)

FOREIGN PATENT DOCUMENTS

| | | |
|---|---|---|
| CN | 102482337 A | 5/2012 |
| EP | 1239041 A2 | 9/2002 |

(Continued)

OTHER PUBLICATIONS

Smith. Biochemical and Biophysical Research Communications. vol. 99, No. 3, Apr. 15, 1981.*

(Continued)

*Primary Examiner* — Yong D Pak
(74) *Attorney, Agent, or Firm* — MEDLER FERRO WOODHOUSE & MILLS PLLC

(57) ABSTRACT

Described herein are compositions and methods for identifying, selecting, or culturing cells comprising a subject nucleic acid sequence of interest. Generally, a nucleic acid comprising a subject nucleic acid and a sequence encoding an enzyme molecule involved in biosynthesis of an amino acid is introduced into a cell. The cell is then grown on media lacking the amino acid, such that cells comprising the introduced nucleic acid are capable of growth. In some instances, the cell further comprises an inhibitor of the enzyme molecule to increase the stringency of the selection.

10 Claims, 34 Drawing Sheets

(51) Int. Cl.
  *C12N 15/10*  (2006.01)
  *C12N 15/63*  (2006.01)

(56) References Cited

U.S. PATENT DOCUMENTS

| | | |
|---|---|---|
| 5,656,491 A | 8/1997 | Cassani et al. |
| 6,326,193 B1 | 12/2001 | Liu et al. |
| 6,429,307 B1 | 8/2002 | Yoshiba |
| 6,703,199 B1 | 3/2004 | Koide |
| 7,629,167 B2 | 12/2009 | Hodge et al. |
| 8,298,054 B2 | 10/2012 | Hodge et al. |
| 2009/0305626 A1 | 12/2009 | Hope |
| 2011/0280797 A1 | 11/2011 | Mohtadi et al. |
| 2012/0077429 A1 | 3/2012 | Wernimont et al. |
| 2013/0280797 A1 | 10/2013 | Rao et al. |
| 2014/0073007 A1 | 3/2014 | Schüler et al. |
| 2016/0097074 A1 | 4/2016 | Collins et al. |
| 2016/0160236 A1 | 6/2016 | Famili et al. |

FOREIGN PATENT DOCUMENTS

| | | |
|---|---|---|
| EP | 0481791 B1 | 8/2003 |
| EP | 3741853 A1 | 11/2020 |
| JP | 5087194 | 9/2012 |
| WO | 2001/29058 A1 | 4/2001 |
| WO | 2001/96584 A2 | 12/2001 |
| WO | 2019152876 A2 | 8/2019 |

OTHER PUBLICATIONS

Budge, James D et al, Engineering of Chinese hamster ovary cell lipid metabolism results in an expanded ER and enhanced recombinant biotherapeutic protein production, Metabolic Engineering, Academic Press, US., 2019, vol. 57: 203-216.

Hollinger, Philipp; Hudson, Peter, Engineered antibody fragments and the rise of single domains, Nature Biotechnology, 2005, 23(9):11261136.

Leader, Benjamin et al., Protein therapeutics: a summary and pharmacological classification, Nature Reviews Drug Discovery, 2008, 7: 21-39.

Ayusawa et al., "Selection of mammalian thymidine auxotrophic cell mutants defective in thymidylate synthase by their reduced sensitivity to methotrexate," Somatic Cell Genetics 7(5):523-534 (1981).

Batzer et al., "Enhanced evolutionary PCR using oligonucleotides with inosine at the 3'-terminus," Nucleic Acids Research 19(18):5081 (1991).

Ham, "Clonal Growth of Mammalian Cells in a Chemically Defined, Synthetic Medium," PNAS 53:288-293 (1965).

Holowka et al., "Roles for Lipid Heterogeneity in Immunoreceptor Signaling," Biochim Biophys Acta. 1861(8 Pt B): 830-836 (2016).

Hu et al. "A bifunctional enzyme (Δ1-pyrroline-5-carboxylate synthetase) catalyzes the first two steps in proline biosynthesis in plants," PNAS 89:9354-9358 (1992).

Iscove et al. "Complete Replacement of Serum by Albumin, Transferrin, and Soybean Lipid in Cultures of Lipopolysaccharide-Reactive B Lymphocytes," J. Experimental Medicine 147:923-933 (1978).

Leibovitz, "The Growth and Maintenance of Tissue-Cell Cultures in Free Gas Exchange With the Atmosphere," Amer. J. Hygiene 78:173-180 (1963).

Lv et al., "Isolation and Molecular Identification of Auxotrophic Mutants to Develop a Genetic Manipulation System for the *Haloarchaeon natrinema* sp. J7-2," Archaea vol. 2015, Article ID 483194, 16 pages (2015).

Moore et al., "Culture of Normal Human Leukocytes," JAMA 199(8):519-524 (1967).

Ohtsuka et al., "An Alternative Approach to Deoxyoligonucleotides as Hybridization Probes by Insertion of Deoxyinosine at Ambiguous Codon Positions," J. Biol. Chem. 260(5):2605-2608 (1985).

Rodriguez et al., "Engineering *Escherichia coli* to overproduce aromatic amino acids and derived compounds," Microbial Cell Factories 13:126 (2014).

Roobol et al., "Ataxia-telangiectasia mutated and Rad3-related kinase (ATR) is activated by mild hypothermia in mammalian cells and subsequently activates p53," Biochemical Journal 435(2):499-508 (2011).

Rossolini et al., "Use of deoxyinosine-containing primers vs degenerate primers for polymerase chain reaction based on ambiguous sequence information" Molecular and Cellular Probes 8:91-98 (1994).

Zhang et al. "The increase of cell-membranous phosphatidylcholines containing polyunsaturated fatty acid residues induces phosphorylation of p53 through activation of ATR" J. Cell Sci. 120(Pt 23):4134-4143 (2007).

Zhang et al. "Dysregulation of the Low-Density Lipoprotein Receptor Pathway Is Involved in Lipid Disorder-Mediated Organ Injury," Int J Biol Sci. 12(5): 569-579 (2016).

International Search Report and Written Opinion in PCT/US2019/016403 issued Oct. 14, 2019.

* cited by examiner

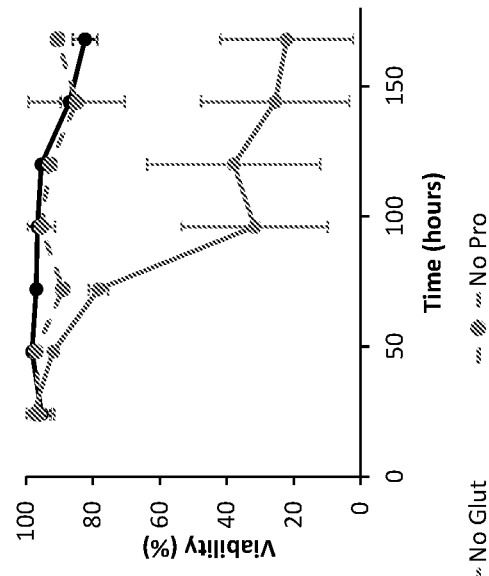
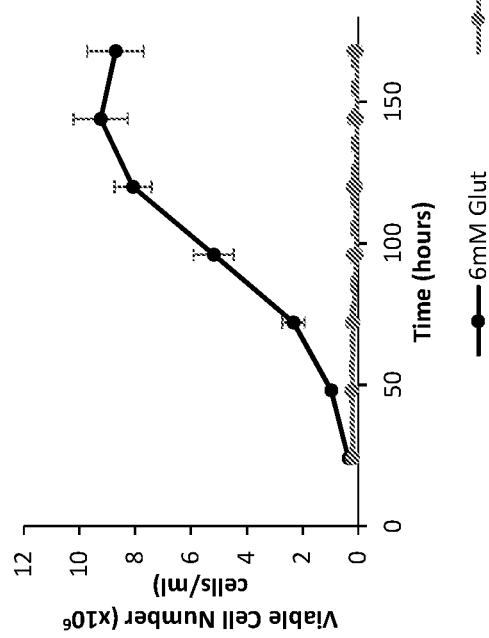
FIG. 3A
FIG. 3B

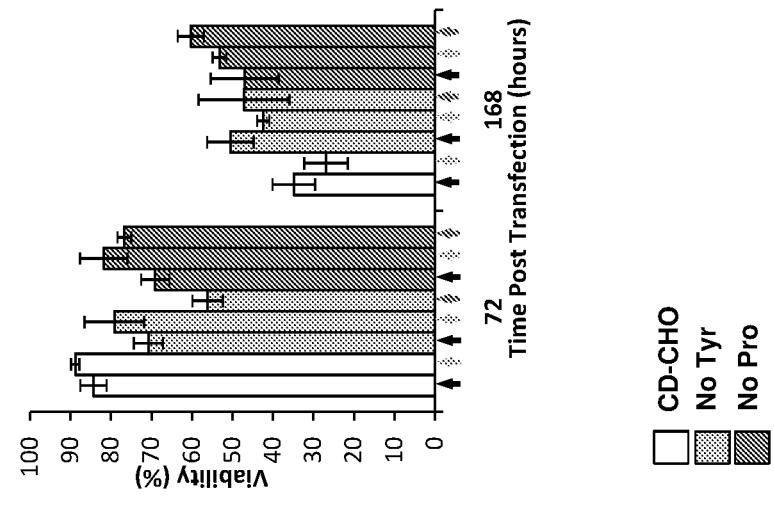
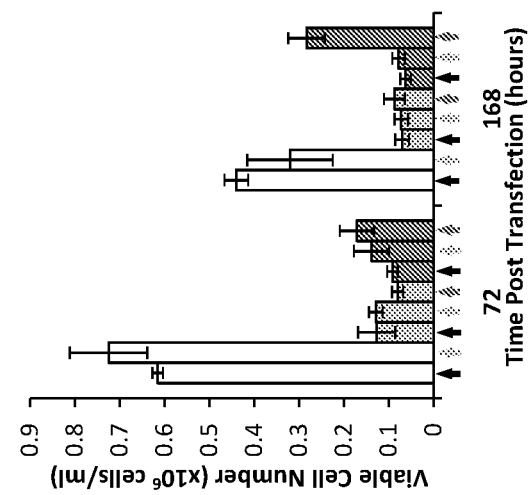
FIG. 5A
FIG. 5B
← = Control
▦ = eGFP/Glutamine Synthetase
▨ = eGFP/Pyrroline-5-Carboxylate Synthase
□ CD-CHO
▒ No Tyr
▨ No Pro

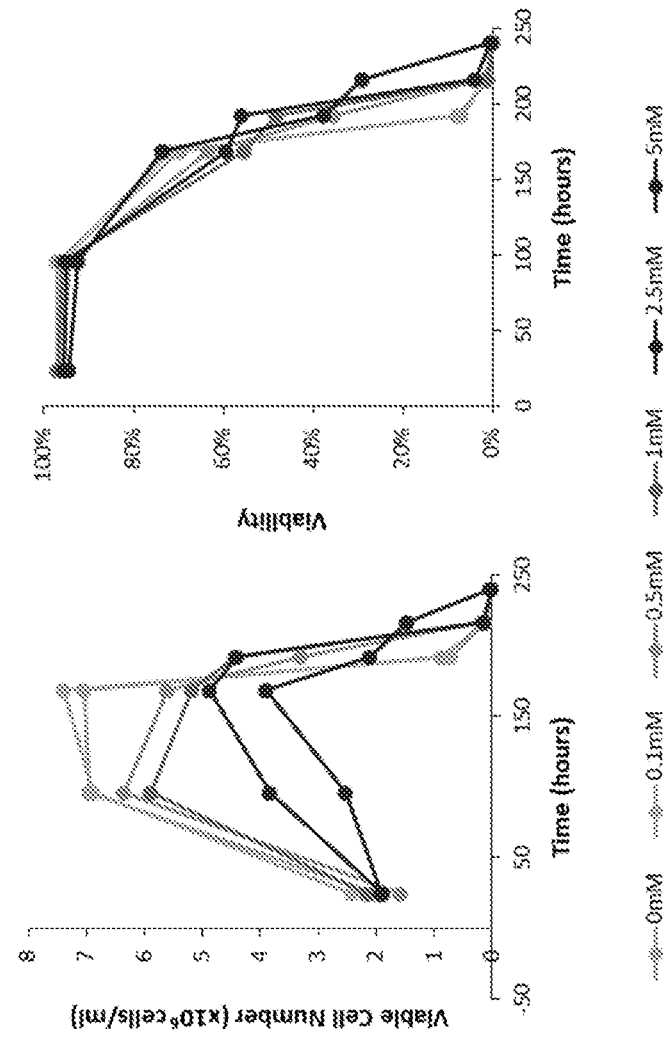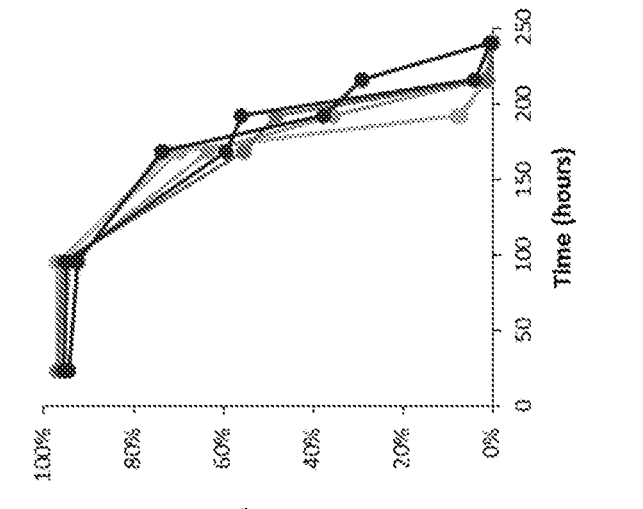

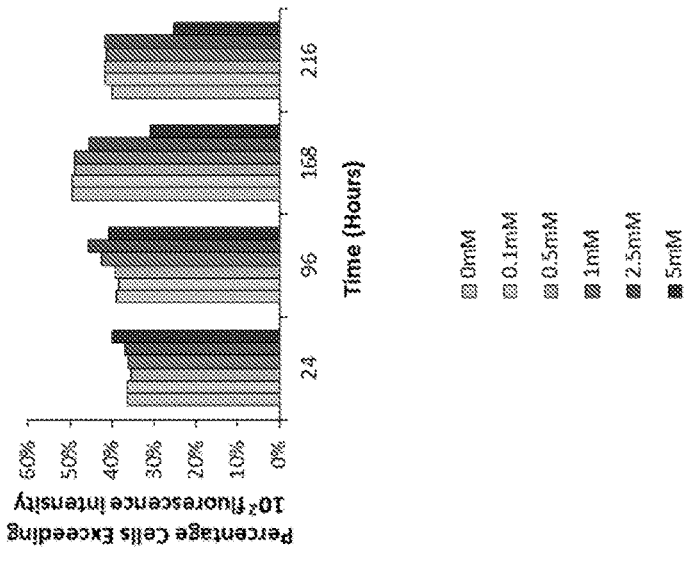
FIG. 9C
FIG. 9D
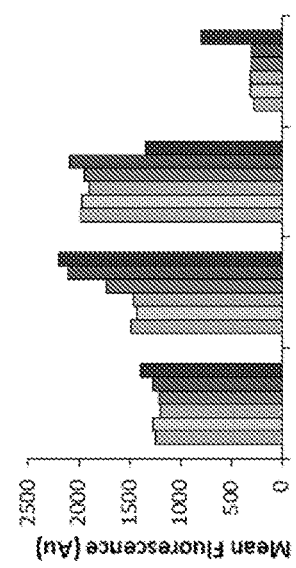
FIG. 9E
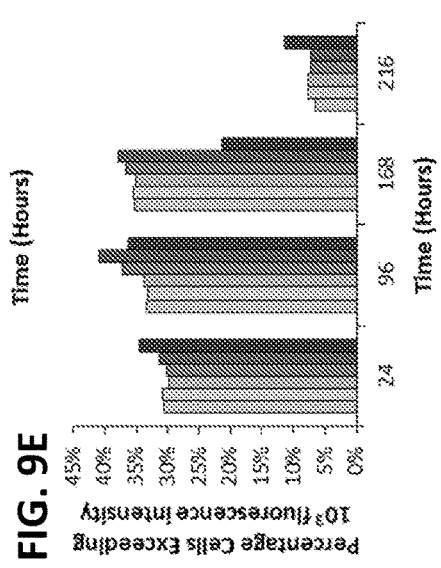
FIG. 9F

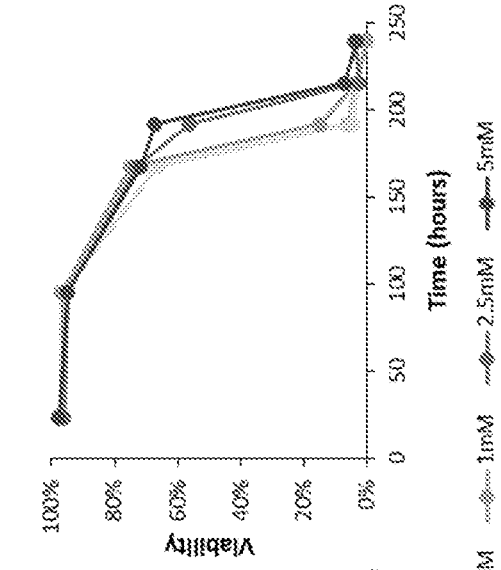
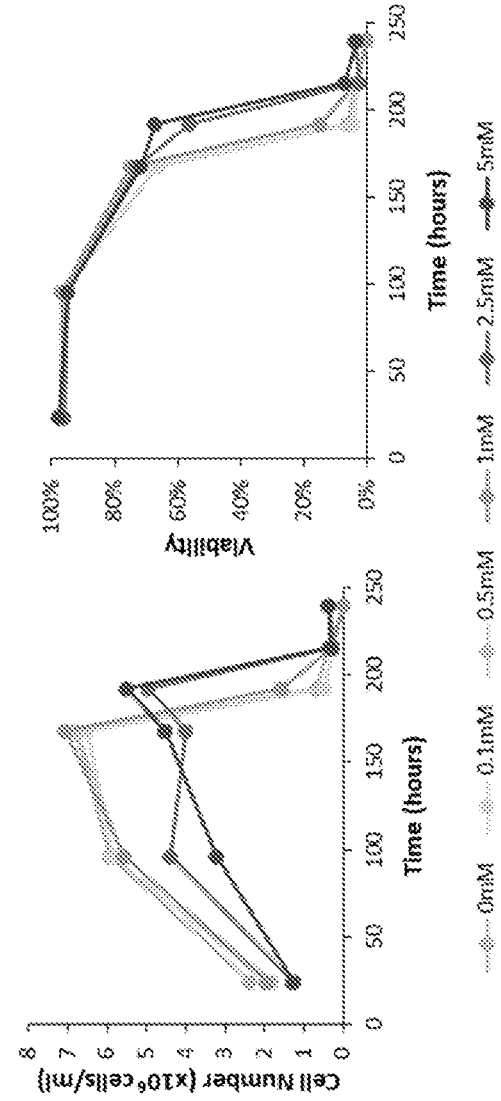
FIG. 10A
FIG. 10B

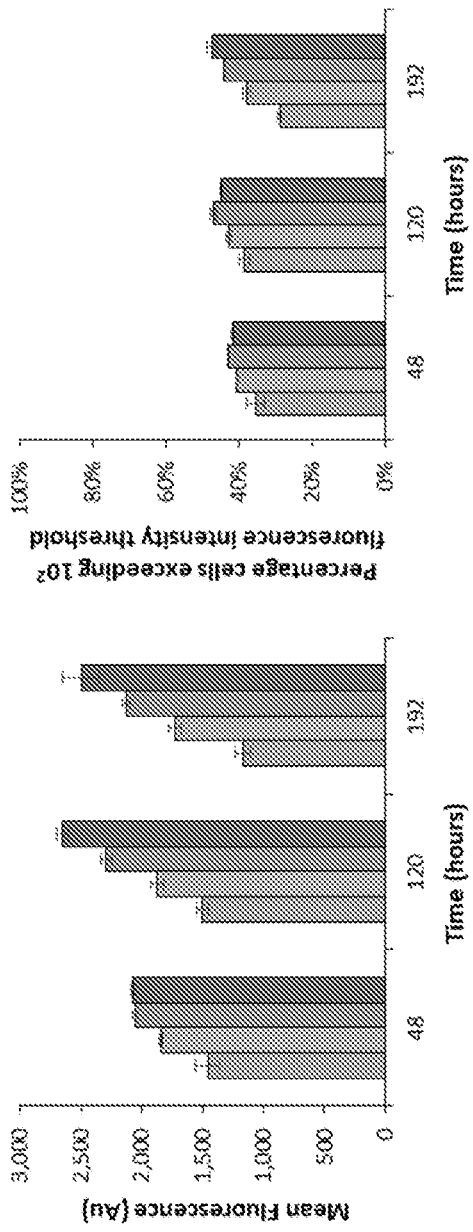
FIG. 11C
FIG. 11E
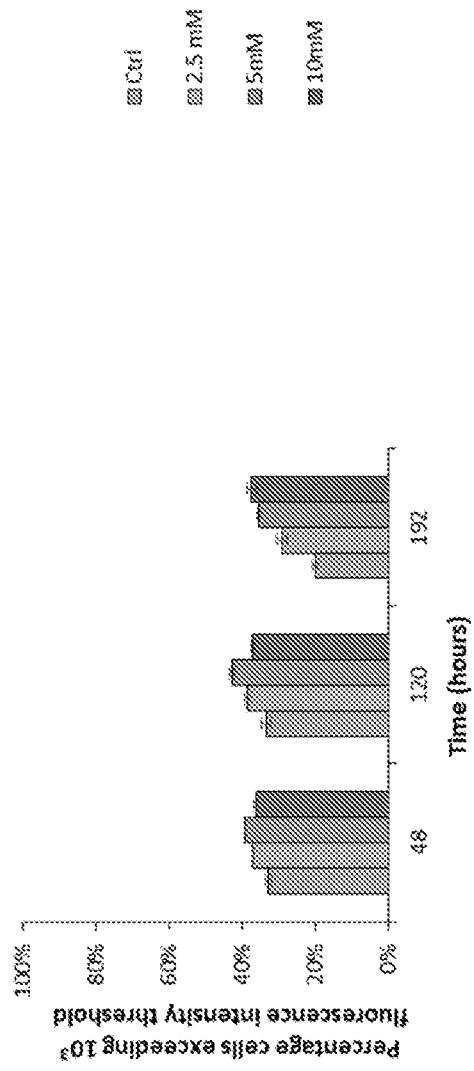
FIG. 11D

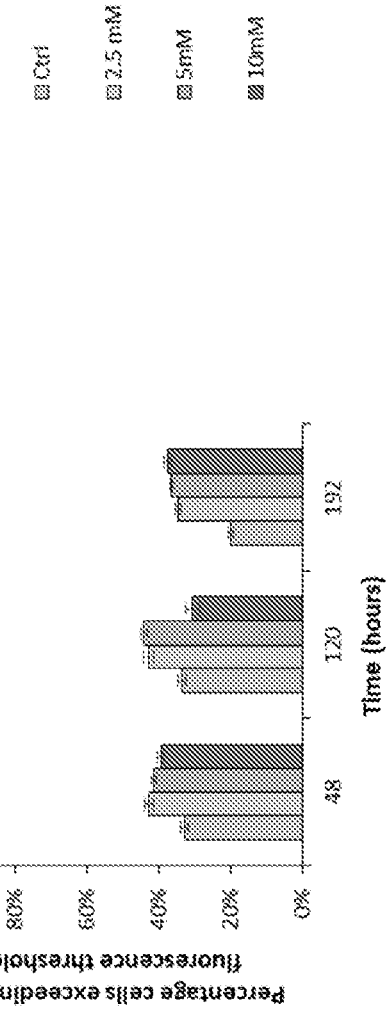
FIG. 12C
FIG. 12D
FIG. 12E

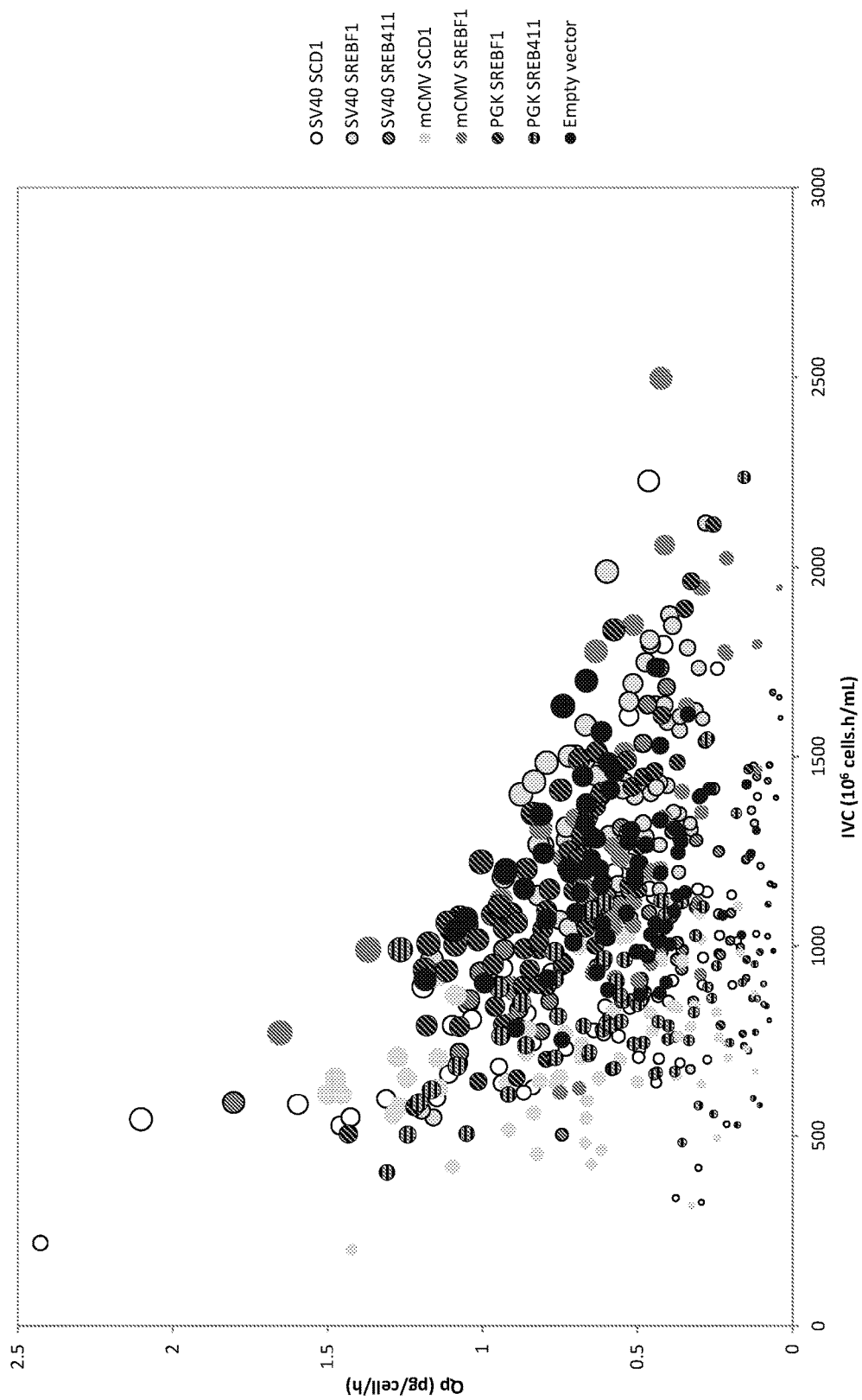

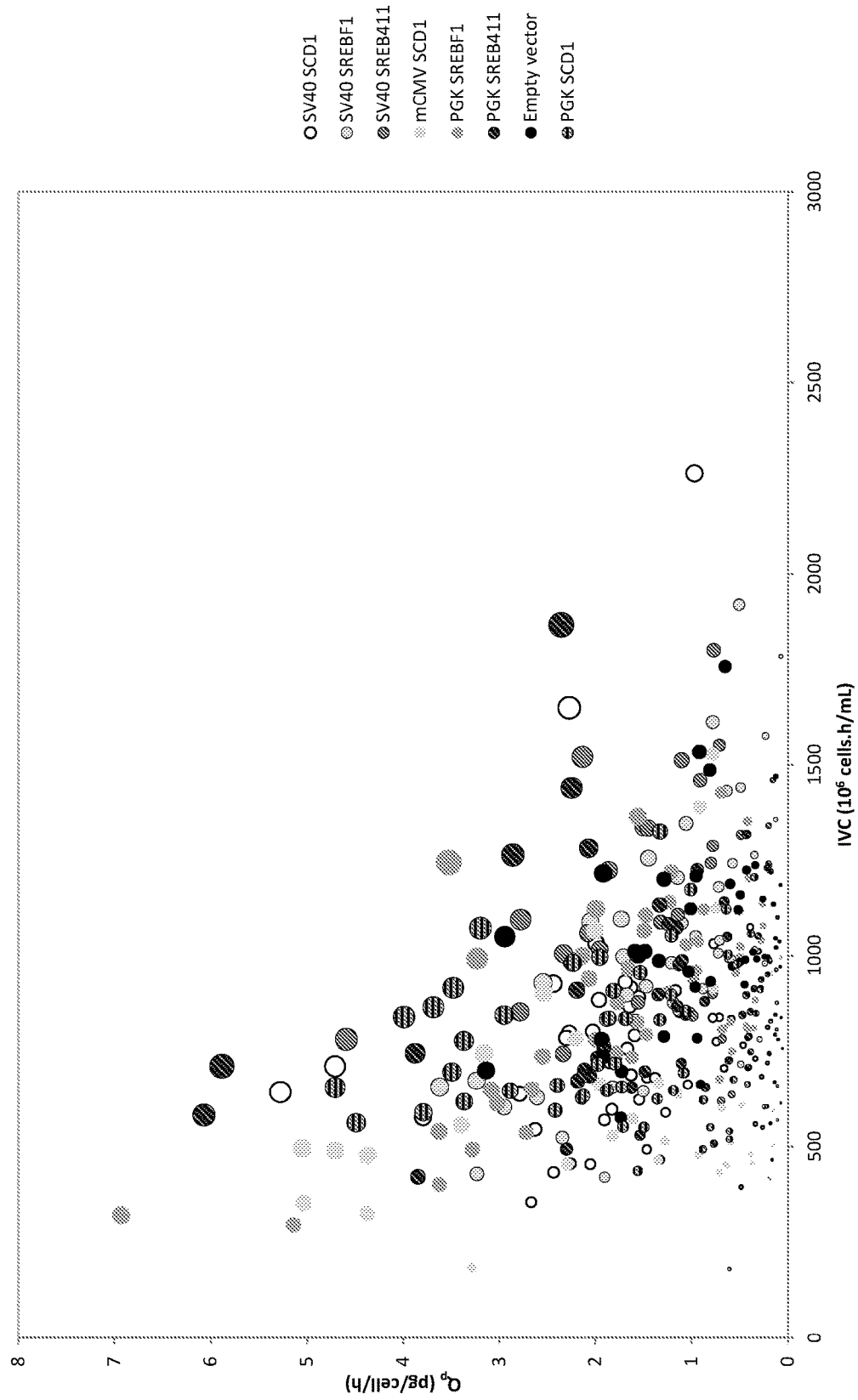

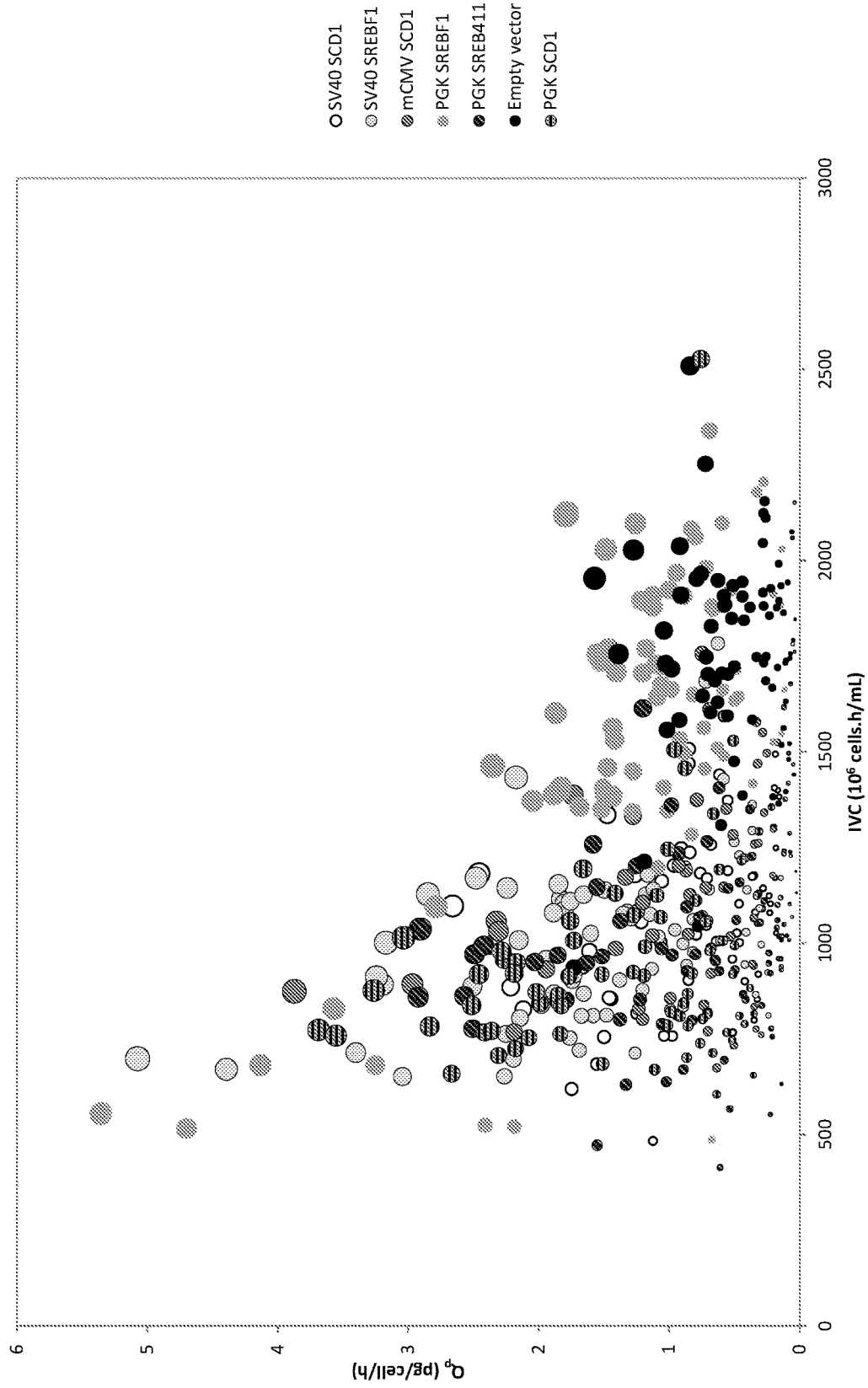

SV40- SREBF1 LMM pools

PGK-SREBF1 LMM pools

PGK- mSCD1 LMM pools

PGK-SCD1 LMM pools

METHODS OF CELL SELECTION AND MODIFYING CELL METABOLISM

CROSS-REFERENCE TO RELATED APPLICATIONS

The present application claims priority to and benefit from U.S. provisional application Ser. No. 62/625,773 (filed Feb. 2, 2018), the contents of which is hereby incorporated by reference in its entirety.

FIELD OF THE INVENTION

The present disclosure relates to methods and compositions for identifying, selecting, or culturing cells comprising a subject nucleic acid sequence.

BACKGROUND

Eukaryotic cells that are auxotrophic for an essential compound required for growth can be harnessed for expression of heterologous products by coupling expression of the product to that of an ectopic enzyme that enables synthesis of the essential compound. For example, mutant murine cells with an auxotrophy for thymidine cannot grow in the absence of externally supplied thymidine (Ayusawa et al. (1981) *Somatic Cell Genet.* 7(5): 523-534). Revertants in which thymidylate synthase activity was restored were able to grow under thymidine starvation conditions.

Mammalian cell expression systems are commonly used for the production of recombinant biological products, such as therapeutic biologics. However, large scale production of such products are associated with high initial costs due to the difficulty in efficiently generating stable cell lines that efficiently express large quantities of the desired product. Thus, there exists a need in the art for improved methods and compositions for the production of cells that can be used to produce recombinant biological products.

SUMMARY OF THE INVENTION

Described herein are compositions and methods for identifying, selecting, or culturing cells comprising a subject nucleic acid sequence of interest (e.g., one or more subject nucleic acid sequences of interest). Generally, a nucleic acid comprising a subject nucleic acid and a sequence encoding an enzyme molecule involved in biosynthesis of an amino acid is introduced into a cell. The cell is then grown on media lacking the amino acid, such that cells comprising the introduced nucleic acid are capable of growth. In some instances, the cell further comprises an inhibitor of the enzyme molecule to increase the stringency of the selection. It is contemplated that auxotrophies for compounds other than amino acids (e.g., trace metals, small molecules, nucleic acids, or other metabolites as known in the art) can be used in the selection methods described herein.

In an aspect, the invention features a method of identifying, selecting or culturing a cell comprising a subject nucleic acid sequence, the method comprising:
a) providing a cell comprising a nucleic acid, e.g., a vector, e.g., a replicable vector or integrating vector, comprising:
 (i) the subject nucleic acid sequence; and
 (ii) a nucleic acid sequence that when expressed results in an elevated level of activity of an enzyme in the synthetic pathway of an amino acid, e.g., the proline synthetic pathway, e.g., a nucleic acid sequence that encodes an enzyme molecule that comprises the activity; and
b) culturing the cell comprising the nucleic acid sequence in the presence of media having an insufficient level of the amino acid, e.g., proline, to support growth of a cell that is the same as the cell not having elevated activity, under conditions sufficient to allow for growth of a cell comprising the nucleic acid sequence,
thereby identifying, selecting or culturing, a cell comprising the heterologous nucleic acid sequence.

In an aspect, the invention features method of identifying, selecting or culturing, a cell comprising a subject nucleic acid sequence, the method comprising:
a) providing a cell comprising a nucleic acid, e.g., a vector, e.g., a replicable vector, comprising:
 (i) the subject nucleic acid sequence;
 (ii) a nucleic acid sequence that when expressed results in an elevated level of activity of an enzyme in the synthetic pathway of an amino acid, e.g., the proline synthetic pathway, e.g., a nucleic acid sequence that encodes an enzyme molecule that comprises the activity; and
b) culturing the cell comprising the nucleic acid sequence in the presence of the media having an insufficient level of the amino acid, e.g., proline, to support growth of a cell that is the same as the subject cell not having elevated activity, under conditions sufficient to allow for growth of a cell comprising the nucleic acid sequence (and the media optionally comprising an inhibitor of the enzyme),
c) culturing the cell comprising the nucleic acid sequence in the presence of the second media an insufficient level of the second amino acid, e.g., tyrosine, to support growth of a cell that is the same as the subject cell not having elevated activity, under conditions sufficient to allow for growth of a cell comprising the nucleic acid sequence (and the media optionally comprising an inhibitor of the second enzyme),
thereby identifying, selecting or culturing, a cell comprising the heterologous nucleic acid sequence.

In an aspect, the invention features a cell comprising a sequence encoding a heterologous lipid metabolism modifier (LMM) operatively linked to a sequence comprising a control region, e.g., a promoter sequence, from any of an SV40 promoter sequence, an mCMV promoter sequence, or a PGK promoter sequence.

BRIEF DESCRIPTION OF THE FIGURES

FIGS. 3A-3B are a series of graphs showing the growth profiles of GSKO cells cultured in different media—complete media (6 mM Glut), medium void of glutamine (No Glut) and medium void of proline (No Pro). FIG. 3A shows viable cell concentration, and FIG. 3B shows culture viability.

FIGS. 5A-5D are a series of graphs showing the effect of cell cultures transiently transfected with one of the exemplary vectors depicted in FIG. 4 and then cultured in CD-CHO (supplemented to contain 6 mM L-glutamine), tyrosine free (No Tyr), or proline free (No Pro) media. Shown are viable cell concentration (FIG. 5A), culture viability (FIG. 5B), mean eGFP fluorescence signal (FIG. 5C), and percentage of cells exceeding a predetermined eGFP fluorescence intensity threshold (FIG. 5D) at 72 hours and 168 hours post-transfection. Error bars represent standard deviation of the mean (n=3).

FIG. 6A shows a histogram obtained using flow cytometry analysis. FIGS. 6B and 6C each show fluorescent images generated via confocal microscopy; channels shown are DAPI, P5CS:TRITC, and eGFP. FIG. 6C shows a comparison between P5CS generated pools and the GSKO host.

FIGS. 8A-8F are a series of diagrams showing cell pools generated using P5CS overexpression and cultured in the absence of proline, and in the presence of L-azetidine-2-carboxylic acid, a P5CS inhibitor. L-azetidine-2-carboxylic acid was added at a variety of different concentrations and cells were cultured in 96 deep well plates for 9 days. These cells were analyzed for cell growth, as measured by viable cell concentration (FIG. 8A) and culture viability (FIG. 8B). Cells were also analyzed for mean culture fluorescence (FIG. 8C) and percentage of cells exceeding the predetermined thresholds of $10^2$ (FIG. 8D) and $10^3$ (FIG. 8E). FIG. 8F shows western blot analysis of lysates harvested at the specified time points and probed to highlight P5CS, β-actin and eGFP proteins.

FIGS. 9A-9F are a series of diagrams showing cell pools generated using P5CS overexpression and cultured in the absence of proline, and in the presence of 3,4-dehydro-L-proline, a P5CS inhibitor. 3,4-dehydro-L-proline was added at a variety of different concentrations and cells were cultured in 96 deep well plates for 9 days. These cells were analyzed for cell growth, as measured by viable cell concentration (FIG. 9A) and culture viability (FIG. 9B). Cells were also analyzed for mean culture fluorescence (FIG. 9C) and percentage of cells exceeding the predetermined thresholds of $10^2$ (FIG. 9D) and $10^3$ (FIG. 9E). FIG. 9F shows western blot analysis of lysates harvested at the specified time points and probed to highlight P5CS, β-actin and eGFP proteins.

FIGS. 10A-10F are a series of diagrams showing cell pools generated using P5CS overexpression and cultured in the absence of proline, and in the presence of L-4-thiazolidinecarboxylic acid, a P5CS inhibitor. L-4-thiazolidinecarboxylic acid was added at a variety of different concentrations and cells were cultured in 96 deep well plates for 9 days. These cells were analyzed for cell growth, as measured by viable cell concentration (FIG. 10A) and culture viability (FIG. 10B). Cells were also analyzed for mean culture fluorescence (FIG. 10C) and percentage of cells exceeding the predetermined thresholds of $10^2$ (FIG. 10D) and $10^3$ (FIG. 10E). FIG. 10F shows western blot analysis of lysates harvested at the specified time points and probed to highlight P5CS, β-actin and eGFP proteins.

FIGS. 11A-11E are a series of diagrams showing analysis of cell pools generated using P5CS overexpression and cultured in the absence of proline, and in the presence of L-azetidine-2-carboxylic acid, a P5CS inhibitor. L-azetidine-2-carboxylic acid was added at a variety of different concentrations and cells were cultured in static 24 well plates for 9 days. These cells were analyzed for cell growth, as measured by viable cell concentration (FIG. 11A) and culture viability (FIG. 11B). Cells were also analyzed for mean culture fluorescence (FIG. 11C) and percentage of cells exceeding the predetermined thresholds of $10^2$ (FIG. 11D) and $10^3$ (FIG. 11E).

FIGS. 12A-12E are a series of diagrams showing analysis of cell pools generated using P5CS overexpression and cultured in the absence of proline, and in the presence of 3,4-dehydro-L-proline, a P5CS inhibitor. 3,4-dehydro-L-proline was added at a variety of different concentrations and cells were cultured in static 24 well plates for 9 days. These cells were analyzed for cell growth, as measured by viable cell concentration (FIG. 12A) and culture viability (FIG. 12B). Cells were also analyzed for mean culture fluorescence (FIG. 12C) and percentage of cells exceeding the predetermined thresholds of $10^2$ (FIG. 12D) and $10^3$ (FIG. 12E).

FIGS. 16A-16D are a series of graphs showing bubble plots of specific productivity of cell cultures expressing an LMM gene and a gene of interest during aFOG. Cells were transfected with the indicated LMM gene under the control of the indicated promoter and a gene encoding Etanercept (FIG. 16A), Cergutuzumab (FIG. 16B), Infliximab (FIG. 16C), or cB72.3 (FIG. 16D). Cultures were grown in deep well plates, and VCC was measured via Celigo cell counting of each culture/well. Productivity was measured using an Octet instrument with protein A biosensors. Each data point shown corresponds to an individual culture; the diameter of each data point shows the product concentration achieved for that culture.

DETAILED DESCRIPTION OF THE INVENTION

Definitions

Figure 1:
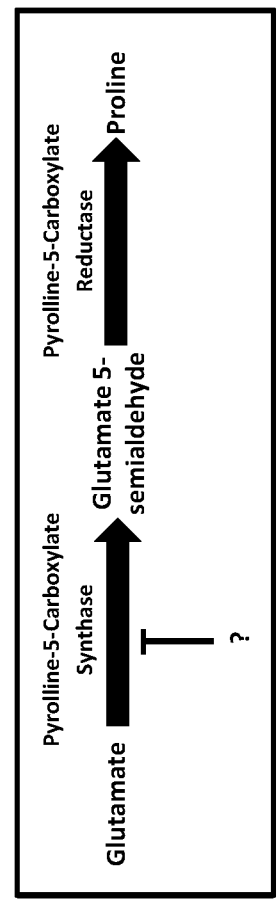
FIG. 1 is a schematic showing the rate limiting steps in mammalian proline synthesis pathway. The question mark refers to a possible inhibitor that could be used to inhibit the conversion of glutamate to glutamate 5-semialdehyde.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. In some embodiments, the article "a" or "an" refers to a single one of the grammatical object of the article. In some embodiments, the article "a" or "an" refers to a plurality (e.g., more than one, e.g., 2, 3, 4, 5, 6, 7, 8, 9, 10, 11, 12, 13, 14, 15, 16, 17, 18, 19, 20, 30, 40, 50, 60, 70, 80, 90, 100, or more) of the grammatical object of the article. By way of example, "a cell" can mean one cell or more than one (e.g., 2, 3, 4, 5, 6, 7, 8, 9, 10, 11, 12, 13, 14, 15, 16, 17, 18, 19, 20, 30, 40, 50, 60, 70, 80, 90, 100, or more) cell.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

As used herein, the term "plurality" refers to more than one (e.g., two or more) of the grammatical object of the article. By way of example, "a plurality of cells" can mean two cells or more than two cells.

As used herein, the term "endogenous" refers to any material from or naturally produced inside an organism, cell, tissue or system.

As used herein, the term "heterologous" refers to any material introduced into and/or produced outside of an organism, cell, tissue or system. Accordingly, "heterologous nucleic acid" refers to a nucleic acid that is introduced into and/or produced outside of an organism, cell, tissue or system. In some embodiments, sequences of the heterologous nucleic acid are not naturally produced, or cannot be naturally found, inside the organism, cell, tissue, or system into which the heterologous nucleic acid is introduced. In some embodiments, sequences of the heterologous nucleic acid can be naturally found inside the organism, cell, tissue, or system (e.g., a nucleic acid encoding an enzyme or LMM, e.g., as described herein, naturally found in a cell, wherein the nucleic acid is then expressed in the cell to produce additional copies of the enzyme or LMM). Similarly, "heterologous polypeptide" refers to a polypeptide that is introduced into and/or produced outside of an organism, cell, tissue or system. In some embodiments, the polypeptide is not naturally produced, or cannot be naturally found, inside the organism, cell, tissue, or system into which the heterologous polypeptide is introduced, e.g., by expression from an heterologous nucleic acid sequence. In some embodiments, the heterologous polypeptide can be naturally found inside the organism, cell, tissue, or system (e.g., an enzyme or LMM, e.g., as described herein, naturally found in a cell that is also ectopically expressed in the cell). In certain embodiments, a heterologous nucleic acid or polypeptide is introduced into an organism, cell, tissue, or system that comprises endogenous copies of the same polypeptide or nucleic acid, thereby increasing the quantity of the polypeptide or nucleic acid in the organism, cell, tissue, or system. In certain instances, the term "heterologous" can refer to any material from one species, when introduced to an organism, cell, tissue or system from a different species. In some instances, the terms "heterologous" and "exogenous" are used interchangeably.

As used herein, the term "enzyme molecule" refers to a polypeptide having an enzymatic activity of interest. An enzyme molecule may share structural similarity (e.g., sequence homology) with an enzyme having the enzymatic activity of interest. In some instances, the enzyme molecule has at least 50% amino acid sequence identity (e.g., at least about 50%, 60%, 70%, 75%, 80%, 85%, 90%, 91%, 92%, 93%, 94%, 95%, 96%, 97%, 98%, 99%, or 100% sequence identity) to an enzyme having the enzymatic activity of interest. In some instances, the term "molecule," when used with an identifier for an enzyme (e.g., pyrroline-5-carboxylate synthase (P5CS)), refers to a polypeptide having the enzymatic activity of the identified enzyme. By way of example, the term "P5CS molecule," as used herein, refers to a polypeptide having the enzymatic activity of P5CS. In some instances, the P5CS molecule has at least 50% amino acid sequence identity (e.g., at least about 50%, 60%, 70%, 75%, 80%, 85%, 90%, 91%, 92%, 93%, 94%, 95%, 96%, 97%, 98%, 99%, or 100% sequence identity) to a P5CS enzyme (e.g., a mammalian P5CS).

As used herein, the terms "nucleic acid," "polynucleotide," or "nucleic acid molecule" are used interchangeably and refers to deoxyribonucleic acid (DNA) or ribonucleic acid (RNA), or a combination of a DNA or RNA thereof, and polymers thereof in either single- or double-stranded form. The term "nucleic acid" includes, but is not limited to, a gene, cDNA, or an RNA sequence (e.g., an mRNA). In one embodiment, the nucleic acid molecule is synthetic (e.g., chemically synthesized or artificial) or recombinant. Unless specifically limited, the term encompasses molecules containing analogues or derivatives of natural nucleotides that have similar binding properties as the reference nucleic acid and are metabolized in a manner similar to naturally or non-naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). By "subject nucleic acid," as used herein, is meant any nucleic acid of interest, e.g., comprising a sequence encoding a product as described herein, that may be desirably introduced into or present within a cell as described herein.

As used herein, the terms "peptide," "polypeptide," and "protein" are used interchangeably, and refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

"Product" as that term is used herein refers to a molecule, e.g., polypeptide, e.g., protein, e.g., glycoprotein, nucleic acid, lipid, saccharide, polysaccharide, or any hybrid thereof, that is produced, e.g., expressed, by a cell, e.g., a cell which has been modified or engineered to produce the product. In an embodiment, the product is a protein or polypeptide product. In one embodiment, the product comprises a naturally occurring product. In an embodiment the product comprises a non-naturally occurring product. In one embodiment, a portion of the product is naturally occurring, while another portion of the product is non-naturally occurring. In one embodiment, the product is a polypeptide, e.g., a recombinant polypeptide. In one embodiment, the product is suitable for diagnostic or pre-clinical use. In another embodiment, the product is suitable for therapeutic use, e.g., for treatment of a disease. In some embodiments, a product is a protein product. In some embodiments, a product is a recombinant or therapeutic protein described herein, e.g., in Tables 5-8.

As used herein, the term "promoter" refers to a sequence having sufficient sequences, e.g., from a naturally occurring or engineered promoter such that operably linking a coding sequence to the promoter results in the expression of the coding sequence. For example, a cytomegalovirus (CMV) promoter comprises all or an active fragment of the CMV promoter, e.g., all or an active fragment of the CMV promoter including optionally intron A and/or UTR sequences. In an embodiment, a CMV promoter differs at no more than 5, 10, 20, 30, 50, or 100 nucleotides from a naturally occurring or engineered variant CMV promoter. In an embodiment, a CMV promoter differs at no more than 1, 5, 10, or 50% of its nucleotides from a naturally occurring or engineered variant CMV promoter. Promoters, as used herein, may be constitutive, regulated, repressible, strong, weak, or other properties of the promoter sequences the promoters comprise. In an embodiment, a promoter may comprise sequences 5' or 3' of a coding sequence, e.g., the coding sequence of a recombinant, therapeutic, or repressor polypeptide. In an embodiment, a promoter may comprise sequences within one or more introns of a gene, e.g., a gene encoding a recombinant, therapeutic, or repressor polypeptide. In an embodiment, a promoter may be comprised, in part or in its entirety, within sequences 5' or 3' of a coding sequence, e.g., the coding sequence of a recombinant, therapeutic, or repressor polypeptide. In an embodiment, a promoter may be comprised in part or in its entirety, within a coding sequence, e.g., the coding sequence of a recombinant, therapeutic, or repressor polypeptide. In an embodiment, a promoter may be comprised in part or in its entirety, within one or more introns of a gene, e.g., a gene encoding a recombinant, therapeutic, or repressor polypeptide.

As used herein, the term "operably linked" refers to a relationship between a nucleic acid sequence encoding a product (e.g., a polypeptide) and a control element, wherein the sequence encoding a polypeptide and the control element are operably linked if they are disposed in a manner suitable for the control element to regulate the expression of the sequence encoding a product (e.g., a polypeptide). Thus for different control elements, operably linked will constitute different dispositions of the sequence encoding a product (e.g., a polypeptide) relative to the control element. For example, a sequence encoding a product (e.g., a polypeptide) may be operably linked to a control element comprising a promoter element if the promoter element and sequence encoding a product (e.g., a polypeptide) are disposed proximal to one another and on the same nucleic acid. In another example, a sequence encoding a product (e.g., a polypeptide) may be operably linked to a control element comprising an enhancer sequence that operates distally if the enhancer sequence and sequence encoding a product (e.g., a polypeptide) are disposed a suitable number of bases apart on the same nucleic acid, or even on distinct and separate nucleic acids.

As used herein, the term "control element" refers to a nucleic acid suitable to regulate (e.g. increase or decrease) the expression of a coding sequence, e.g., a gene. Control elements may comprise promoter sequences, enhancer sequences, or both promoter and enhancer sequences. Control elements may comprise continuous nucleic acid sequences, discontinuous nucleic acid sequences (sequences interrupted by other coding or non-coding nucleic acid sequences), or both. A single control element may be comprised on a single nucleic acid or more than one nucleic acid.

In an embodiment, a control element may comprise sequences 5' or 3' of a coding sequence, e.g., the coding sequence of a recombinant, therapeutic, or repressor polypeptide. In an embodiment, a control element may comprise sequences within one or more introns of a gene, e.g., a gene encoding a recombinant, therapeutic, or repressor polypeptide. In an embodiment, a control element may be comprised, in part or in its entirety, within sequences 5' or 3' of a coding sequence, e.g., the coding sequence of a recombinant, therapeutic, or repressor polypeptide. In an embodiment, a control element may be comprised in part or in its entirety, within a coding sequence, e.g., the coding sequence of a recombinant, therapeutic, or repressor polypeptide. In an embodiment, a control element may be comprised in part or in its entirety, within one or more introns of a gene, e.g., a gene encoding a recombinant, therapeutic, or repressor polypeptide. In an embodiment, a single control element may comprise nucleic acid sequences i) proximal to (e.g., adjacent to or contained within) a gene, e.g., a gene encoding a recombinant, therapeutic, or repressor polypeptide, or ii) distal to (e.g., separated by 10 or more, 100 or more, 1000 or more, or 10,000 or more bases, or disposed on a distinct and separate nucleic acid) a gene, e.g., a gene encoding a recombinant, therapeutic, or repressor polypeptide.

"Lipid metabolism modifier" or "LMM", as used herein, refers to a molecule, gene product, polypeptide, or enzyme that modulates, e.g., increases or decreases, one or more of the following: the expression (e.g., transcription or translation) of a component involved in a lipid metabolism pathway; the activity (e.g., enzymatic activity) of a component, e.g., gene product, involved in a lipid metabolism pathway; the level or amount of lipids present in a cell; the level or amount of lipid rafts or rate of lipid raft formation; the fluidity, permeability, or thickness of a cell membrane, e.g., plasma membrane or an organelle membrane; the conversion of saturated lipids to unsaturated lipids or vice versa; the level or amount of saturated lipids or unsaturated lipids in a cell, e.g., monounsaturated lipids; lipid composition to achieve a favorable lipid composition that has a favorable impact on the activity of the ER; the expansion of the ER; the expansion of the Golgi; the level or amount of secretory vesicles or secretory vesicle formation; the level or rate of secretion; activation or inactivation of membrane receptors (e.g., ATR (see e.g., The increase of cell-membranous phosphatidylcholines containing polyunsaturated fatty acid residues induces phosphorylation of p53 through activation of ATR. Zhang X H, Zhao C, Ma Z A. J Cell Sci. 2007 Dec. 1; 120(Pt 23):4134-43 PMID: 18032786; ATR (ataxia telangiectasia mutated- and Rad3-related kinase) is activated by mild hypothermia in mammalian cells and subsequently activates p53. Roobol A, Roobol J, Carden M J, Bastide A, Willis A E, Dunn W B, Goodacre R, Smales C M. Biochem J. 2011 Apr. 15; 435(2):499-508. doi: 10.1042/BJ20101303. PMID: 21284603) and SREPB (see e.g., Int J Biol Sci. 2016 Mar. 21; 12(5):569-79. doi: 10.7150/ijbs.14027. eCollection 2016. Dysregulation of the Low-Density Lipoprotein Receptor Pathway Is Involved in Lipid Disorder-Mediated Organ Injury. Zhang Y, Ma K L, Ruan X Z, Liu B C); and additional receptors, see e.g., Biochim Biophys Acta. 2016 Mar. 17. pii: S1388-1981(16)30071-3. doi: 10.1016/j.bbalip.2016.03.019; and/or the unfolded protein response (UPR). In one embodiment, the LMM comprises a polypeptide. In one embodiment, the LMM comprises a transcriptional regulator, e.g., a transcription factor. In one embodiment, the LMM comprises SREBF1 or a functional fragment thereof (e.g., SREBF-410). In one embodiment, the LMM comprises an enzyme. In one embodiment, the LMM comprises SCD1 or a functional fragment thereof.

Methods of Identifying, Selecting, or Culturing Cells

In one aspect, the invention of the disclosure relates to a method of identifying, selecting, and/or culturing a cell. In some embodiments, the method includes:
  a) providing a cell comprising a nucleic acid, e.g., a vector, e.g., a replicable vector or integrating vector, comprising:
    (i) the subject nucleic acid sequence; and
    (ii) a nucleic acid sequence that when expressed results in an elevated level of activity of an enzyme in the synthetic pathway of an amino acid, e.g., a nucleic acid sequence that encodes an enzyme molecule that comprises the activity; and
  b) culturing the cell comprising the nucleic acid sequence in the presence of media having an insufficient level of the amino acid to support growth of a cell that is the same as the cell not having elevated activity, under conditions sufficient to allow for growth of a cell comprising the nucleic acid sequence,
    thereby identifying, selecting or culturing, a cell comprising the heterologous nucleic acid sequence.

In some embodiments, the enzyme molecule catalyzes the rate-limiting step of the biosynthesis pathway for the amino acid. In other embodiments, the enzyme molecule catalyzes a non-rate limiting step of the biosynthesis pathway for the amino acid. In embodiments, the amino acid is proline, tyrosine, or tryptophan.

In some embodiments, the cell further comprises an inhibitor of the activity of the enzyme molecule. The inhibitor can be used to increase the stringency of the selection process by reducing or preventing endogenous enzyme molecule activity, e.g., such that cells that do not take up the nucleic acid comprising the subject nucleic acid sequence exhibit reduced or undetectable levels of endogenous enzyme molecule activity. Cells exhibiting reduced or undetectable levels of endogenous enzyme molecule activity may not be able to grow and/or survive in the absence of an external supply of the amino acid for which synthesis requires the activity of the enzyme molecule (e.g., proline, tyrosine, or tryptophan). In some embodiments, the inhibitor binds to the enzyme molecule, e.g., it binds to and inhibits the enzyme molecule. In embodiments, the inhibitor is an allosteric inhibitor of the enzyme molecule. In embodiments, the inhibitor is a competitive inhibitor of the enzyme molecule. In some embodiments, the inhibitor inhibits transcription or translation of the enzyme molecule, e.g., endogenous transcription or translation of the enzyme molecule. In some embodiments, the inhibitor inhibits an enzyme molecule in the biosynthesis pathway for proline, tyrosine, or tryptophan. In embodiments, the inhibitor inhibits the activity of a pyrroline-5-carboxylate synthase (P5CS) molecule. In embodiments, the inhibitor inhibits the activity of P5CS. In embodiments, the inhibitor is a proline analog. In embodiments, the inhibitor is L-azetidine-2-carboxylic acid, 3,4-dehydro-L-proline, or L-4-thiazolidinecarboxylic acid.

In some embodiments, the method further includes one or more additional culture steps. In some embodiments, the one or more additional culture steps comprises culturing the cell in the presence of a second media (e.g., the same media composition as used in the first culturing step or a different media than that used in the first culturing step). In embodiments, the first culturing step utilizes a media comprising an insufficient level of, e.g., lacking, a first amino acid (e.g., proline) and the second culturing step utilizes a media comprising an insufficient level of, e.g., lacking, a second amino acid (e.g., tyrosine or tryptophan). In embodiments, the cell comprises an enzyme molecule that rescues production of the first amino acid and/or an enzyme molecule that rescues production of the second amino acid only if the cell further comprises a subject nucleic acid of interest. It is contemplated that this approach can be extended to additional culture steps, each involving a media comprising an insufficient level of, e.g., lacking, an amino acid (e.g., the same or a different amino acid from those missing from the first or second culture media) and the cell comprising an enzyme molecule capable of rescuing production of the amino acid (e.g., the same or a different amino acid from those missing from the first or second culture media). In embodiments, the media used in an additional culture step comprises an inhibitor of the amino acid missing from the culture used in the additional culture step. In some embodiments, the culture steps can be performed concurrently, e.g., using a media comprising an insufficient level of, e.g., lacking a plurality of amino acids. In some embodiments, only a subset of the culture steps comprises using an inhibitor of the enzyme molecule. For example, the first culture step may comprise using an inhibitor of the enzyme molecule, followed by culture steps that do not comprise using the inhibitor of the enzyme molecule.

In some embodiments, the method can be used to generate a cell comprising a heterologous nucleic acid, e.g., a cell useful for producing a product, e.g., a polypeptide product, e.g., an antibody.

Enzyme Molecules and Inhibitors Thereof

The invention generally features methods and compositions for selecting cells into which a nucleic acid is introduced by selecting for expression of an enzyme molecule involved in biosynthesis of an amino acid. The enzyme molecule may be introduced into the cell alongside the subject nucleic acid. For example, a nucleic acid may be introduced into the cell that comprises both the subject nucleic acid and a gene encoding the enzyme molecule, such that the enzyme molecule is expressed in the cell. In some embodiments, cells comprising the subject nucleic acid exhibit elevated enzyme molecule activity compared to cells lacking the subject nucleic acid. In some embodiments, the level of enzyme molecule activity is increased by at least 10%, 20%, 30%, 40%, 50%, 60%, 70%, 80%, 90%, 100%, 200%, 500%, 1000%, or more relative to enzyme molecule activity detectable in cells lacking the subject nucleic acid. In some embodiments, cells with the elevated activity may grow more quickly than cells lacking the subject nucleic acid. In some embodiments, the cell comprises at least 1, 2, 3, 4, 5, 6, 7, 8, 9, 10, 20, 30, 40, 50, 60, 70, 80, 90, 100, 200, 500, 1000, 5000, 10,000 or more copies of a nucleic acid encoding the enzyme. In embodiments, cells with the elevated activity grow at least about 1.5, 2, 3, 4, 5, 6, 7, 8, 9, 10, 20, 30, 40, 50, 60, 70, 80, 90, 100, 150, 200, 250, 300, 400, 500, 600, 700, 800, 900, 1000, 1500, 2000, 5000, or 10,000 times more quickly on media lacking the amino acid than cells lacking the subject nucleic acid. Cells can then be grown on media lacking the amino acid to select for cells that have taken up the subject nucleic acid. In some embodiments, the selection comprises selecting one or more cells that exhibit growth on media lacking the amino acid.

Enzyme Molecule Inhibitors

The cells described herein may, in some embodiments, further comprise an inhibitor of an enzyme molecule that is being expressed by a nucleic acid introduced into the cell (e.g., the subject nucleic acid or a second nucleic acid). The inhibitor can, for example, serve to reduce or block activity of the enzyme molecule endogenously produced by the cell, and/or to reduce or block growth of revertant cells, thereby acting to increase the stringency of, e.g., the selection methods described herein. In some embodiments, the level of inhibitor in the cell is sufficient to reduce endogenous enzyme molecule activity to less than about 0.001%, 0.01%, 0.1%, 1%, 2%, 3%, 4%, 5%, 10%, 20%, 25%, 30%, 40%, or 50% of that observed in a cell lacking the inhibitor. In some embodiments, less than about 0.001%, 0.01%, 0.1%, 1%, 5%, or 10% of cells selected on the basis of growth in media lacking the amino acid do not comprise the subject nucleic acid. In some embodiments, the ratio of enzyme molecules and inhibitor molecules in the cell is about 1:1000, 1:500, 1:250, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, 20:1, 30:1, 40:1, 50:1, 60:1, 70:1, 80:1, 90:1, 100:1, 200:1, 250:1, 500:1, or 1000:1.

The inhibitor can be, for example, an amino acid or analog thereof, a polypeptide, a nucleic acid, or a small molecule. In some embodiments, the inhibitor is an analog of the amino acid produced by the biosynthetic pathway in which the enzyme molecule participates. In some embodiments, the inhibitor is an antibody molecule (e.g., an antibody or an antibody fragment, e.g., as described herein), a fusion protein, a hormone, a cytokine, a growth factor, an enzyme, a glycoprotein, a lipoprotein, a reporter protein, a therapeutic peptide, an aptamer, or a structural and/or functional fragment or hybrid of any of these. In some embodiments, the inhibitor is an antisense RNA, siRNA, tRNA, ribosomal RNA, microRNA, piRNA, snoRNA, snRNA, exRNA, scaRNA, or long noncoding RNA.

Non-limiting examples of enzyme molecules and inhibitors thereof that may be used in the compositions and methods described herein include those listed in Table 1.

TABLE 1

Exemplary enzyme molecules involved in amino acid biosynthesis and exemplary inhibitors thereof

| Amino Acid | Enzyme Molecule | Inhibitors |
| --- | --- | --- |
| Alanine | Glutamate dehydrogenase | |
| | Aminotransferase | |
| Leucine | Acetolactate synthase | |
| | Acetohydroxy acid isomeroreductase | |
| | Dihydroxyacid dehydratase | |
| | α-Isopropylmalate synthase | |
| | α-Isopropylmalate isomerase | |
| | Leucine aminotransferase | |
| Isoleucine | Acetolactate synthase | |
| | Acetohydroxy acid isomeroreductase | |

TABLE 1-continued

Exemplary enzyme molecules involved in amino acid biosynthesis and exemplary inhibitors thereof

| Amino Acid | Enzyme Molecule | Inhibitors |
|---|---|---|
| Methionine | Dihydroxyacid dehydratase<br>Valine aminotransferase<br>Cys/Met metabolism PLP-dependent enzyme<br>Cystathionine-γ-synthase | β-Cyanoalanine (e.g., at 14 ± 0.2 μM)<br>Propargylglycine (e.g., at 40 ± 8 μM)<br>aminooxyacetic acid (e.g., at 1.1 ± 0.1 μM)<br>L-aminoethoxyvinylglycine |
|  | Cystathionine-β-lyase<br>O-acetylhomoserine aminocarboxypropyltransferase<br>Methionine synthase (e.g., 5-methyltetrahydrofolate-homocysteine methyltransferase)<br>Aspartokinase<br>Aspartate-semialdehyde dehydrogenase<br>Homoserine dehydrogenase<br>Homoserine O-transsuccinylase |  |
| Valine | Acetolactate synthase<br>Acetohydroxy acid isomeroreductase<br>Dihydroxyacid dehydratase<br>Valine aminotransferase |  |
| Phenylalanine | Chorismate mutase<br>Prephenate dehydratase<br>Aromatic aminotransferase I<br>Aromatic aminotransferase II<br>Pretyrosine dehydratase |  |
| Tryptophan | Anthranilate synthase<br>Anthranilate PR transferase<br>Phosphoribosyl anthranilate isomerase<br>IGP synthase<br>3-phospho-glyceraldyhyde |  |
| Tyrosine | Phenylalanine hydroxylase<br>Chorismate mutase<br>Prephenate aminotransferase<br>Pretyrosine dehydrogenase |  |
| Asparagine | Transaminase<br>Asparagine synthetase |  |
| Cysteine | Cystathionine beta synthase<br>Cystathionine gamma lyase<br>Serine transacetylase<br>O-acetylserine (thiol)-lyase |  |
| Glutamine | Glutamine synthetase |  |
| Serine | Phosphoglycerate dehydrogenase | O-acetyl-L-serine (e.g., at 1.4 mM)<br>L-Allothreonine (e.g., at 1.5 mM)<br>Glycine (e.g., at 1.8 mM)<br>L-Alanine (e.g., at 3.0 mM)<br>L-Serinamide (e.g., at 3.8 mM)<br>L-Cysteine (e.g., at 4.1 mM)<br>L-Homoserine (e.g., at 5.1 mM)<br>N-Cbz-L-serine (e.g., at 15.0 mM)<br>L-or-Aminobutyrate (e.g., at 18.5 mM)<br>L-Threonine (e.g., at 27.0 mM)<br>N-or-benzyl-L-serine (e.g., at 50.0 mM) |
|  | Phosphoserine transaminase<br>Phosphoserine phosphatase<br>Serine hydroxymethyltransferase |  |
| Threonine | Aspartokinase<br>β-aspartate semialdehyde dehydrogenase<br>Homoserine dehydrogenase<br>Homoserine kinase<br>Threonine synthase |  |
| Aspartic acid | Pyruvate carboxylase<br>Mitochondrial aspartate aminotransferase<br>Cytosolic aspartate aminotransferase |  |

TABLE 1-continued

Exemplary enzyme molecules involved in amino acid biosynthesis and exemplary inhibitors thereof

| Amino Acid | Enzyme Molecule | Inhibitors |
|---|---|---|
| Glutamic acid | Glutaminase | |
| | N-acetyl-glutamate synthase | |
| | Glutamate dehydrogenase | |
| | Aldehyde dehydrogenase ALDH4A1 | |
| | Formimidoyltransferase cyclodeaminase | |
| | Glutamate carboxypeptidase II | |
| Arginine | Argininosuccinate synthetase | |
| | Argininosuccinate lyase | |
| | Ornithine carbamoyltransferase | |
| | Mitochondrial ornithine acetyltransferase | |
| | Acetylornithine aminotransferase | |
| | Acetylglutamate kinase | |
| | N-acetyl-gamma-glutamyl-phosphate reductase | |
| | Acetylglutamate synthase | |
| Histidine | ATP phosphoribosyltransferase | |
| | Trifunctional histidinol dehydrogenase/phosphoribosyl-AMP cyclohydrolase/phosphoribosyl-ATP diphosphatase | |
| | 1-(5-phosphoribosyl)-5-((5-phosphoribosylamino)methyl-ideneamino)imidazole-4-carboxamide isomerase | |
| | Imidazole glycerol phosphate synthase | |
| | Histidinol-phosphate aminotransferase | |
| | Histidinolphosphatase | |
| Lysine | Aspartokinase | |
| | β-Aspartate semialdehyde dehydrogenase | |
| | 4-hydroxy-tetrahydrodipicolinate synthase | |
| | 4-hydroxy-tetrahydrodipicolinate reductase | |
| | Tetrahydrodipicolinate N-acetyltransferase | |
| | Succinyl diaminopimelate aminotransferase | |
| | Succinyl diaminopimelate desuccinylase | |
| | Diaminopimelate epimerase | |
| | Diaminopimelate decarboxylase | |
| Glycine | Serine hydroxymethyltransferase | |
| | Glycine synthase | |
| Proline | Pyrroline-5-carboxylate synthase (P5CS) | Proline |
| | | Proline analogs (e.g., L-azetidine-2-carboxylic acid, 3,4-Dehydro-L-Proline, or L-4-Thiazolidinecarboxylic acid) |
| | Glutamate 5-kinase | |
| | Pyrroline-5-carboxylate reductase | |

In some embodiments, the inhibitor inhibits an enzyme molecule in the biosynthesis pathway for an amino acid, e.g., proline, tyrosine, or tryptophan. In embodiments, the inhibitor inhibits an enzyme molecule catalyzing the rate-limiting step in the biosynthesis pathway for the amino acid.

In some embodiments, the inhibitor inhibits an enzyme molecule in the proline biosynthesis pathway, e.g., an enzyme molecule catalyzing the rate-limiting step in the proline biosynthesis pathway. In embodiments, the inhibitor inhibits the activity of a pyrroline-5-carboxylate synthase (P5CS) molecule. In embodiments, the inhibitor inhibits the activity of P5CS. In embodiments, the inhibitor is proline or a proline analog. In embodiments, the inhibitor is L-azetidine-2-carboxylic acid, 3,4-Dehydro-L-Proline, or L-4-Thiazolidinecarboxylic acid.

In some embodiments, the inhibitor inhibits an enzyme molecule in the tyrosine biosynthesis pathway, e.g., an enzyme molecule catalyzing the rate-limiting step in the tyrosine biosynthesis pathway. In embodiments, the inhibitor is a tyrosine analog.

In some embodiments, the inhibitor inhibits an enzyme molecule in the tryptophan biosynthesis pathway, e.g., an enzyme molecule catalyzing the rate-limiting step in the tryptophan biosynthesis pathway. In embodiments, the inhibitor is a tryptophan analog.

Lipid Metabolism Modifiers

The present disclosure features methods and compositions for producing cells comprising a heterologous nucleic acid. In some instances, the cells further comprise a lipid metabolism modifier (LMM), generally under the control of a promoter, capable of modulating lipid metabolism in the cell. In embodiments, the LMMs comprise global regulators that impact multiple aspects of pathways or processes involved in lipid metabolism, e.g., the de novo lipogenesis, fatty acid re-esterification, fatty acid saturation or desaturation, fatty acid elongation, and phospholipid biosynthesis pathways. By way of example, the global regulator is upstream in one or more lipid metabolism pathways or processes such that the global regulator impacts several, e.g., two or more, downstream processes or downstream components of lipid metabolism. In one embodiment, the global regulator is a transcription factor that can activate the expression of more than one, e.g., two or more, target genes involved in different lipid metabolism processes or pathways. Accordingly, without wishing to be bound by any theory, the use of a global regulator as described herein can result in a greater increase in production capacity, robustness, and survival of the cell than compared to the use of a downstream effector that modulates only a single target or other component of lipid metabolism. While not wishing to be bound by any theory, it is believed that a global or more widespread modulation of multiple lipid metabolism pathways increases the production capacity of a cell by affecting more processes involved in improving production capacity, product quality, and robustness of the cell.

Lipid metabolism pathways as described herein refer to processes that relate to the synthesis, degradation, conversion, or modification of lipids or lipid-associated molecules. Lipid molecules include, but are not limited to, fatty acids, glycerolipids, glycerophospholipids, phospholipids, saccharolipids, sphingolipids, and sterol lipids, e.g., cholesterol, and polyketides. Examples of lipid metabolism pathways include, but are not limited to: de novo lipogenesis, fatty acid re-esterification, fatty acid saturation, fatty acid de-saturation, fatty acid elongation, and phospholipid biosynthesis. In one embodiment, the methods described herein provide a cell comprising a modification that modulates lipid metabolism. The modification that modulates lipid metabolism can be an agent that increases or decreases the expression of a component involved in lipid metabolism. In one embodiment, the modification that modulates lipid metabolism comprises an exogenous nucleic acid encoding a lipid metabolism modulator (LMM). In such embodiments, the exogenous nucleic acid encoding a LMM is introduced to the cell by any of the nucleic acid delivery methods or techniques described herein, e.g., transduction or transfection.

In some embodiments, the methods described herein provide a cell comprising one or more, e.g., one, two, three, four, five, six, seven, eight, nine or ten, modifications that modulate lipid metabolism. In embodiments where the cell comprises two or more modifications that modulate lipid metabolism, each modification that modulates lipid metabolism comprises an exogenous nucleic acid that encodes a LMM. In one embodiment, each of the two or more exogenous nucleic acids that encode a LMM can be located within the same nucleic acid molecule, or are placed on two or more different nucleic acid molecules. In such embodiments where the cell comprises two or more nucleic acid sequences encoding LMMs, the LMMs are different from each other, e.g., encode a different polypeptide sequence or have a different function. In some embodiments, a plurality of different heterologous LMMs (e.g., 2, 3, 4, 5, 6, 7, 8, 9, 10, 11, 12, 13, 14, 15, 16, 17, 18, 19, 20, 30, 40, 50, 60, 70, 80, 90, 100, or more LMMs, e.g., as described herein) is expressed in the cell. In certain embodiments, one or more of the heterologous LMMs is naturally expressed by the cell. In certain embodiments, one or more of the heterologous LMMs is not naturally expressed by the cell.

In an embodiment, a modification that modulates lipid metabolism increases or decreases the expression or activity of a component involved in one or more lipid metabolism pathways. In some embodiments, the modulation of the lipid metabolism of a cell results in alteration of the spatial distribution of lipids in the cell, e.g., spatial distribution of lipids in the cell membrane (e.g., in lipid rafts), an organelle (e.g., endoplasmic reticulum, Golgi, nucleus, lysosomes, peroxisomes, vacuoles, and/or mitochondria), exosomes, droplets, or any other region or compartment of a cell comprising lipids. In embodiments where the modification that modulates lipid metabolism results in an increase in the expression, e.g., transcription or translation, or an increase in the activity of a component of a lipid metabolism pathway, the component is a positive regulator of the lipid metabolism pathway. In embodiments where the modification that modulates lipid metabolism results in a decrease in the expression, e.g., transcription, translation, turnover, and/or degradation, or a decrease in the activity of a component of a lipid metabolism pathway, the component is a negative regulator of the lipid metabolism pathway. Assays for quantifying the expression, e.g., transcription and/or translation, of a gene of the lipid metabolism pathway, are known in the art, and include quantifying the amount of mRNA encoding the gene; or quantifying the amount of the gene product, or polypeptide; PCR-based assays, e.g., quantitative real-time PCR; Northern blot; or microarray. Assays for quantifying the activity of a component of the lipid metabolism pathway, e.g., an enzyme of the lipid metabolism pathway, will be specific to the particular component of the lipid metabolism pathway.

In embodiments where the modulation of the lipid metabolism of a cell results in an increase in the level or amount of lipids in the cell, the total level or total amount of lipids in the cell can be increased. In some embodiments, the modulation of the lipid metabolism of a cell results in alteration of the spatial distribution of lipids in the cell, e.g., spatial distribution of lipids in the cell membrane (e.g., in lipid rafts), an organelle (e.g., endoplasmic reticulum, Golgi, nucleus, lysosomes, peroxisomes, vacuoles, and/or mitochondria), exosomes, droplets, or any other region or compartment of a cell comprising lipids. In one embodiment, a modification that modulates lipid metabolism results in increased cell survival. In one embodiment, a modification that modulates lipid metabolism results in increased culture viability. In one embodiment, a modification that modulates lipid metabolism results in increased cell proliferation. In one embodiment, a modification that modulates lipid metabolism results in an increase in production capacity, e.g., the amount, quantity, or yield of product produced, or the rate of production. In one embodiment, a modification that modulates lipid metabolism results in an increase in the quality of the product, e.g., aggregation, glycosylation status or heterogeneity, fragmentation, proper folding or assembly, post-translational modification, or disulfide bond scrambling.

In one embodiment, an LMM is overexpressed in a cell, e.g., by introducing a heterologous nucleic acid encoding a LMM (e.g., a nucleic acid originating from outside the cell, e.g., a nucleic acid construct comprising a gene encoding an LMM) or by increasing expression by introducing promoter elements or other regulatory transcriptional elements. In some embodiments, the cell comprises endogenous copies of the LMM being overexpressed in the cell. In other embodiments, the cell does not comprise endogenous copies of the LMM being overexpressed in the cell. In another embodiment, the expression or activity of an LMM is inhibited or decreased, e.g., by introducing an inhibitor of the LMM or an exogenous inhibitory nucleic acid, e.g., an RNA interfering agent. Examples of inhibitory nucleic acids include short interfering RNAs (siRNAs) and short hairpin RNAs (shRNAs) that target the LMM, e.g, the mRNA encoding the LMM. In one embodiment, the activity or expression of an LMM is increased or decreased by altering the post-translational modifications or other endogenous regulatory mechanisms that regulate LMM activity or expression. Regulation by post-translational modifications include, but are not limited to, phosphorylation, sumoylation, ubiquitination, acetylation, methylation, or glycosylation can increase or decrease LMM expression or activity. By way of example, regulation of post-translational modifications can be achieved through modulation of the enzyme or molecule that modifies the LMM, or modification of the LMM such that the post-translational modification cannot occur or occurs more frequently or constitutively. Regulation of the LMM can also include modulating endogenous regulatory mechanisms that can increase or decrease LMM expression or activity, e.g., increase or decrease one or more of: miRNA regulation, protein cleavage, expression of specific isoforms, alternative splicing, and degradation. In one embodiment, the LMM modulates, e.g., increases or decreases, the expression, e.g., transcription, or activity of a component of the lipid metabolism pathway. In another embodiment, the LMM modulates, e.g., increases or decreases, the synthesis, degradation, elongation, or structural conformation (e.g., saturation or desaturation, or esterification) of a lipid or lipid-associated molecule. Exemplary LMMs and/or components of the lipid metabolism pathway are listed, but not limited, to those listed in Table 2.

TABLE 2

Lipid Metabolism Pathways and Components/Gene Products Thereof

| Pathway | Component/Gene Product |
| --- | --- |
| Global Lipid Metabolism Regulators | SREBF1 (sterol regulatory element-binding transcription factor 1), e.g., truncated SREBF1 isoform c (SREB411) |
| | SREBF2 (sterol regulatory element-binding transcription factor 2) |
| | PRMT5 |
| De Novo Lipogenesis | FAS (fatty acid synthase) |
| | ACC (acetyl-coA carboxylase) |
| | ACL (ATP citrate lyase) |
| Fatty Acid Re-esterification | DGAT (diglyceride acyltransferase) |
| | GPAT (glycerol 3-phosphate acyltransferase) |
| | LPL (lipoprotein lipase) |
| Phospholipid Biosynthesis | AGPAT (1-actyl-sn-glycerol-3-phosphate O-acyltransferase) |
| | AGNPR (acyl/alkylglycerone-phosphate reductase) |
| | CCT (phosphocholine cytidyltransferase) |
| | CDS (phosphatidate cytidylyltransferase) |
| | CEPT (diacylglycerol choline/ehtanolaminephosphotransferase) |
| | CERT (ceramide transfer protein) |
| | CGT (N-acylsphingosine galactosyltransferase) |
| | CPT (diacylglycerol cholinephosphotransferase) |
| | CLS (cardiolipin synthase) |
| | CRD (ceramidase) |
| | GNPAT (glycerone-phosphate O-acyltransferase) |
| | KDSR (3-ketosphinganine reductase) |
| | LCS (polypeptide N-acetylgalactosaminyltransferase) |
| | PAP (phosphatidic acid phosphatase) |
| | PEMT (phosphatidylethanolamine N-methyltransferase) |
| | PGP (phosphatidylglycerophosphatase) |
| | PGS (CDP-diacylglycerol-glycerol-3-phosphate 3-phosphatidyltransferase) |
| | PIS (CDP-diacylglycerol-inositol 3-phosphatidyltransferase) |
| | PSD (phosphatidylserine decarboxylase) |
| | PSS1 (phosphatidylserine synthase 1) |
| | PSS2 (phosphatidylserine synthase 2) |
| | SGMS (ceramide choline phosphotransferase) |
| | SNAT (sphingosine N-acyltransferase) |
| | SPK (sphinganine kinase) |
| | SPP (sphingosine-1-phosphate phosphatase) |
| | SPT (serine Co-palmitoyltransferase) |
| Fatty Acid Desaturation | SCD1 (stearoyl CoA desaturase-1) |
| | SCD2 (stearoyl CoA desaturase-2) |
| | SCD3 (stearoyl CoA desaturase-3) |
| | SCD4 (stearoyl CoA desaturase-4) |
| | SCD5 (Steoryl CoA desaturase-5) |
| | PED (plasmanylethanolamine desaturase) |

TABLE 2-continued

Lipid Metabolism Pathways and Components/Gene Products Thereof

| Pathway | Component/Gene Product |
| --- | --- |
| Regulation of SREBF1 and other pathways | S1P (site-1 protease)<br>S2P (site-2 protease)<br>SCAP (SREBF cleavage-activating protein)<br>INSIG1 (insulin induced gene 1)<br>INSIG2 (insulin induced gene 2)<br>HMG CoA reductase (2-hydroxy-3-methylgulatryl-CoA reductase)<br>PPAR receptors, e.g., PPARα, PPARγ |

In embodiments, the LMM comprises at least 50%, 55%, 60%, 65%, 70%, 75%, 80%, 85%, 90%, 95%, 96%, 97%, 98%, 99%, or 100% amino acid sequence identity or homology with a component, e.g., gene product, involved in a lipid metabolism pathway, e.g., provided in Table 2; or differs by 1, 2, or 3 or more amino acid residues but no more than 50, 40, 30, 20, 15, or 10 amino acid residues from the amino acid sequence of a component, e.g., gene product, involved in the lipid metabolism pathway, e.g., provided in Table 2.

In embodiments, the LMM comprises a functional fragment of a component involved in the lipid metabolism pathway, e.g., provided in Table 2. A functional fragment of an LMM as described herein may comprise one or more functional domains of the LMM. By way of example, a functional fragment of a LMM that is a transcription factor comprises a DNA binding domain and a transactivation domain. By way of example, a functional fragment of a LMM that is an enzyme comprises a domain with enzymatic activity. A functional fragment of an LMM as described herein retains functional activity, e.g., at least 5%, 10%, 20%, 30%, 40%, 50%, 60%, 70%, 80%, or 90% of the functional activity, of the full-length LMM. Functional fragments of an LMM can be experimentally determined by one skilled in the art, or can be predicted using algorithms based on sequence homology of functional domains. Exemplary LMMs are further described below.

In any of the embodiments of the methods described herein, the LMM can be a transcriptional regulator. In embodiments, the LMM is a transcription factor or transcriptional activator, that binds to the DNA or associates in a complex that binds to DNA, and recruits or associates in a complex that recruits RNA polymerase for transcription of one or more gene products involved in lipid metabolism. In embodiments, the LMM binds to a sterol binding element and/or E-box promoter sequences. In embodiments, the LMM comprises sterol regulatory element binding factor 1 (SREBF1) or sterol regulatory element binding factor 2 (SREBF2) or a functional fragment or isoform thereof.

In some embodiments, the LMM comprises a global transcriptional activator or transcription factor. In embodiments, the LMM is capable of modulating the transcription of two or more, e.g., two, three, four, five, six, or more, components of a lipid metabolism pathway, e.g., as provided in any of Tables 3 or 4. In embodiments, the LMM is capable of modulating the transcription of one or more, e.g., one, two, three, four, or five, or more, components of two or more lipid metabolism pathways, e.g., components and pathways as provided in Table 2.

Sterol regulatory element binding factor 1 (SREBF1) is a global transcriptional activator which upregulates the transcription of genes involved in lipogenesis, fatty acid re-esterification, fatty acid desaturation and elongation, and phospholipid biosynthesis by binding to sterol regulatory element (SRE) and E-box promoter sequences (Hagen, Rodriguez-Cuenca et al. 2010) present in the promoter regions of target genes. Transcription of the SREBF1 gene itself is endogenously regulated by the presence of the sterol regulatory element (SRE) amongst other transcriptional regulating elements in the promoter region of the gene. On top of this, a multitude of posttranslational regulating mechanisms including phosphorylation, ubiquitination, sumoylation, acetylation, fatty acid-mediated modifications and proteolytic processing make for a tightly controlled but adaptable homeostatic system fixed around SREBF1.

In some embodiments, the LMM comprises an enzyme. In embodiments, the LMM comprises an enzyme that converts saturated fatty acids to unsaturated fatty acids. In embodiments, the LMM comprises an enzyme that converts saturated fatty acids to monounsaturated fatty acids, e.g., fatty acids with one double bond. In embodiments, the LMM comprises an enzyme that converts saturated fatty acids to polyunsaturated fatty acids, e.g., fatty acids with more than one, e.g., 2, 3, 4, 5, or more, double bonds. In embodiments, the LMM comprises stearoyl CoA desaturase 1 (SCD1), stearoyl CoA desaturase 2 (SCD2), stearoyl CoA desaturase 3 (SCD3), stearoyl CoA desaturase 4 (SCD4), stearoyl CoA desaturase 5 (SCD5), an isoform thereof, or a functional fragment thereof.

In some embodiments, an LMM present in a cell as described herein is under the control of a promoter. Desirably, the promoter is matched with the LMM gene to maximize production of the LMM by the cell. Non-limiting examples of promoters that can be used to regulate expression of an LMM include the SV40, mCMV, and PGK promoters. Non-limiting examples of combinations of promoters and LMM genes, e.g., which may be used, e.g., in any of the methods or compositions (e.g., cells) described herein, are shown in Table 3. It is contemplated that each of these combinations may be present in a cell that comprises P5CS, e.g., as introduced into the cell according to the methods described herein.

TABLE 3

Exemplary promoter-LMM combinations

| Promoter | Lipid Metabolism Modifier |
| --- | --- |
| SV40 | SCD1 (Mouse) |
| SV40 | SCD1 (CHO) |
| SV40 | SREBF1 (CHO) |
| SV40 | SREB411 (CHO) |
| mCMV | SCD1 (Mouse) |
| mCMV | SCD1 (CHO) |
| mCMV | SREBF1 (CHO) |
| mCMV | SREB411 (CHO) |
| hCMV | SCD1 (Mouse) |
| hCMV | SCD1 (CHO) |

TABLE 3-continued

Exemplary promoter-LMM combinations

| Promoter | Lipid Metabolism Modifier |
|---|---|
| hCMV | SREBF1 (CHO) |
| hCMV | SREB411 (CHO) |
| PGK | SCD1 (Mouse) |
| PGK | SCD1 (CHO) |
| PGK | SREBF1 (CHO) |
| PGK | SREB411 (CHO) |

Any of the promoter-LMM combinations described herein may be present in further combination with a gene encoding an enzyme molecule, e.g., in any of the cells, nucleic acids, or other compositions as described herein. For example, any of the promoter-LMM combinations described herein can be present in a cell that further comprises a nucleic acid encoding a P5CS molecule and comprising a subject nucleic acid as described herein. Furthermore, any of the promoter-LMM combinations described herein can be present in a cell with an inhibitor of an amino acid biosynthesis enzyme molecule (e.g., the enzyme molecule also present in the cell). For example, any of the promoter-LMM combinations described herein can be present in a cell that further comprises (i) a nucleic acid encoding a P5CS molecule and comprising a subject nucleic acid as described herein, and (ii) a P5CS inhibitor, e.g., L-azetidine-2-carboxylic acid, 3,4-dehydro-L-proline, or L-4-thiazolidinecarboxylic acid. Non-limiting examples of promoter-LMM-P5CS inhibitor combinations, e.g., which may be used, e.g., in any of the methods or compositions (e.g., cells) described herein, are shown in Table 4. It is contemplated that each of these combinations may be present in a cell that comprises P5CS, e.g., as introduced into the cell according to the methods described herein.

TABLE 4

Exemplary promoter-LMM-P5CS inhibitor combinations (e.g., in cells that comprise P5CS, as described herein)

| Promoter | Lipid Metabolism Modifier | P5CS inhibitor |
|---|---|---|
| SV40 | SCD1 (Mouse) | L-azetidine-2-carboxylic acid<br>3,4-Dehydro-L-Proline<br>L-4-Thiazolidinecarboxylic acid |
| SV40 | SCD1 (CHO) | L-azetidine-2-carboxylic acid<br>3,4-Dehydro-L-Proline<br>L-4-Thiazolidinecarboxylic acid |
| SV40 | SREBF1 (CHO) | L-azetidine-2-carboxylic acid<br>3,4-Dehydro-L-Proline<br>L-4-Thiazolidinecarboxylic acid |
| SV40 | SREB411 (CHO) | L-azetidine-2-carboxylic acid<br>3,4-Dehydro-L-Proline<br>L-4-Thiazolidinecarboxylic acid |
| mCMV | SCD1 (Mouse) | L-azetidine-2-carboxylic acid<br>3,4-Dehydro-L-Proline<br>L-4-Thiazolidinecarboxylic acid |
| mCMV | SCD1 (CHO) | L-azetidine-2-carboxylic acid<br>3,4-Dehydro-L-Proline<br>L-4-Thiazolidinecarboxylic acid |
| mCMV | SREBF1 (CHO) | L-azetidine-2-carboxylic acid<br>3,4-Dehydro-L-Proline<br>L-4-Thiazolidinecarboxylic acid |
| mCMV | SREB411 (CHO) | L-azetidine-2-carboxylic acid<br>3,4-Dehydro-L-Proline<br>L-4-Thiazolidinecarboxylic acid |
| hCMV | SCD1 (Mouse) | L-azetidine-2-carboxylic acid<br>3,4-Dehydro-L-Proline<br>L-4-Thiazolidinecarboxylic acid |
| hCMV | SCD1 (CHO) | L-azetidine-2-carboxylic acid<br>3,4-Dehydro-L-Proline<br>L-4-Thiazolidinecarboxylic acid |
| hCMV | SREBF1 (CHO) | L-azetidine-2-carboxylic acid<br>3,4-Dehydro-L-Proline<br>L-4-Thiazolidinecarboxylic acid |
| hCMV | SREB411 (CHO) | L-azetidine-2-carboxylic acid<br>3,4-Dehydro-L-Proline<br>L-4-Thiazolidinecarboxylic acid |
| PGK | SCD1 (Mouse) | L-azetidine-2-carboxylic acid<br>3,4-Dehydro-L-Proline<br>L-4-Thiazolidinecarboxylic acid |
| PGK | SCD1 (CHO) | L-azetidine-2-carboxylic acid<br>3,4-Dehydro-L-Proline<br>L-4-Thiazolidinecarboxylic acid |
| PGK | SREBF1 (CHO) | L-azetidine-2-carboxylic acid<br>3,4-Dehydro-L-Proline<br>L-4-Thiazolidinecarboxylic acid |
| PGK | SREB411 (CHO) | L-azetidine-2-carboxylic acid<br>3,4-Dehydro-L-Proline<br>L-4-Thiazolidinecarboxylic acid |

Cells and Cell Culture

In one aspect, the present disclosure relates to methods for evaluating, classifying, identifying, selecting, or making a cell or cell line that produces a product, e.g., a recombinant or therapeutic polypeptide or nucleic acid molecule as described herein. In another aspect, the present disclosure relates to methods and compositions for evaluating, classifying, identifying, selecting, or making a cell or cell line with improved, e.g., increased, productivity and product quality. Generally, the methods herein can be used to produce a cell or cell line comprising a nucleic acid construct (e.g., a vector or a heterologous nucleic acid integrated into the genome) comprising (i) a subject nucleic acid sequence encoding a product of interest and (ii) a nucleic acid sequence encoding an enzyme molecule that participates in the biosynthetic pathway of an amino acid, wherein the cell or cell line does not endogenously express the enzyme molecule.

In embodiments, the cell is a mammalian cell. In other embodiments, the cell is a cell other than a mammalian cell. In an embodiment, the cell is from mouse, rat, Chinese hamster, Syrian hamster, monkey, ape, dog, horse, ferret, or cat. In embodiments, the cell is a mammalian cell, e.g., a human cell or a rodent cell, e.g., a hamster cell, a mouse cell, or a rat cell. In another embodiment, the cell is from a duck, parrot, fish, insect, plant, fungus, or yeast.

In embodiments, the cell is a Chinese hamster ovary (CHO) cell. In one embodiment, the cell is a CHO-K1 cell, a CHOK1SV cell, a DG44 CHO cell, a DUXB11 CHO cell, a CHO-S, a CHO GS knock-out cell, a CHOK1SV FUT8 knock-out cell, a CHOZN, or a CHO-derived cell.

The CHO GS knock-out cell (e.g., GSKO cell) is, for example, a CHO-K1SV GS knockout cell (Lonza Biologics, Inc.). The CHO FUT8 knockout cell is, for example, the Potelligent® CHOK1SV FUT8 knock-out (Lonza Biologics, Inc.).

In embodiments, the cell is a HeLa, HEK293, HT1080, H9, HepG2, MCF7, Jurkat, NIH3T3, PC12, PER.C6, BHK (baby hamster kidney cell), VERO, SP2/0, NS0, YB2/0, Y0, EB66, C127, L cell, COS, e.g., COS1 and COS7, QC1-3, CHOK1, CHOK1SV, Potelligent™ (CHOK1SV FUT8-

KO), CHO GS knockout, Xceed™ (CHOK1SV GS-KO), CHOS, CHO DG44, CHO DXB11, and CHOZN, or any cells derived therefrom.

In embodiments, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In embodiments, the cell is a differentiated form of any of the cells described herein. In one embodiment, the cell is a cell derived from any primary cell in culture. In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic Küpffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Exemplary hepatocytes are commercially available from Triangle Research Labs, LLC, 6 Davis Drive Research Triangle Park, North Carolina, USA 27709.

In some embodiments, the cell comprises a knockout of glutamine synthetase (GS). In embodiments, the cell does not comprise a functional GS gene. In embodiments, the cell does not comprise a GS gene. In embodiments, the GS gene in a cell comprises a mutation that renders the gene incapable of encoding a functional GS protein.

In embodiments, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; and CBS7435.

In embodiments, the eukaryotic cell is a fungal cell (e.g. *Aspergillus* sp. (such as *A. niger, A. fumigatus, A. orzyae, A. nidula*), *Acremonium* sp. (such as *A. thermophilum*), *Chaetomium* sp. (such as *C. thermophilum*), *Chrysosporium* sp. (such as *C. thermophile*), *Cordyceps* sp. (such as *C. militaris*), *Corynascus* sp., *Ctenomyces* sp., *Fusarium* sp. (such as *F. oxysporum*), *Glomerella* sp. (such as *G. graminicola*), *Hypocrea* sp. (such as *H. jecorina*), *Magnaporthe* sp. (such as *M. orzyae*), *Myceliophthora* sp. (such as *M. thermophile*), *Nectria* sp. (such as *N. heamatococca*), *Neurospora* sp. (such as *N. crassa*), *Penicillium* sp., *Sporotrichum* sp. (such as *S. thermophile*), *Thielavia* sp. (such as *T. terrestris, T. heterothallica*), *Trichoderma* sp. (such as *T. reesei*), or *Verticillium* sp. (such as *V. dahlia*)).

In embodiments, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora* sp., *Bacillariophyceae* sp., *Dunaliella* sp., *Chlorella* sp., *Chlamydomonas* sp., *Cyanophyta* sp. (cyanobacteria), *Nannochloropsis* sp., *Spirulina* sp., or *Ochromonas* sp.), or a plant cell (e.g., cells from monocotyledonous plants (e.g., maize, rice, wheat, or *Setaria* sp.), or from a dicotyledonous plants (e.g., cassava, potato, soybean, tomato, tobacco, alfalfa, *Physcomitrella patens* or *Arabidopsis* sp.).

In embodiments, the cell is a bacterial or prokaryotic cell.

In embodiments, the prokaryotic cell is a Gram-positive cells such as *Bacillus* sp., *Streptomyces* sp., *Streptococcus* sp., *Staphylococcus* sp., or *Lactobacillus* sp. *Bacillus* sp. that can be used is, e.g. the *B. subtilis, B. amyloliquefaciens, B. licheniformis, B. natto,* or *B. megaterium*. In embodiments, the cell is *B. subtilis*, such as *B. subtilis* 3NA and *B. subtilis* 168. *Bacillus* sp. is obtainable from, e.g., the *Bacillus* Genetic Stock Center, Biological Sciences 556, 484 West 12$^{th}$ Avenue, Columbus OH 43210-1214.

In embodiments, the prokaryotic cell is a Gram-negative cell, such as *Salmonella* sp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), or BL21 (DE3) pLysS, all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cell is any one of the cells described herein that comprises a heterologous nucleic acid, e.g., a subject nucleic acid encoding a recombinant polypeptide, e.g., a recombinant polypeptide selected from Tables 5-8.

The cells described herein may be cultured according to any methods known in the art. In some embodiments, the culture media lacks an amino acid (e.g., one or more of the amino acids listed in Table 1). In embodiments, the culture media lacks an amino acid for which biosynthesis can be rescued if the cell has taken up the subject nucleic acid. In embodiments, the cell culture is carried out as a batch culture, fed-batch culture, abridged fed batch overgrow (aFOG), draw and fill culture, or a continuous culture. In an embodiment, the cell culture is a suspension culture. In one embodiment, the cell or cell culture is placed in vivo for expression of the recombinant polypeptide, e.g., placed in a model organism or a human subject.

In one embodiment, the culture media is free of serum. Serum-free, protein-free, and chemically-defined animal component-free (CDACF) media are commercially available, e.g., Lonza Biologics.

In some embodiments, lipid additives (e.g., comprising cholesterol, oleic acid, linoleic acid, or combinations thereof) can be added to the culture media.

Suitable media and culture methods for mammalian cell lines are well-known in the art, e.g., as described in U.S. Pat. No. 5,633,162. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1 p. 173 ff, 1963), Dulbecco's modified Eagle's medium (DMEM), Eagle's minimal essential medium (MEM), Ham's F12 medium (Ham, R. et al., Proc. Natl. Acad. Sc.53, p 288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. It is known that such culture media can be supplemented with fetal bovine serum (FBS, also called fetal calf serum FCS), the latter providing a natural source of a plethora of hormones and growth factors. The cell culture of mammalian cells is nowadays a routine operation well-described in scientific textbooks and manuals, it is covered in detail e.g. in R. Ian Fresney, Culture of Animal cells, a manual, 4$^{th}$ edition, Wiley-Liss/N.Y., 2000. Any of the cell culture media described herein can be formulated to lack a particular amino acid (e.g., an amino acid as listed in Table 1), e.g., the amino acid for which biosynthesis can be rescued if the cell has taken up the subject nucleic acid.

Other suitable cultivation methods are known to the skilled artisan and may depend upon the recombinant polypeptide product and the host cell utilized. It is within the skill of an ordinarily skilled artisan to determine or optimize conditions suitable for the expression and production of the recombinant or therapeutic polypeptide to be expressed by the cell.

Methods for genetically modifying or engineering a cell to express a desired polypeptide or protein are well known in the art, and include, for example, transfection, transduction (e.g., viral transduction), or electroporation, e.g., of a nucleic acid, e.g., a vector, into the cell. Examples of physical methods for introducing a nucleic acid, e.g., a heterologous nucleic acid or vector described herein, into a host cell include, without limitation, calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). Examples of chemical means for introducing a nucleic acid, e.g., a heterologous nucleic acid or vector described herein, into a host cell include, without limitation, colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable sub-micron sized delivery system.

Nucleic Acids

Also provided herein are nucleic acids, e.g., subject nucleic acids that encode the products, e.g., recombinant polypeptides, described herein. The nucleic acid sequences coding for the desired recombinant polypeptides can be obtained using recombinant methods known in the art, such as, for example by screening libraries from cells expressing the desired nucleic acid sequence, e.g., gene, by deriving the nucleic acid sequence from a vector known to include the same, or by isolating directly from cells and tissues containing the same, using standard techniques. Alternatively, the nucleic acid encoding the recombinant polypeptide can be produced synthetically, rather than cloned. Recombinant DNA techniques and technology are highly advanced and well established in the art. Accordingly, the ordinarily skilled artisan having the knowledge of the amino acid sequence of a recombinant polypeptide described herein can readily envision or generate the nucleic acid sequence that would encode the recombinant polypeptide.

The expression of the recombinant polypeptide is typically achieved by operably linking a nucleic acid encoding the recombinant polypeptide or portions thereof to a promoter, and incorporating the construct into an expression vector. The vectors can be suitable for replication and integration eukaryotes or prokaryotes. Typical cloning vectors contain other regulatory elements, such as transcription and translation terminators, initiation sequences, and promoters useful for regulation of the expression of the desired nucleic acid sequence.

In embodiments, the product, e.g., a heterologous therapeutic polypeptide, comprises multiple polypeptide chains, e.g., an antibody or antibody fragment that comprises a heavy and a light chain. The nucleic acid sequences encoding multiple polypeptide chains may be disposed together (e.g., each polypeptide chain encoding sequence disposed on the same nucleic acid) or separately (e.g., each polypeptide chain encoding sequence disposed on different nucleic acids). The sequences encoding a heterologous therapeutic polypeptide comprising multiple polypeptide chains may be operably linked to a single control element, e.g., a first control element, or to distinct, separate control elements (e.g., each polypeptide chain encoding sequence is operably linked to its own first control element). In an embodiment where the sequences encoding a heterologous therapeutic polypeptide comprising multiple polypeptide chains are operably linked to distinct, separate control elements, one or more (e.g., one, two, three, four, five, six, or all) of the control elements may have a first level of activity under a first condition and a second level of activity under a second condition, and one or more (e.g., one, two, three, four, five, six, or more) of the control elements may be constitutive.

The nucleic acid sequence encoding the recombinant polypeptide can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In embodiments, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a control element which comprises a promoter element and optionally an enhancer element, convenient restriction endonuclease sites, and one or more selectable markers, (e.g., WO 01/96584; WO 01/29058; and U.S. Pat. No. 6,326,193). Vectors derived from viruses are suitable tools to achieve long-term gene transfer since they allow long-term, stable integration of a transgene and its propagation in daughter cells.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection, e.g., a selection marker or a reporter gene.

Vectors contemplated may comprise insertion sites suitable for inserting sequences encoding polypeptides, e.g., exogenous therapeutic polypeptides or repressor polypeptides.

Insertion sites may comprise restriction endonuclease sites.

Insertion sites may comprise recombination target sites, wherein the recombination target sites flank the sequences encoding polypeptides, e.g., exogenous therapeutic polypeptides or repressor polypeptides. In an embodiment, the recombinant target site is a lox site. In case the recombination target site is a lox site, the host cells need the presence and expression of the Cre recombinase in order to achieve a cross-over or recombination event.

In embodiments, the vector comprising a nucleic acid sequence encoding a product, e.g., a polypeptide, e.g, a recombinant polypeptide, described herein further comprises a nucleic acid sequence that encodes a selection marker. In embodiments, the selection marker comprises glutamine synthetase (GS); dihydrofolate reductase (DHFR) e.g., an enzyme which confers resistance to methotrexate (MTX); proline, or an antibiotic marker, e.g., an enzyme that confers resistance to an antibiotic such as: hygromycin, neomycin (G418), zeocin, puromycin, or blasticidin. In embodiments, the selection marker comprises or is compatible with the Selexis selection system (e.g., SUREtechnology Platform™ and Selexis Genetic Elements™, commercially available from Selexis S A) or the Catalant selection system.

In embodiments, the vector comprising a nucleic acid sequence encoding a recombinant product described herein comprises a selection marker that is useful in identifying a cell or cells comprise the nucleic acid encoding a recombinant product described herein. In another embodiment, the selection marker is useful in identifying a cell or cells that comprise the integration of the nucleic acid sequence encoding the recombinant product into the genome, as described herein. The identification of a cell or cells that have integrated the nucleic acid sequence encoding the recombinant protein can be useful for the selection and engineering of a cell or cell line that stably expresses the product.

Products

Provided herein are compositions and methods for identifying, selecting, or culturing a cell or cell line capable of producing high yields of a product, e.g., a polypeptide, e.g., a therapeutic polypeptide. The products encompassed by the present disclosure include, but are not limited to, molecules, nucleic acids (e.g., non-coding nucleic acids, e.g., non-coding RNA molecules, e.g., an antisense RNA, siRNA, tRNA, ribosomal RNA, microRNA, piRNA, snoRNA, snRNA, exRNA, scaRNA, or long noncoding RNA, e.g., Xist or HOTAIR), polypeptides (e.g., recombinant and/or therapeutic polypeptides), or hybrids thereof, that can be produced by, e.g., expressed in, a cell. In some embodiments, the cells are engineered or modified to produce the product. Such modifications include introducing molecules that control or result in production of the product. For example, a cell is modified by introducing a heterologous nucleic acid that encodes a polypeptide, e.g., a recombinant polypeptide, and the cell is cultured under conditions suitable for production, e.g., expression and secretion, of the polypeptide, e.g., recombinant polypeptide. In another example, a cell is modified by introducing a heterologous nucleic acid that controls, e.g., increases, expression of a polypeptide that is endogenously expressed by the cell, such that the cell produces a higher level or quantity of the polypeptide than the level or quantity that is endogenously produced, e.g., in an unmodified cell. In embodiments, the cell or cell line identified, selected, or generated by the methods described herein produces a product, e.g., a recombinant polypeptide, useful in the treatment of a medical condition, disorder or disease. Examples of medical conditions, disorders or diseases include, but are not limited to, metabolic disease or disorders (e.g., metabolic enzyme deficiencies), endocrine disorders (e.g., hormone deficiencies), haemostasis, thrombosis, hematopoietic disorders, pulmonary disorders, gastro-intestinal disorders, immunoregulation (e.g., immunodeficiency), infertility, transplantation, cancer, and infectious diseases.

Polypeptides

In some embodiments, the product is a polypeptide, e.g, a recombinant polypeptide. Polypeptide products may, in some embodiments, be used in any of the compositions (e.g., cells) and methods described herein. In some embodiments, a polypeptide is produced by a cell grown in media comprising an inhibitor, e.g., of an enzyme molecule, e.g., as described herein. In some embodiments, a polypeptide is produced by a cell comprising an LMM, e.g., as described herein. In embodiments, the LMM is expressed under the control of a promoter, e.g., as described herein. In some embodiments, a polypeptide is produced by a cell grown in media comprising an LMM, e.g., as described herein.

In embodiments, the polypeptide is a heterologous polypeptide, e.g., a heterologous protein, e.g., a protein that is not naturally expressed by the cell. The polypeptide can be a therapeutic protein or a diagnostic protein, e.g., useful for drug screening. The therapeutic or diagnostic protein can be an antibody molecule, e.g., an antibody or an antibody fragment, a fusion protein, a hormone, a cytokine, a growth factor, an enzyme, a glycoprotein, a lipoprotein, a reporter protein, a therapeutic peptide, an aptamer, or a structural and/or functional fragment or hybrid of any of these. In embodiments, the product, e.g., a heterologous therapeutic polypeptide, comprises multiple polypeptide chains, e.g., an antibody or antibody fragment that comprises a heavy and a light chain.

In some embodiments, the product, e.g., recombinant polypeptide is an antibody molecule. Products encompassed herein are diagnostic antibody molecules, e.g., a monoclonal antibody or antibody fragment thereof, useful for imaging techniques, and therapeutic antibody molecules suitable for administration to subjects, e.g., useful for treatment of diseases or disorders. An antibody molecule is a protein, or polypeptide sequence derived from an immunoglobulin molecule which specifically binds with an antigen. In an embodiment, the antibody molecule is a full-length antibody or an antibody fragment. Antibodies and multiformat proteins can be polyclonal or monoclonal, multiple or single chain, or intact immunoglobulins, and may be derived from natural sources or from recombinant sources. Antibodies can be tetramers of immunoglobulin molecules. In an embodiment, the antibody is a monoclonal antibody. The antibody may be a human or humanized antibody. In one embodiment, the antibody is an IgA, IgG, IgD, or IgE antibody. In one embodiment, the antibody is an IgG1, IgG2, IgG3, or IgG4 antibody.

"Antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', $F(ab')_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

In embodiments, the polypeptide (e.g., produced by a cell and/or according to the methods described herein) is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide, calcitonin, etanercept, hemoglobin glutamer 250 (bovine), drotrecogin alpha, collagenase, carperitide, recombinant human epidermal growth factor, DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (Hydron), deslorelin, histrelin, nafarelin, leuprolide (ATRIGEL), leuprolide (DUROS), goserelin, Eutropin, somatropin, mecasermin, enlfavirtide, Org-33408, insulin glargine, insulin glulisine, insulin (inhaled), insulin lispro, insulin deternir, insulin (RapidMist), mecasermin rinfabate, anakinra, celmoleukin, 99 mTc-apcitide, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, octreotide, lanreotide, ancestirn, agalsidase beta, agalsidase alpha, laronidase, prezatide copper acetate, rasburicase, ranibizumab, Actimmune, PEG-Intron, Tricomin, recombinant human parathyroid hormone (PTH) 1-84, epoetin delta, transgenic antithrombin III, Granditropin, Vitrase, recombinant insulin, interferon-alpha, GEM-21S, vapreotide, idursulfase, omnapatrilat, recombinant serum albumin, certolizumab pegol, glucarpidase, human recombinant C1 esterase inhibitor, lanoteplase, recombinant human growth hormone, enfuvirtide, VGV-1, interferon (alpha), lucinactant, aviptadil, icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide, tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone, recombinant G-CSF, insulin, insulin (Technosphere), insulin (AERx), RGN-303, DiaPep277, interferon beta, interferon alpha-n3, belatacept, transdermal insulin patches, AMG-531, MBP-8298, Xerecept, opebacan, AIDSVAX, GV-1001, LymphoScan, ranpirnase, Lipoxysan, lusupultide, MP52, sipuleucel-T, CTP-37, Insegia, vitespen, human thrombin, thrombin, TransMID, alfimeprase, Puricase, terlipressin, EUR-1008M, recombinant FGF-I, BDM-E, rotigaptide, ETC-216, P-113, MBI-594AN, duramycin, SCV-07, OPI-45, Endostatin, Angiostatin, ABT-510, Bowman Birk Inhibitor, XMP-629, 99 mTc-Hynic-Annexin V, kahalalide F, CTCE-9908, teverelix, ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, SB-249553, Oncovax-CL, Onco-Vax-P, BLP-25, CerVax-16, MART-1, gp100, tyrosinase, nemifitide, rAAT, CGRP, pegsunercept, thymosinbeta4, plitidepsin, GTP-200, ramoplanin, GRASPA, OBI-1, AC-100, salmon calcitonin (eligen), examorelin, capromorelin, Cardeva, velafermin, 131I-TM-601, KK-220, T-10, ularitide, depelestat, hematide, Chrysalin, rNAPc2, recombinant Factor V111 (PEGylated liposomal), bFGF, PEGylated recombinant staphylokinase variant, V-10153, SonoLysis Prolyse, NeuroVax, CZEN-002, rGLP-1, BIM-51077, LY-548806, exenatide (controlled release, Medisorb), AVE-0010, GA-GCB, avorelin, ACM-9604, linaclotid eacetate, CETi-1, Hemospan, VAL, fast-acting insulin (injectable, Viadel), insulin (eligen), recombinant methionyl human leptin, pitrakinra, Multikine, RG-1068, MM-093, NBI-6024, AT-001, PI-0824, Org-39141, Cpn10, talactoferrin, rEV-131, rEV-131, recombinant human insulin, RPI-78M, oprelvekin, CYT-99007 CTLA4-Ig, DTY-001, valategrast, interferon alpha-n3, IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, ALTU-135, recombinant neuraminidase, Vacc-5q, Vacc-4x, Tat Toxoid, YSPSL, CHS-13340, PTH(1-34) (Novasome), Ostabolin-C, PTH analog, MBRI-93.02, MTB72F, MVA-Ag85A, FARA04, BA-210, recombinant plague FIV, AG-702, OxSODro1, rBetV1, Der-p1/Der-p2/Der-p7, PR1 peptide antigen, mutant ras vaccine, HPV-16 E7 lipopeptide vaccine, labyrinthin, WT1-peptide, IDD-5, CDX-110, Pentrys, Norelin, CytoFab, P-9808, VT-111, icrocaptide, telbermin, rupintrivir, reticulose, rGRF, HA, alpha-galactosidase A, ACE-011, ALTU-140, CGX-1160, angiotensin, D-4F, ETC-642, APP-018, rhMBL, SCV-07, DRF-7295, ABT-828, ErbB2-specific immunotoxin, DT3SSIL-3, TST-10088, PRO-1762, Combotox, cholecystokinin-B/gastrin-receptor binding peptides, 111In-hEGF, AE-37, trasnizumab-DM1, Antagonist G, IL-12, PM-02734, IMP-321, rhIGF-BP3, BLX-883, CUV-1647, L-19 based ra, Re-188-P-2045, AMG-386, DC/1540/KLH, VX-001, AVE-9633, AC-9301, NY-ESO-1 (peptides), NA17.A2 peptides, CBP-501, recombinant human lactoferrin, FX-06, AP-214, WAP-8294A, ACP-HIP, SUN-11031, peptide YY [3-36], FGLL, atacicept, BR3-Fc, BN-003, BA-058, human parathyroid hormone 1-34, F-18-CCR1, AT-1100, JPD-003, PTH (7-34) (Novasome), duramycin, CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix, EP-51216, hGH, OGP-I, sifuvirtide, TV4710, ALG-889, Org-41259, rhCC10, F-991, thymopentin, r(m)CRP, hepatoselective insulin, subalin, L19-IL-2 fusion protein, elafin, NMK-150, ALTU-139, EN-122004, rhTPO, thrombopoietin receptor agonist, AL-108, AL-208, nerve growth factor antagonists, SLV-317, CGX-1007, INNO-105, teriparatide (eligen), GEM-OS1, AC-162352, PRX-302, LFn-p24 fusion, EP-1043, gpE1, gpE2, MF-59, hPTH(1-34), 768974, SYN-101, PGN-0052, aviscumnine, BIM-23190, multi-epitope tyrosinase peptide, enkastim, APC-8024, GI-5005, ACC-001, TTS-CD3, vascular-targeted TNF, desmopressin, onercept, and TP-9201.

In some embodiments, the polypeptide (e.g., produced by a cell and/or according to the methods described herein) is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides (e.g., produced by a cell and/or according to the methods described herein) include, but are not limited to, those listed below in Table 5 and in Table 1 of US2016/0097074.

TABLE 5

Exemplary Polypeptides

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Anglomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ®FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |

TABLE 5-continued

Exemplary Polypeptides

| Protein Product | Reference Listed Drug |
|---|---|
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide (e.g., produced by a cell and/or according to the methods described herein) is a hormone, blood clotting/coagulation factor, cytokine/growth factor, antibody molelcule, fusion protein, protein vaccine, or peptide, e.g., as shown in Table 6.

TABLE 6

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin , Humatrope, Norditropin, NovIVitropin, |
| | Human follicle-stimulating hormone (FSH) | Nutropin, Omnitrope, Protropin, Siazen, Serostim, |
| | Human chorionic gonadotropin | Valtropin Gonal-F, Follistim |
| | Lutropin-α | Ovidrel |
| | Glucagon | Luveris |
| | Growth hormone releasing hormone (GHRH) | GlcaGen |
| | Secretin | Geref |
| | Thyroid stimulating hormone (TSH), thyrotropin | ChiRhoStim (human peptide), SecreFlo (porcine peptide) Thyrogen |
| Blood Clotting/Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN- β) | Avonex, Rebif |
| | Interferon-β1b (rIFN- β) | Betaseron |
| | Interferon-y1b (IFN γ) | Actimmune |
| | Aldesleukin (interleukin 2(IL2), epidermal theymocyte activating factor; ETAF | Proleukin Kepivance |
| | Palifermin (keratinocyte growth factor; KGF) | Regranex |
| | Becaplemin (platelet-derived growth factor; PDGF) | Anril, Kineret |
| | Anakinra (recombinant IL1 antagonist) | |
| Antibody molecules | Bevacizumab (VEGFA mAb) | A vastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/ Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac Fuzeon |
| | Enfuvirtide | QMONOS |
| | Spider silk, e.g., fibrion | |

In embodiments, the polypeptide (e.g., produced by a cell and/or according to the methods described herein) is a multispecific protein, e.g., a bispecific antibody. In embodiments, the multispecific protein is as shown in Table 7.

TABLE 7

Exemplary Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |

TABLE 7-continued

Exemplary Bispecific Formats

| Name (other names, sponsoring organizations) | BsAb format | Targets | Proposed mechanisms of action | Development stages | Diseases (or healthy volunteers) |
|---|---|---|---|---|---|
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx;) | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

In embodiments, the polypeptide (e.g., produced by a cell and/or according to the methods described herein) is one listed in Table 8.

TABLE 8

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |

TABLE 8-continued

| Protein Product | Reference Listed Drug |
| --- | --- |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone Antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In some embodiments, the polypeptide (e.g., produced by a cell and/or according to the methods described herein) is an antigen expressed by a cancer cell. In some embodiments the recombinant or therapeutic polypeptide is a tumor-associated antigen or a tumor-specific antigen. In some embodiments, the recombinant or therapeutic polypeptide is selected from HER2, CD20, 9-O-acetyl-GD3, βhCG, A33 antigen, CA19-9 marker, CA-125 marker, calreticulin, carboanhydrase IX (MN/CA IX), CCR5, CCR8, CD19, CD22, CD25, CD27, CD30, CD33, CD38, CD44v6, CD63, CD70, CC123, CD138, carcinoma embryonic antigen (CEA; CD66e), desmoglein 4, E-cadherin neoepitope, endosialin, ephrin A2 (EphA2), epidermal growth factor receptor (EGFR), epithelial cell adhesion molecule (EpCAM), ErbB2, fetal acetylcholine receptor, fibroblast activation antigen (FAP), fucosyl GM1, GD2, GD3, GM2, ganglioside GD3, Globo H, glycoprotein 100, HER2/neu, HER3, HER4, insulin-like growth factor receptor 1, Lewis-Y, LG, Ly-6, melanoma-specific chondroitin-sulfate proteoglycan (MCSCP), mesothelin, MUC1, MUC2, MUC3, MUC4, $MUC5_{AC}$, $MUC5_{B}$, MUC7, MUC16, Mullerian inhibitory substance (MIS) receptor type II, plasma cell antigen, poly SA, PSCA, PSMA, sonic hedgehog (SHH), SAS, STEAP, sTn antigen, TNF-alpha precursor, and combinations thereof.

In some embodiments, the polypeptide (e.g., produced by a cell and/or according to the methods described herein) is an activating receptor and is selected from 2B4 (CD244), $α_4β_1$ integrin, $β_2$ integrins, CD2, CD16, CD27, CD38, CD96, CD1OO, CD160, CD137, CEACAM1 (CD66), CRTAM, CS1 (CD319), DNAM-1 (CD226), GITR (TNFRSF18), activating forms of KIR, NKG2C, NKG2D, NKG2E, one or more natural cytotoxicity receptors, NTB-A, PEN-5, and combinations thereof, optionally wherein the $β_2$ integrins comprise CD11a-CD 18, CD11 b-CD 18, or CD11c-CD 18, optionally wherein the activating forms of KIR comprise K1R2DS1, KIR2DS4, or KIR-S, and optionally wherein the natural cytotoxicity receptors comprise NKp30, NKp44, NKp46, or NKp80.

In some embodiments, the polypeptide (e.g., produced by a cell and/or according to the methods described herein) is an inhibitory receptor and is selected from KIR, ILT2/LIR-1/CD85j, inhibitory forms of KIR, KLRG1, LAIR-1, NKG2A, NKR-P1A, Siglec-3, Siglec-7, Siglec-9, and combinations thereof, optionally wherein the inhibitory forms of KIR comprise KIR2DL1, KIR2DL2, KIR2DL3, KIR3DL1, KIR3DL2, or KIR-L.

In some embodiments, the polypeptide (e.g., produced by a cell and/or according to the methods described herein) is an activating receptor and is selected from CD3, CD2 (LFA2, OX34), CD5, CD27 (TNFRSF7), CD28, CD30 (TNFRSF8), CD40L, CD84 (SLAMF5), CD137 (4-1BB), CD226, CD229 (Ly9, SLAMF3), CD244 (2B4, SLAMF4), CD319 (CRACC, BLAME), CD352 (Ly108, NTBA, SLAMF6), CRTAM (CD355), DR3 (TNFRSF25), GITR (CD357), HVEM (CD270), ICOS, LIGHT, LTβR (TNFRSF3), OX40 (CD134), NKG2D, SLAM (CD150, SLAMF1), TCRα, TCRβ, TCRδγ, TIM1 (HAVCR, KIM1), and combinations thereof.

In some embodiments, the polypeptide (e.g., produced by a cell and/or according to the methods described herein) is an inhibitory receptor and is selected from PD-1 (CD279), 2B4 (CD244, SLAMF4), B71 (CD80), B7H1 (CD274, PD-L1), BTLA (CD272), CD160 (BY55, NK28), CD352 (Ly108, NTBA, SLAMF6), CD358 (DR6), CTLA-4 (CD152), LAG3, LAIR1, PD-1H (VISTA), TIGIT (VSIG9, VSTM3), TIM2 (TIMD2), TIM3 (HAVCR2, KIM3), and combinations thereof.

Other exemplary polypeptides (e.g., produced by a cell and/or according to the methods described herein) include, but are not limited to any protein described in Tables 1-10 of Leader et al., "Protein therapeutics: a summary and pharmacological classification", Nature Reviews Drug Discovery, 2008, 7:21-39 (incorporated herein by reference); or any conjugate, variant, analog, or functional fragment of the recombinant polypeptides described herein.

Other recombinant protein products (e.g., produced by a cell and/or according to the methods described herein) include non-antibody scaffolds or alternative protein scaffolds, such as, but not limited to: DARPins, affibodies and adnectins. Such non-antibody scaffolds or alternative protein scaffolds can be engineered to recognize or bind to one or two, or more, e.g., 1, 2, 3, 4, or 5 or more, different targets or antigens.

Applications

The methods of identifying, selecting, and/or culturing cells as disclosed herein can be used to generate cells useful for producing a variety of products, evaluate various cell lines, or to evaluate the production of various cell lines for use in a bioreactor or processing vessel or tank, or, more generally with any feed source. The compositions and methods described herein are suitable for culturing any desired cell line, including, e.g., prokaryotic and/or eukaryotic cell lines. Further, in embodiments, the compositions and methods described herein are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the compositions and methods described herein can be used for producing biosimilars.

As mentioned, in embodiments, compositions and methods described herein allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesized by the eukaryotic cells in a large-scale manner. Unless stated otherwise herein, the compositions and methods described herein can include any desired volume or production capacity including but not limited to bench-scale, pilot-scale, and full production scale capacities.

Moreover and unless stated otherwise herein, the compositions and methods described herein can be used with any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." For example, in some aspects, a bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 ml and about 50,000 L. Non-limiting examples include a volume of 100 ml, 250 ml, 500 ml, 750 ml, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass. In some embodiments, suitable reactors can be round, e.g., cylindrical. In some embodiments, suitable reactors can be square, e.g., rectangular. Square reactors may in some cases provide benefits over round reactors such as ease of use (e.g., loading and setup by skilled persons), greater mixing and homogeneity of reactor contents, and lower floor footprint.

In embodiments and unless stated otherwise herein, the compositions and methods described herein can be used with any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the compositions and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe exemplary facilities, equipment, and/or systems that may be suitable for use with the compositions and methods described herein.

The compositions and methods described herein can utilize a broad spectrum of cells. In embodiments, the cells are eukaryotic cells, e.g., mammalian cells. The mammalian cells can be, for example, human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, North Carolina, USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica,* or *Schizosaccharomyces*

*pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

Numbered Embodiments

The present invention may be defined, for example, as in any of the following numbered paragraphs.

1. A method of identifying, selecting or culturing a cell comprising a subject nucleic acid sequence, the method comprising:
    a) providing a cell comprising a heterologous nucleic acid, e.g., a vector, e.g., a replicable vector or integrating vector, comprising:
        (i) the subject nucleic acid sequence; and
        (ii) a nucleic acid sequence that when expressed results in an elevated level of activity of an enzyme in the synthetic pathway of an amino acid, e.g., the proline synthetic pathway, e.g., a nucleic acid sequence that encodes an enzyme molecule that comprises the activity; and
    b) culturing the cell comprising the nucleic acid sequence in the presence of media having an insufficient level of the amino acid, e.g., proline, to support growth of a cell that is the same as the cell not having elevated activity, under conditions sufficient to allow for growth of a cell comprising the nucleic acid sequence,
thereby identifying, selecting or culturing, a cell comprising the heterologous nucleic acid sequence.

2. The method of embodiment 1, wherein the heterologous nucleic acid comprises a vector.

3. The method of any of the preceding embodiments, wherein the heterologous nucleic acid comprises a replicable vector, e.g., a self-replicable vector.

4. The method of any of the preceding embodiments, wherein the heterologous nucleic acid comprises an integrating vector.

5. The method of any of the preceding embodiments, wherein the media further comprises an inhibitor of activity of the enzyme.

6. The method of embodiment 5, wherein the inhibitor is the amino acid.

7. The method of embodiment 5, wherein the inhibitor is not the amino acid.

8. The method of any of the preceding embodiments, comprising identifying a cell comprising a heterologous nucleic acid sequence.

9. The method of any of the preceding embodiments, comprising selecting a cell comprising a heterologous nucleic acid sequence.

10. The method of any of the preceding embodiments, comprising culturing a cell comprising a heterologous nucleic acid sequence.

11. The method of any of the preceding embodiments, wherein the heterologous nucleic acid comprises a plurality of vectors (e.g., wherein the subject nucleic acid and the nucleic acid resulting in an elevated level of activity of an enzyme are comprised in a plurality of vectors, e.g., on different vectors).

12. The method of any of the preceding embodiments, wherein the heterologous nucleic acid comprises a plurality of integrating vectors (e.g., wherein the subject nucleic acid and the nucleic acid resulting in an elevated level of activity of an enzyme are comprised in a plurality of integrating vectors, e.g., on different vectors).

13. The method of any of the preceding embodiments, wherein the heterologous nucleic acid comprises a plurality of self-replicating vectors (e.g., wherein the subject nucleic acid and the nucleic acid resulting in an elevated level of activity of an enzyme are comprised in a plurality of self-replicating vectors, e.g., on different vectors).

14. The method of any of the preceding embodiments, wherein the heterologous nucleic acid is integrated into the genome, e.g., the chromosomal genome, of the cell.

15. The method of any of the preceding embodiments, wherein the amino acid comprises a naturally occurring amino acid.

16. The method of any of the preceding embodiments, wherein the amino acid comprises an amino acid listed in Table 1.

17. The method of embodiment 16, wherein the amino acid is alanine.

18. The method of embodiment 16, wherein the amino acid is leucine.

19. The method of embodiment 16, wherein the amino acid is isoleucine.

20. The method of embodiment 16, wherein the amino acid is methionine.

21. The method of embodiment 16, wherein the amino acid is valine.

22. The method of embodiment 16, wherein the amino acid is phenylalanine.

23. The method of embodiment 16, wherein the amino acid is asparagine.

24. The method of embodiment 16, wherein the amino acid is cysteine.

25. The method of embodiment 16, wherein the amino acid is glutamine.

26. The method of embodiment 16, wherein the amino acid is serine.

27. The method of embodiment 16, wherein the amino acid is threonine.

28. The method of embodiment 16, wherein the amino acid is aspartic acid.

29. The method of embodiment 16, wherein the amino acid is glutamic acid.

30. The method of embodiment 16, wherein the amino acid is arginine.

31. The method of embodiment 16, wherein the amino acid is histidine.

32. The method of embodiment 16, wherein the amino acid is lysine.

33. The method of embodiment 16, wherein the amino acid is glycine.

34. The method of any of embodiments 1-16, wherein the amino acid is selected from proline, tyrosine, and tryptophan.

35. The method of embodiment 34, wherein the amino acid is proline.

36. The method of embodiment 34, wherein the amino acid is tyrosine.

37. The method of embodiment 34, wherein the amino acid is tryptophan.

38. The method of any of embodiments 5-37, wherein the inhibitor binds to the enzyme, e.g., it binds to and inhibits the enzyme.

39. The method of any of embodiments 5-38, wherein the inhibitor inhibits the transcription of the enzyme.

40. The method of any of embodiments 5-39, wherein the inhibitor inhibits the translation of the enzyme.

41. The method of any of embodiments 5-40, wherein the inhibitor comprises a nucleic acid, e.g., an RNA, e.g., an antisense or siRNA.

42. The method of any of embodiments 5-41, wherein the inhibitor comprises an aptamer.

43. The method of any of embodiments 5-42, wherein the inhibitor comprises a small molecule.

44. The method of any of embodiments 5-43, wherein the inhibitor is an analog of a substrate of the enzyme.

45. The method of any of embodiments 5-44, wherein the inhibitor is an analog of the amino acid e.g., an analog of proline, tyrosine, or tryptophan.

46. The method of any of embodiments 5-45, wherein the inhibitor comprises a competitive inhibitor.

47. The method of any of embodiments 5-46, wherein the inhibitor inhibits the rate limiting enzyme for synthesis of the amino acid, e.g., the inhibitor inhibits the rate limiting enzyme for synthesis of the amino acid on the media.

48. The method of any of the preceding embodiments, wherein the amino acid comprises proline.

49. The method of any of the preceding embodiments, wherein the enzyme comprises a pyroline-5-carboxylate synthase (P5CS) molecule.

50. The method of any of the preceding embodiments, wherein the heterologous nucleic acid sequence comprises a sequence that encodes a P5CS molecule.

51. The method of any of embodiments 5-50, wherein the inhibitor is a substrate of the enzyme, or an analog, variant, or derivative thereof.

52. The method of any of the preceding embodiments, wherein the inhibitor is an analog of proline, e.g., L-azetidine-2-carboxylic acid, 3,4-dehydro-L-proline, or L-4-thiazolidinecarboxylic acid.

53. The method of any of embodiments 5-52, wherein the amino acid comprises proline and the enzyme and inhibitor are selected from Table 1.

54. The method of any of embodiments 5-16, 34, or 38-47, wherein the amino acid comprises tyrosine and the enzyme and/or inhibitor are selected from Table 1.

55. The method of any of embodiments 5-16, 34, 38-47, or 54, wherein the heterologous nucleic acid sequence comprises a sequence that encodes a polypeptide and/or an inhibitor of a tyrosine biosynthesis enzyme.

56. The method of any of embodiments 54 or 55, wherein the inhibitor is an analog of a substrate of the enzyme.

57. The method of any of embodiments 5-16, 34, 38-47, or 54-56, wherein the inhibitor is an analog of tyrosine.

58. The method of any of embodiments 5-16, 34, 38-47, or 54-57, wherein the amino acid comprises tyrosine and the enzyme and inhibitor are selected from Table 1.

59. The method of any of embodiment 5-16, 34, or 38-47, wherein the amino acid comprises tryptophan and the enzyme and/or inhibitor are selected from Table 1.

60. The method of any of embodiments 5-16, 34, 38-47, or 59, wherein the heterologous nucleic acid sequence comprises a sequence that encodes a polypeptide and/or an inhibitor of a tryptophan biosynthesis enzyme.

61. The method of any of embodiments 59 or 60, wherein the inhibitor is an analog of a substrate of the enzyme.

62. The method of any of embodiments 5-16, 34, 38-47, or 59-61, wherein the inhibitor is an analog of tryptophan.

63. The method of any of embodiments 5-16, 34, 38-47, or 59-62, wherein the amino acid comprises tryptophan and the enzyme and inhibitor are selected from Table 1.

64. The method of any of the preceding embodiments, comprising culturing a cell not having the elevated enzyme activity together with the cell having elevated activity.

65. The method of any of the preceding embodiments, wherein the cells with elevated activity grow more quickly than cells not having elevated activity, e.g., about 2, 3, 4, 5, 6, 7, 8, 9, 10, 20, 30, 40, 50, 75, 100, 150, 200, 300, 400, 500, 600, 700, 800, 900, 1000, 2000, 3000, 4000, 5000, 6000, 7000, 8000, 9000, or 10,000 times more quickly.

66. The method of any of the preceding embodiments, wherein less than about 0.01, 0.1, 0.5, 1, 2, 3, 4, 5, 6, 7, 8, 9, 10, 20, 30, 40, or 50 percent of the cells selected, e.g., selected on the basis of growth, lack the nucleic acid.

67. The method of any of the preceding embodiments, further comprising selecting a cell that exhibits growth.

68. The method of any of the preceding embodiments, wherein the cell comprises a eukaryotic cell.

69. The method of any of the preceding embodiments, wherein the cell comprises an animal cell.

70. The method of any of the preceding embodiments, wherein the cell comprises a mammalian cell.

71. The method of any of the preceding embodiments, wherein the cell comprises a rodent cell.

72. The method of any of the preceding embodiments, wherein the cell comprises a CHO cell.

73. The method of any of the preceding embodiments, wherein the cell comprises a GSKO CHO cell.

74. The method of any of the preceding embodiments, wherein an endogenous copy of a sequence that encodes the enzyme has been inactivated, e.g., comprises a deletion in the structural or control region.

75. The method of any of the preceding embodiments, wherein an endogenous copy of a sequence that encodes a second amino acid synthetic enzyme has been inactivated, e.g., comprises a deletion in the structural or control region.

76. The method of any of the preceding embodiments, wherein an endogenous copy of a sequence that encodes the GS has been inactivated, e.g., comprises a deletion in the structural or control region.

77. The method of any of the preceding embodiments, wherein the subject nucleic acid sequence encodes a peptide molecule.

78. The method of any of the preceding embodiments, wherein the subject nucleic acid sequence is heterologous.

79. The method of any of the preceding embodiments wherein the heterologous peptide molecule is selected from any of Tables 5-8.

80. The method of any of the preceding embodiments, comprising selecting a cell which grows on the media.

81. The method of embodiment 80, wherein the media comprises inhibitor.

82. The method of any of the preceding embodiments, comprising:
  1) selecting a cell which grows on the media; and
  2) culturing the cell under a second set of culture conditions, e.g., on a second media, e.g., subjecting the selected cell to a second selection.

83. The method of embodiment 82, wherein:
  the media in 1) comprises the inhibitor; and
  the second media in 2) comprises the inhibitor.

84. The method of any of the preceding embodiments, comprising:
  1) selecting a cell which grows on the media; and
  2) culturing the cell under a second set of culture conditions, e.g., on a second media, e.g., subjecting the selected cell to a second selection.
  wherein the concentration of the inhibitor in the media of one of 1) and 2) is greater than the concentration of the inhibitor in the other of 1) and 2).

85. The method of embodiment 84, wherein:
  the concentration of the inhibitor in 1) is greater than the concentration of inhibitor in 2).

86. The method of embodiment 84, wherein the concentration of the inhibitor in 1) is greater than the concentration of inhibitor in 2).

87. The method of any of embodiments 84-86, comprising:
  wherein the media in the step having a lower concentration of the inhibitor is essentially free of inhibitor.

88. The method of any of the preceding embodiments, wherein the nucleic acid sequence of (ii) is operatively linked with a control sequence, e.g., a promoter.

89. The method of embodiment 88, wherein the control sequence comprises a sequence selected from the SV40, mCMV, hCMV, or PGK promoters, or variants thereof.

90. The method of embodiment 88, wherein the control sequence controls the expression of an LMM.

91. The method of embodiment 90, wherein the control sequence and LMM are as listed in any single row of Table 3.

92. The method of embodiment 90, wherein the control sequence comprises an SV40 promoter and the LMM is murine SCD1.

93. The method of embodiment 90, wherein the control sequence comprises an SV40 promoter and the LMM is SCD1, e.g., CHO SCD1.

94. The method of embodiment 90, wherein the control sequence comprises an SV40 promoter and the LMM is SREBF1, e.g., CHO SREBF1.

95. The method of embodiment 90, wherein the control sequence comprises an SV40 promoter and the LMM is SREB411, e.g., CHO SREB411.

96. The method of embodiment 90, wherein the control sequence comprises an mCMV promoter and the LMM is murine SCD1.

97. The method of embodiment 90, wherein the control sequence comprises an mCMV promoter and the LMM is SCD1, e.g., CHO SCD1.

98. The method of embodiment 90, wherein the control sequence comprises an mCMV promoter and the LMM is SREBF1, e.g., CHO SREBF1.

99. The method of embodiment 90, wherein the control sequence comprises an mCMV promoter and the LMM is SREB411, e.g., CHO SREB411.

100. The method of embodiment 90, wherein the control sequence comprises an hCMV promoter and the LMM is murine SCD1.

101. The method of embodiment 90, wherein the control sequence comprises an hCMV promoter and the LMM is SCD1, e.g., CHO SCD1.

102. The method of embodiment 90, wherein the control sequence comprises an hCMV promoter and the LMM is SREBF1, e.g., CHO SREBF1.

103. The method of embodiment 90, wherein the control sequence comprises an hCMV promoter and the LMM is SREB411, e.g., CHO SREB411.

104. The method of embodiment 90, wherein the control sequence comprises a PGK promoter and the LMM is murine SCD1.

105. The method of embodiment 90, wherein the control sequence comprises a PGK promoter and the LMM is SCD1, e.g., CHO SCD1.

106. The method of embodiment 90, wherein the control sequence comprises a PGK promoter and the LMM is SREBF1, e.g., CHO SREBF1.

107. The method of embodiment 90, wherein the control sequence comprises a PGK promoter and the LMM is SREB411, e.g., CHO SREB411.

108. The method of embodiment 88, wherein the control sequence controls the expression of an LMM and the media comprises an inhibitor of activity of the enzyme.

109. The method of embodiment 108, wherein the control sequence, LMM, and inhibitor (e.g., P5CS inhibitor) are as listed in any single row of Table 4.

110. The method of any one of embodiments 88-109, wherein the media comprises L-azetidine-2-carboxylic acid.

111. The method of any one of embodiments 88-110, wherein the media comprises 3,4-dehydro-L-proline.

112. The method of any one of embodiments 88-111, wherein the media comprises L-4-thiazolidinecarboxylic acid.

113. The method of any of the preceding embodiments, further comprising recovering the product of the subject nucleic acid sequence.

114. The method of any of the preceding embodiments, comprising recovering the product from media.

115. The method of any of the preceding embodiments, comprising recovering the product from the cell.

116. The method of any of the preceding embodiments, comprising:
  i) selecting a cell that grows on the media;
  ii) culturing the cell under a second set of culture conditions, e.g., on a second media, e.g., subjecting the selected cell to a second selection; and
  iii) recovering product from the cell or second media.

117. A method of identifying, selecting or culturing, a cell comprising a subject nucleic acid sequence, the method comprising:
  a) providing a cell comprising a nucleic acid, e.g., a vector, e.g., a replicable vector, comprising:
    (i) the subject nucleic acid sequence;
    (ii) a nucleic acid sequence that when expressed results in an elevated level of activity of an enzyme in the synthetic pathway of an amino acid, e.g., the proline synthetic pathway, e.g., a nucleic acid sequence that encodes an enzyme molecule that comprises the activity; and
  b) culturing the cell comprising the nucleic acid sequence in the presence of a first media having an insufficient level of the amino acid, e.g., proline, to support growth of a cell that is the same as the subject cell not having elevated activity, under conditions sufficient to allow for growth of a cell comprising the nucleic acid sequence (and the first media optionally comprising an inhibitor of the enzyme),
  c) culturing the cell comprising the nucleic acid sequence in the presence of a second media comprising an insufficient level of a second amino acid, e.g., tyrosine, to support growth of a cell that is the same as the subject cell not having elevated activity, under conditions sufficient to allow for growth of a cell comprising the nucleic acid sequence (and the second media optionally comprising an inhibitor of the second enzyme),
  thereby identifying, selecting or culturing, a cell comprising the heterologous nucleic acid sequence.

118. The method of embodiment 117, wherein step b is initiated prior to the initiation of step c.

119. The method of embodiment 117 or 118, wherein step b is performed prior to step c.

120. The method of embodiment 117 or 118, wherein step b and step c are performed concurrently.

121. The method of any one of embodiments 117-120, wherein step b and step c are performed in the same media.

122. The method of any one of embodiments 117-121, wherein step b and step c are performed in the same container.

123. The method of any one of embodiments 117-122, wherein the selection of step b and the selection of step c are performed in the same media and the media:
  (a) has an insufficient level of the amino acid, e.g., proline, to support growth of a cell that is the same as the subject cell not having elevated activity; and
  (b) has an insufficient level of the second amino acid, e.g., tyrosine, to support growth of a cell that is the same as the subject cell not having elevated activity of the second enzyme.

124. The method of any one of embodiments 117-123, wherein the cell further comprises:
  (iii) a nucleic acid sequence that when expressed results in an elevated level of activity of a second enzyme in a synthetic pathway of an amino acid, e.g., a nucleic acid sequence that encodes an enzyme molecule that comprises the activity.

125. The method of any of any one of embodiments 117-124, wherein the cells are cultured on media having an inhibitor of the activity of the enzyme.

126. The method of any of any one of embodiments 117-125, wherein the cells are cultured on media having an inhibitor of the activity of the second enzyme.

127. The method of any one of embodiments 117-126, wherein the second enzyme is in the same pathway, e.g., the proline synthetic pathway, as the enzyme of (ii).

128. The method of embodiment 127, wherein:
  the second enzyme is in a synthetic pathway of the same amino acid, e.g., a nucleic acid sequence that encodes an enzyme molecule that comprises the activity; and
  the media of b) further comprises:
    iv) an inhibitor of activity of the second enzyme.

129. The method of any one of embodiments 117-128, wherein the second enzyme is in a different pathway than the enzyme of (ii), e.g., the enzyme is in the proline synthetic pathway and the second enzyme is in a pathway other than proline, e.g., the tyrosine or tryptophan pathway.

130. The method of embodiment 129, wherein:
  the second enzyme is in a synthetic pathway of a second amino acid, e.g., a nucleic acid sequence that encodes an enzyme molecule that comprises the activity.
  the media of b) further comprises:
    iii) an insufficient level of the second amino acid, e.g., an amino acid other than proline, to support growth of a cell that is the same as the subject cell not having elevated activity; and
    iv) an inhibitor of activity of the second enzyme.

131. A cell comprising a sequence encoding a heterologous lipid metabolism modifier (LMM) operatively linked to a sequence comprising a control region, e.g., a promoter sequence, from any of an SV40 promoter sequence, an mCMV promoter sequence, or a PGK promoter sequence.

132. The cell of embodiment 131, wherein the LMM modulates a pathway listed in Table 2.

133. The cell of embodiment 131 or 132, wherein the LMM comprises steroyl-CoA desaturase-1 (SCD1).

134. The cell of embodiment 131 or 132, wherein the LMM comprises sterol regulatory element binding transcription factor 1 (SREBF1).

135. The cell of embodiment 131 or 132, wherein the LMM comprises a truncated isoform of SREBF1 (e.g., a truncated isoform of SREBF1 lacking the regulatory domains, e.g., SREB411).

136. The cell of any of the preceding embodiments, wherein the sequence encoding a heterologous lipid metabolism modifier (LMM) is disposed in a vector.

137. The cell of any of the preceding embodiments, wherein the vector further comprises a sequence encoding a selectable marker, e.g., a marker, which when present allows survival or growth on a defined media.

138. The cell of any of the preceding embodiments, wherein the vector further comprises a sequence encoding a selectable marker which when present allows survival or growth on media lacking a nutrient, e.g., an amino acid.

139. The cell of embodiment 138, wherein the nutrient is an amino acid, e.g., an amino acid selected from those listed in Table 1.

140. The cell of embodiment 139, wherein the nutrient comprises proline.

141. The method of any one of embodiments 137-140, wherein the marker comprises pyrroline-5-carboxylate synthase (P5CS) molecule.

142. The cell of any one of embodiments 138-141, wherein the nutrient comprises tyrosine.

143. The cell of any one of embodiments 138-142, wherein the nutrient comprises tryptophan.

144. The cell of any one of embodiments 131-143, wherein the marker is selected from Table 1.

145. The cell of any one of embodiments 137-144, wherein the marker comprises glutamine synthetase.

146. The cell of any preceding embodiment 131-145, wherein the sequence encoding the LMM is operatively linked to a sequence encoding an SV40 promoter sequence.

147. The cell of any preceding embodiment 131-145, wherein the sequence encoding the LMM is operatively linked to a sequence encoding an mCMV promoter sequence.

148. The cell of any preceding embodiment 131-145, wherein the sequence encoding the LMM is operatively linked to a sequence encoding a PGK promoter sequence.

149. The cell of any of embodiments 131-148, wherein the LMM is SCD1.

150. The cell of embodiment 149, wherein the LMM is murine SCD1.

151. The cell of embodiment 149, wherein the LMM is CHO SCD1.

152. The cell of any of embodiments 131-148, wherein the LMM is SREBF1.

153. The cell of any of embodiments 131-148, wherein the LMM is CHO SREBF1.

154. The cell of any of embodiments 131-148, wherein the LMM is SREB4l1.

155. The cell of any of embodiments 131-148, wherein the LMM is CHO SREB4l1.

156. The cell of any of embodiments 131-148, wherein the LMM comprises steroyl-CoA desaturase-1 (SCD1) and the promoter comprises an SV40 promoter sequence.

157. The cell of any of embodiments 131-148, wherein the LMM comprises steroyl-CoA desaturase-1 (SCD1) and the promoter comprises an mCMV promoter sequence.

158. The cell of any of embodiments 131-148, wherein the LMM comprises steroyl-CoA desaturase-1 (SCD1) and the promoter comprises an PGK promoter sequence.

159. The cell of any of embodiments 131-148, wherein the LMM comprises sterol regulatory element binding transcription factor 1 (SREBF1) and the promoter comprises an SV40 promoter sequence.

160. The cell of any of embodiments 131-148, wherein the LMM comprises sterol regulatory element binding transcription factor 1 (SREBF1) and the promoter comprises an mCMV promoter sequence.

161. The cell of any of embodiments 131-148, wherein the LMM comprises sterol regulatory element binding transcription factor 1 (SREBF1). and the promoter comprises a PGK promoter sequence.

162. The cell of any of embodiments 131-148, wherein the LMM comprises SREB4l1 and the promoter comprises an SV40 promoter sequence.

163. The cell of any of embodiments 131-148, wherein the LMM comprises SREB4l1 and the promoter comprises an mCMV promoter sequence.

164. The cell of any of embodiments 131-148, wherein the LMM comprises sterol SREB4l1 and the promoter comprises a PGK promoter sequence.

165. The cell of any of embodiments 131-148, wherein the media comprises an inhibitor as listed in Table 1 or 4.

166. The cell of any of embodiments 131-148, wherein the media comprises a P5CS inhibitor.

167. The cell of embodiment 166, wherein the P5CS inhibitor is L-azetidine-2-carboxylic acid.

168. The cell of embodiment 166, wherein the P5CS inhibitor is 3,4-dehydro-L-proline.

169. The cell of embodiment 166, wherein the P5CS inhibitor is L-4-thiazolidinecarboxylic acid.

EXEMPLIFICATION

Example 1: Investigating Pyrroline-5-Carboxylate Synthase Expression and Inhibitors for Use in a Proline Metabolism Mammalian Selection System Pyrroline-5-carboxylate synthase (P5CS) is the rate limiting enzyme responsible for proline synthesis from glutamate. A simplified illustration of this pathway is shown in FIG. 1. Since proline metabolism is integral for cell survival, cells cultured in media absent of proline should be unable to survive. Alternatively, those cells with abundant P5CS expression, and thus the capacity to efficiently generate proline from glutamate, should enable cell survival under these conditions thus facilitating appropriate selection of desired cells.

Figure 2:
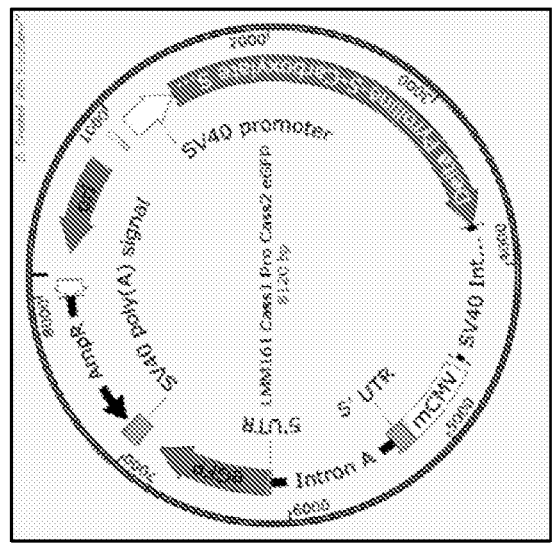
FIG. 2 is a diagram showing the plasmid map of an exemplary vector bearing the P5CS and eGFP genes.

In order to evaluate this hypothesis, a vector bearing the P5CS gene was first synthesized and cloned in order to generate a construct inclusive of this gene of interest and the eGFP reporter gene (FIG. 2). Upon transfection, this vector should induce P5CS expression levels beyond those endogenously observed in CHO cells allowing for high rates of proline synthesis and thus facilitating cell survival in the absence of external proline usually present in the media. In theory, those cells expressing abundant P5CS due to transfection of the construct should also express the eGFP gene.

While an over-expression of P5CS may be sufficient to select for cells in the absence of proline, inhibitors of this enzyme may improve the stringency of this system. Proline itself is an effective inhibitor of P5CS as it is part of an endogenous feedback loop in CHO cells. The inhibitors identified for use in this system include analogues of proline. Exemplary inhibitors are shown herein to be effective inhibitors of in vitro activity of P5CS.

Cell Growth in the Absence of Proline

In one experiment, cells engineered to knock out endogenous glutamine synthetase expression (GSKO cells) were cultured in the absence of proline in order to determine the effect that this had on growth. GSKO cells were seeded at $0.2 \times 10^6$ cells/ml in a total culture volume of 20 ml in 125 ml Erlenmeyer flasks. Cells were cultured using CD-CHO either with (6 mM Glut) or without L-glutamine (No Glut) or in CM76 medium without proline (No Pro) but with 6 mM L-glutamine. Viable cell counts and culture viability was measured every 24 hours using a ViCell instrument.

GSKO cells were unable to grow when cultured in the absence of proline (FIG. 3). However, cells cultured in the absence of L-glutamine showed a decrease in culture viability over time. This was expected since these cells have been engineered to knockout endogenous expression of glutamine synthetase, the rate-limiting enzyme in the production of glutamine.

Reversion Rate of Cells Cultured in the Absence of Proline

The number of revertant cells arising from cultures incubated in proline free media was determined to evaluate the suitability of exploiting proline metabolism for use in a selection system. Briefly, Lonza's GSKO cells were seeded in CD-CHO with 6 mM L-glutamine, CD-CHO without L-glutamine or CM76 with 6 mM L-glutamine and without proline at either 1,000 or 5,000 cells per well in a 96 well plate such that the culture volume equalled 200 μl per well. A total of 30 plates were seeded in each media where 15 were cultured at 1,000 cells per well and 15 were cultured at 5,000 cells per well. Revertant colonies were identified using microscopy observed after 11 days.

100% of wells seeded in CD CHO with 6 mM L-glutamine were confluent after 11 days whilst no revertant colonies were observed when cultured in medium absent of L-glutamine. Out of a total of $8.64\times10^6$ cells cultured in the absence of proline, 15 revertant colonies were observed with 13 observed in plates seeded with 5,000 cells per well and 2 colonies observed in plates seeded with 1,000 cells per well.

Overexpression of P5CS to Select for Cells Expressing a Gene of Interest

Figure 4C:
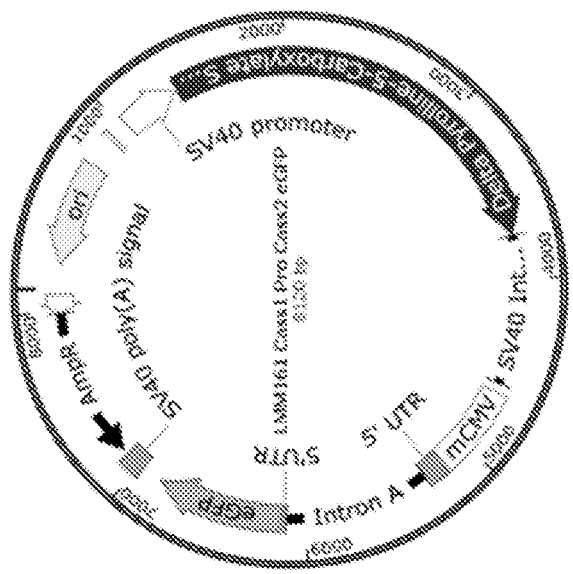
FIGS. 4A-4C are a series of graphs showing the plasmid maps for exemplary vectors comprising an Etanercept gene (FIG. 4A), glutamine synthetase (GS) and eGFP genes (FIG. 4B), or P5CS and eGFP genes (FIG. 4C).
Figure 4B:
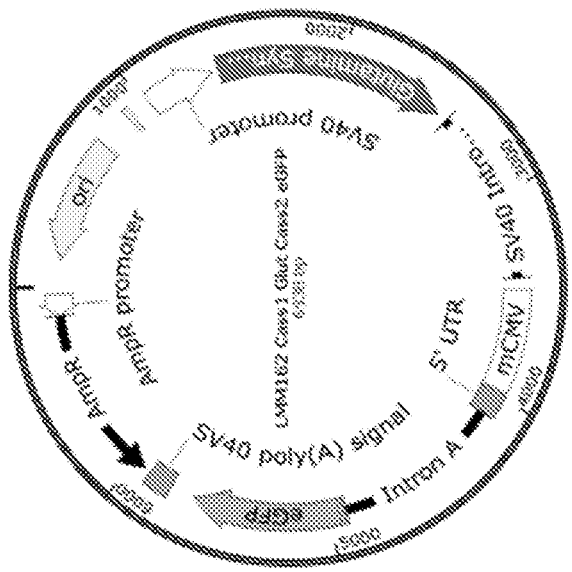
Figure 4A:
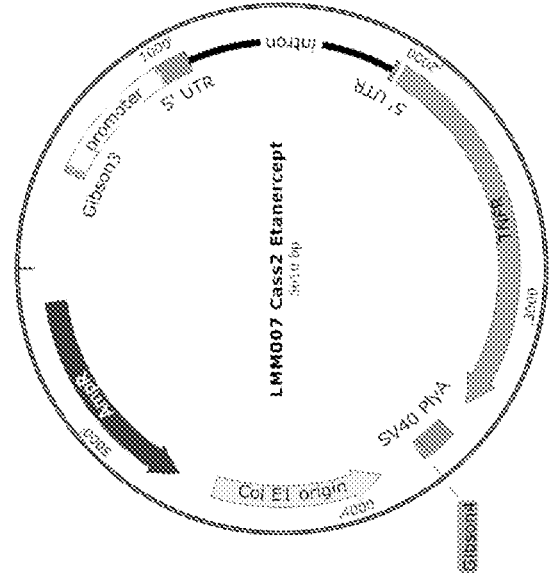

It was shown above that exclusion of proline from culture medium resulted in a lack of growth of GSKO cells. Overexpression of pyrroline-5-carboxylate synthase (P5CS), the rate limiting enzyme in endogenous proline synthesis, was hypothesized to be sufficient to recover growth in the absence of exogenous proline, thereby providing an efficient selection system. In order to evaluate this hypothesis, cells were transfected with plasmids bearing the P5CS gene to facilitate its overexpression and cultured in the absence of proline. Briefly, plasmids were constructed to include either glutamine synthetase (GS) or P5CS, as well as an eGFP reporter gene. A control vector that does not contain any "selection" gene or reporter was also included; it includes only of the Etanercept gene to induce similar cellular burden as other plasmids included in this experiment. Schematics of the vectors used are shown in FIG. 4. Plasmids constructed were transiently transfected into GSKO cells via electroporation and cultured in different medias; CD-CHO, CM76 medium without tyrosine or CM76 medium without proline (all of which were supplemented to include a final concentration of 6 mM L-glutamine). The total culture volume was 20 ml (originally seeded at $0.2\times10^6$ cells/ml) in a 125 ml Erlenmeyer flask at 37° C. shaking at 140 rpm and samples were taken for counts and analysis via flow cytometry at 72 and 168 hours post transfection.

FIG. 5 shows data obtained post-transfection of GSKO cells transiently transfected with vectors outlined in FIG. 4 and subsequently cultured in the specified medium. Cells cultured in either tyrosine free or proline free media show reduced growth rate at 72 hours post transfection compared to cells cultured in CD-CHO regardless of which plasmid was introduced (FIG. 5A). This observation is consistent with patterns outlined above. However, an increased viable cell concentration was observed at 168 hours post transfection with the P5CS containing vector in the proline free medium compared to when any other vector was used. Furthermore, the introduction of this vector did not result in increased viable cell numbers achieved in tyrosine free medium suggesting that P5CS was able to compensate specifically for the absence of exogenous proline.

Despite the observable differences in viable cell concentrations, culture viability was not significantly affected in general upon culturing in different media (FIG. 5B). It is noteworthy that transfection with the P5CS containing construct followed by subsequent culture at 72 hours was lower than values obtained with alternate transfections cultured in the same medium. It is possible that this was due to additional cellular burden placed upon these cells due to increased proline synthesis in addition to a lack of tyrosine available. This trend was not observed at the 168 hour time point. The viability of cells cultured in CD-CHO was generally lower at the 168 hour time point but this was likely due to typical growth profiles of these cells, which are expected to be in decline phase at this time point in contrast to cells cultured in other media which have not followed typical growth trends.

Figure 5C:
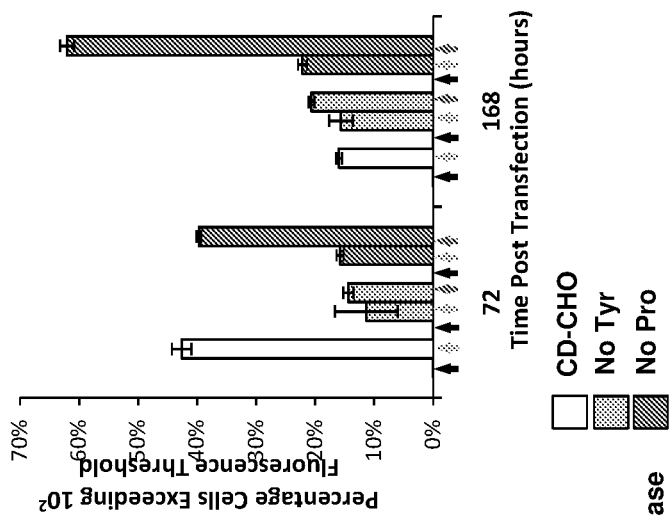
Figure 5D:
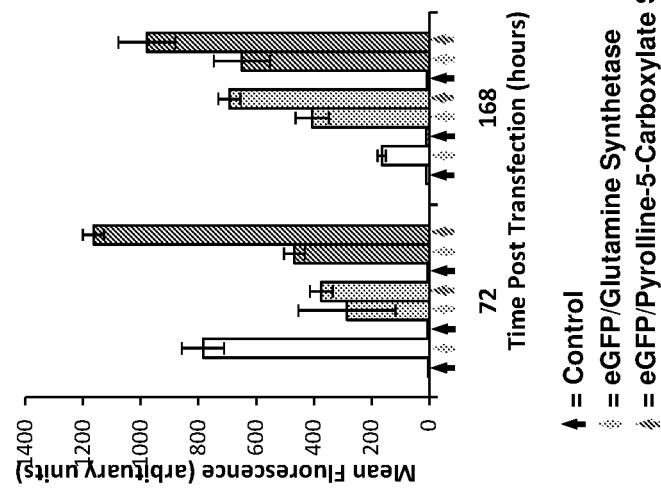

Analysis using flow cytometry showed that the combination of transfection with the P5CS containing plasmid and subsequent culture in proline free medium resulted in the highest mean fluorescence out of the conditions measured across both time points (FIG. 5C). Generally, cells cultured in the absence of proline showed higher mean fluorescence values than those cultured without exogenous tyrosine and inclusion of P5CS on the transient plasmid and subsequent culture in tyrosine free media showed higher mean fluorescence than when GS was included instead, which suggests that overexpression of P5CS may have a broad effect on increasing eGFP expression. However, it is evident that the combination of P5CS overexpression has a more profound effect on cells subsequently cultured in proline free medium confirmed by the vast increase in mean fluorescence values and reinforced by vastly increased values observed in the percentage of cells exceeding a predetermined fluorescence intensity threshold (FIG. 5D).

These data collectively support the hypothesis that arrested cell growth observed when GSKO cells are cultured in the absence of proline can be recovered through the overexpression of the P5CS gene. Furthermore, this can have a significant effect on the expression of a reporter gene in terms of both overall expression but also the percentage of cells expressing the reporter gene in a transient population.

Generation of Stable Cell Pools Expressing a Gene of Interest

In order to assess the capacity of the proline/P5CS system to generate recombinant cell pools, vectors comprising the P5CS gene and a gene of interest were transfected into cells and subsequently cultured in the absence of proline in an attempt to generate recombinant cell pools. Briefly, $1\times10^7$ Lonza's GSKO cells were electroporated with 20 µg plasmid which was first linearized using PvuI restriction enzyme (NEB) and purified using sodium acetate and ethanol precipitation. The construct used contained both the P5CS gene for evaluation as a selection marker and eGFP as a reporter gene. Transfections were carried out in CM76 medium in the absence of proline but supplemented with L-glutamine to achieve a final concentration of 6 mM. The cells were then cultured in 25 ml of this medium in a T75 flask for 10 days before being transferred to 10 ml suspension culture, also in proline absent medium. The resulting pool was analyzed using flow cytometry. Cell samples were first centrifuged at 1,000 rpm for 5 minutes and resuspended in 500 µl PBS. Samples were then loaded onto the probe of a FACScalibur™ (BD biosciences) and fluorescence intensity was measured in relation to the cell count. The forward scatter (FSC) was measure using the E-1 amplifier and side scatter (SSC) set to 465 whilst FL1 recorded cells at 473; all settings were converted to Log scales. In order to facilitate the adherence of suspension cells, coverslips were first submerged in poly-L-lysine and incubated for 15 minutes at room temperature. Coverslips were then removed and left to dry in a sterile environment before transferring to a 24 well plate. Cells were cultured at 37° C. overnight to facilitate adhering of cells to the coverslip before aspirating the medium and adding 250 µl of 4% paraformaldehyde in PBS and incubating for 20 minutes at 37° C. to fix cells. Subsequently two 1 ml PBS washes were carried out before 250 µl 0.1% triton X100 in PBS was added and incubated for 5 minutes at room temperature to permeablize cells. Fixed and permeablized cells were blocked by adding 250 µl 3% BSA in PBS per well and incubated at room temperature for 30 minutes. This was aspirated and the coverslips were levered out of the wells and placed face down on a previously prepared drop of 100 µl PBS which was repeated a further three times. The coverslips were dried by touching the edge to a tissue and transferred to a 25 μl drop of the appropriate primary antibody. This was left to incubate at 4° C. overnight. The appropriate secondary antibody was diluted accordingly in 3% BSA in PBS. Coverslips were placed face down onto 100 μl drops of 0.1% Tween in PBS and left for 5 minutes. These were then transferred to fresh drops four times and left for 10 minutes between the last two transfers. They were then placed on 25 μl secondary antibody drops and left for 2 hours and left to in the dark at 4° C. Five final washes were undertaken using 5 sequential 100 μl drops. Where DAPI staining was required, coverslips were each transferred to a 50 μl drop of DAPI at 10 mg/ml between the second and third PBS drops. Finally, cells were mounted on cell slides using ProLong Gold antifade mountant (Thermo-Scientific) and left overnight to set. Images were collected using a Zeiss confocal microscope. The flow cytometer instrument was calibrated such that host cells did not exceed $10^1$ fluorescence intensity value thus those cells exceeding this predetermined threshold are considered to be expressing eGFP.

Figure 6A:
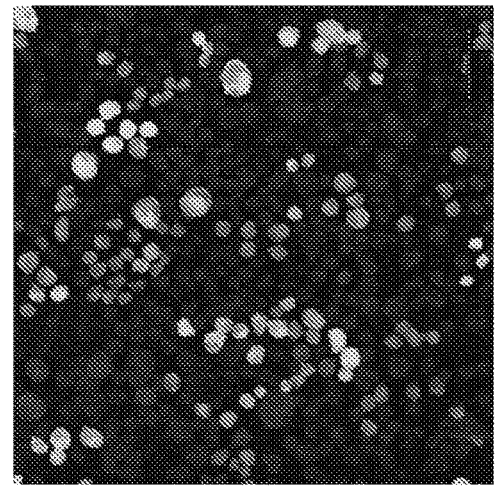
FIGS. 6A-6C are a series of diagrams showing analysis of cell pools generated using P5CS overexpression and cultured in the absence of proline.
Figure 6B:
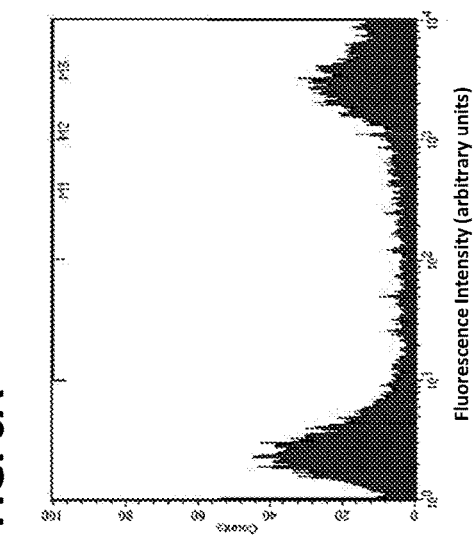

FIG. 6A shows a histogram obtained from the pool generated using the P5CS based selection system using flow cytometry. Since many cells have a fluorescence intensity above the $10^1$ threshold, it is evident that the P5CS selection system is able to select for cells expressing a gene of interest. However, a population of cells with fluorescence intensity values below $10^1$ is present which suggests that non-expressing cells are still present in the pool. It may be important to increase the stringency of the system. FIG. 6B shows an image of the synthesized pool obtained using fluorescence microscopy. This image supports the data shown in FIG. 6A since populations of cells are present with varying eGFP expression levels and not all cells present necessarily express the eGFP reporter gene.

Figure 6C:
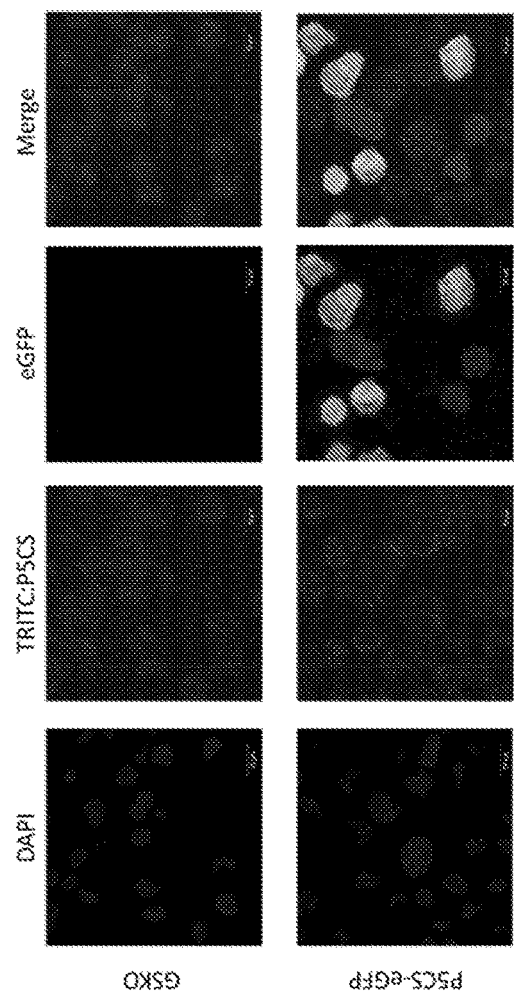

Both FIGS. 6B and 6C show the expression patterns of the P5CS genes. These images show punctate spots consistent with localization of P5CS in the mitochondria which has previously been reported in literature. Furthermore, FIG. 6C shows a comparison of the P5CS/eGFP pool with the GSKO host. Images show that the selected pool has higher expression levels of P5CS than the host but this observation is not exclusive to those cells expressing the eGFP reporter gene. Since it was shown that a fraction of host cells were able to revert in the absence of proline, it is possible that cells which do not contain the transfected vector were able to survive the selection process outlined without the need for overexpression of P5CS. Perhaps the absence of proline also selects for cells which endogenously express ample P5CS.

Figure 7:
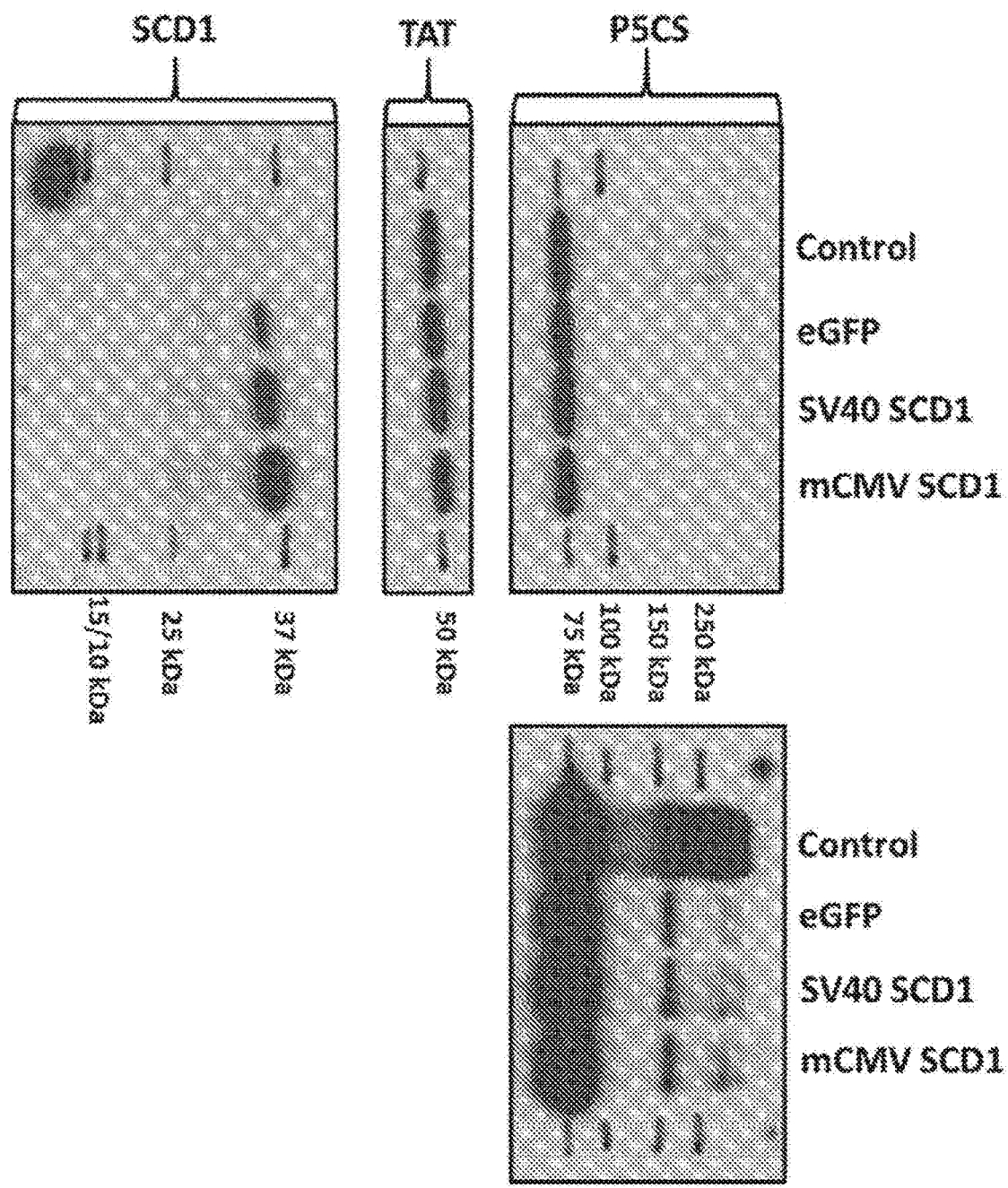
FIG. 7 is a series of western blot images showing analysis of cell pools generated using P5CS overexpression and cultured in the absence of proline. The vectors used for cell pool construction also contained either the eGFP gene (eGFP), the SCD1 gene where expression is driven by the SV40 promoter (SV40 SCD1) or the SCD1 gene where expression is driven by the mCMV promoter (mCMV SCD1). Western blot analysis was carried out to identify expression of P5CS, TAT, and SCD1 (the gene of interest).

Cell pools constructed using the P5CS system were examined by western blot analysis of lysate samples taken from the cell pools. The vectors used to generate these pools all contained the gene for P5CS and one of either eGFP or SCD1 (driven by either the SV40 or mCMV promoter), as labeled, and the control sample was constructed using a vector containing P5CS alone. GSKO cells were transfected via electroporation with the aforementioned linearized vectors and subsequently cultured in the absence of proline for two weeks before transferring to suspension cultures. As shown in FIG. 7, western blots of lysates from the resulting cell pools showed that SCD1 was overexpressed in the relevant cell pools (SV40 SCD1 and mCMV SCD1), compared to the eGFP and null controls showing that the P5CS system was suitable for cell line construction processes. In addition, a control vector lacking the P5CS gene was also transfected but the resulting cells did not grow in the absence of proline, showing that the overexpression of P5CS is crucial for their survival.

Figure 8C:
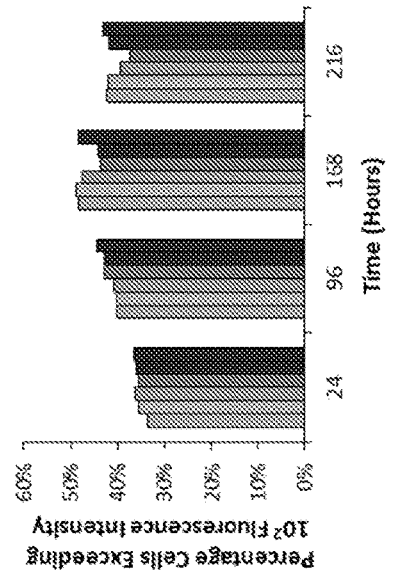
Figure 8D:
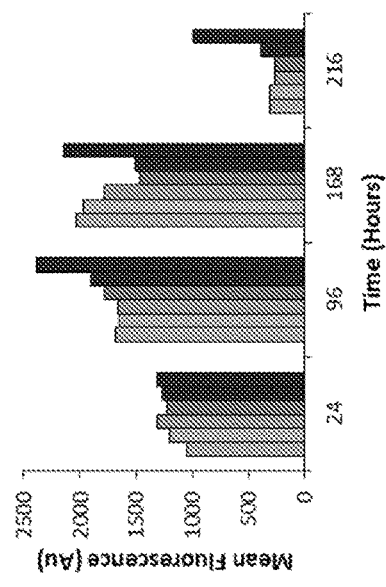
Figure 8E:
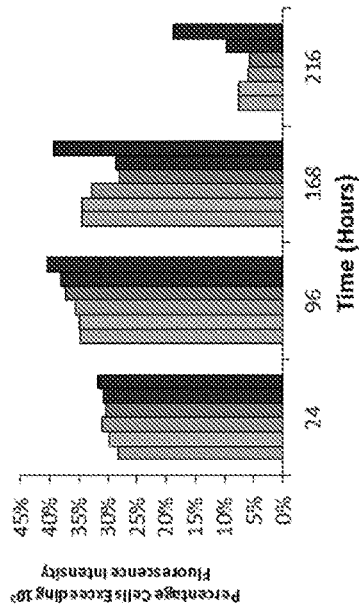
Figure 8F:
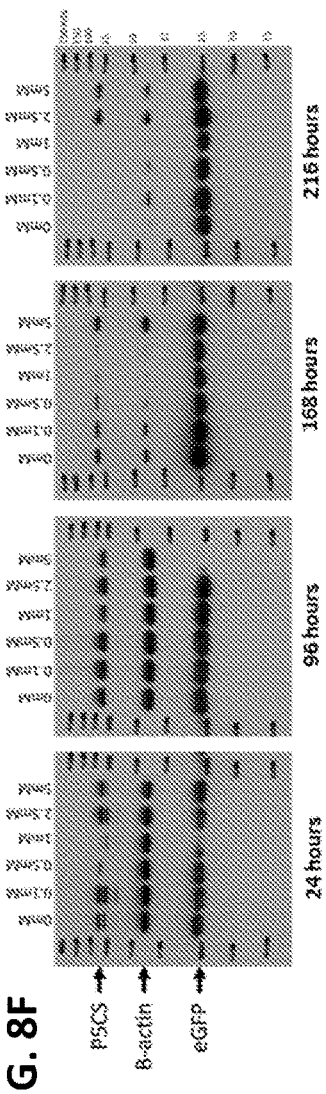

Cell Pools Grown in the Presence of P5CS Inhibitors
Cell Pools Grown in 96 Deep Well Plates Data was obtained from cell pools constructed using the P5CS/eGFP vector (as outlined above) when cultured in media lacking proline but supplemented with different concentrations of the P5CS inhibitor L-azetidine-2-carboxylic acid. Cells were cultured in 96 deep well plates and seeded at $0.2 \times 10^6$ cells/ml in suspension. Viable cell number (FIG. 8A), culture viability (FIG. 8B), mean fluorescence (FIG. 8C), cells expressing beyond a $10^2$ predetermined fluorescence threshold (FIG. 8D) and cells expressing beyond a $10^3$ predetermined fluorescence threshold (FIG. 8E) were all determined at 24, 96, 168 and 216 hours of culture. While an increase in inhibitor concentration resulted in slower cell growth, higher mean fluorescence was also observed showing that the addition of the inhibitor was able to enrich eGFP expression from an existing polyclonal population. FIG. 8F shows western blot analysis from lysate samples taken at the same time points. Blots were probed to highlight P5CS, β-actin and eGFP.

Figures 9A, 9B:
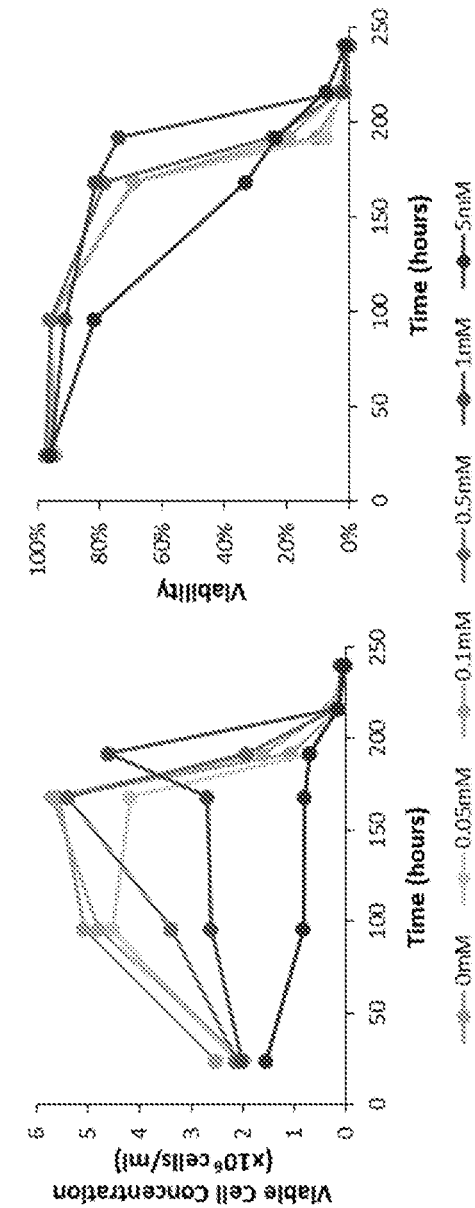

Data was obtained from cell pools constructed using the P5CS/eGFP vector (as outlined above) when cultured in media lacking proline but supplemented with different concentrations of the P5CS inhibitor 3,4-dehydro-L-proline. Cells were cultured in 96 deep well plates and seeded at $0.2 \times 10^6$ cells/ml in suspension. Viable cell number (FIG. 9A), culture viability (FIG. 9B), mean fluorescence (FIG. 9C), cells expressing beyond a $10^2$ predetermined fluorescence threshold (FIG. 9D) and cells expressing beyond a $10^3$ predetermined fluorescence threshold (FIG. 9E) were all determined at 24, 96, 168 and 216 hours of culture. While an increase in inhibitor concentration resulted in slower cell growth, higher mean fluorescence was also observed showing that the addition of the inhibitor was able to enrich eGFP expression from an existing polyclonal population. FIG. 9F shows western blot analysis from lysate samples taken at the same time points. Blots were probed to highlight P5CS, β-actin and eGFP.

Figure 10C:
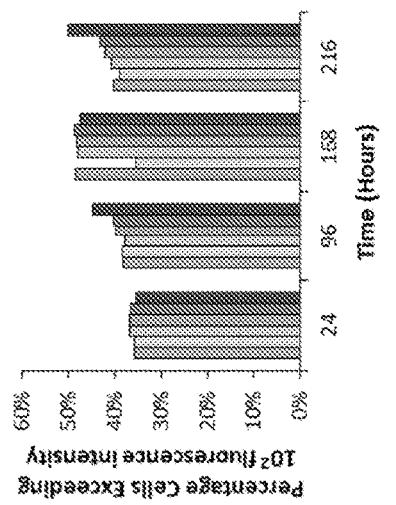
Figure 10D:
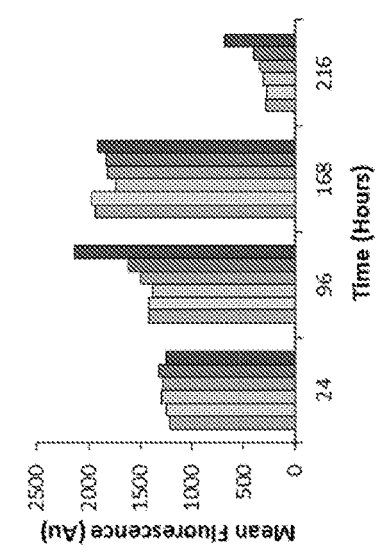
Figure 10E:
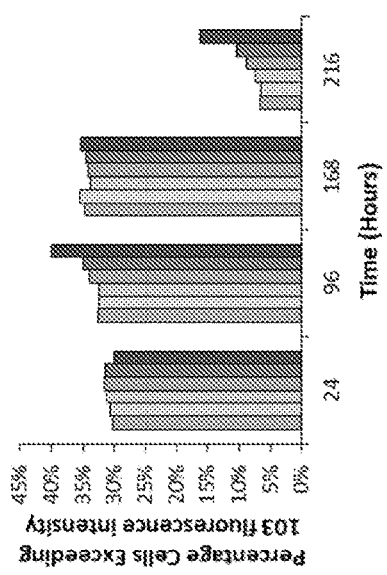
Figure 10F:
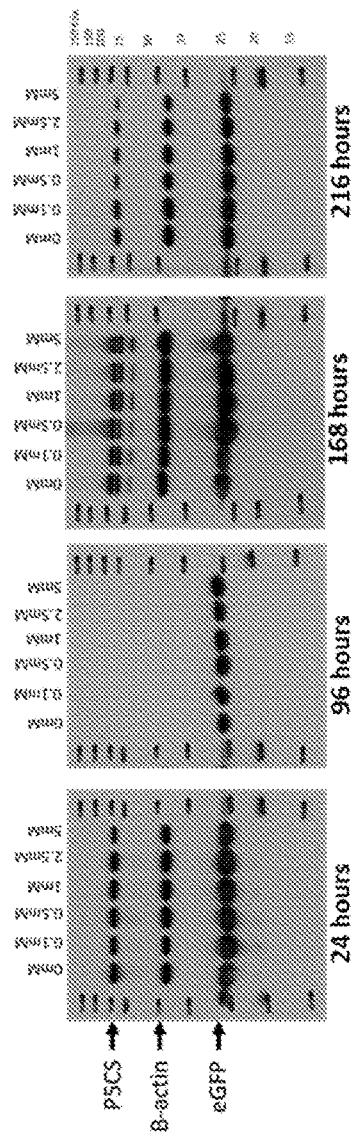

Data was obtained from cell pools constructed using the P5CS/eGFP vector (as outlined above) when cultured in media lacking proline but supplemented with different concentrations of the P5CS inhibitor L-4-thiazolidinecarboxylic acid. Cells were cultured in 96 deep well plates and seeded at $0.2 \times 10^6$ cells/ml in suspension. Viable cell number (FIG. 10A), culture viability (FIG. 10B), mean fluorescence (FIG. 10C), cells expressing beyond a $10^2$ predetermined fluorescence threshold (FIG. 10D) and cells expressing beyond a $10^3$ predetermined fluorescence threshold (FIG. 10E) were all determined at 24, 96, 168 and 216 hours of culture. While an increase in inhibitor concentration resulted in slower cell growth, higher mean fluorescence was also observed showing that the addition of the inhibitor was able to enrich eGFP expression from an existing polyclonal population. FIG. 10F shows western blot analysis from lysate samples taken at the same time points. Blots were probed to highlight P5CS, β-actin and eGFP.

Cell Pools Grown in 24 Well Plates

Figure 11B:
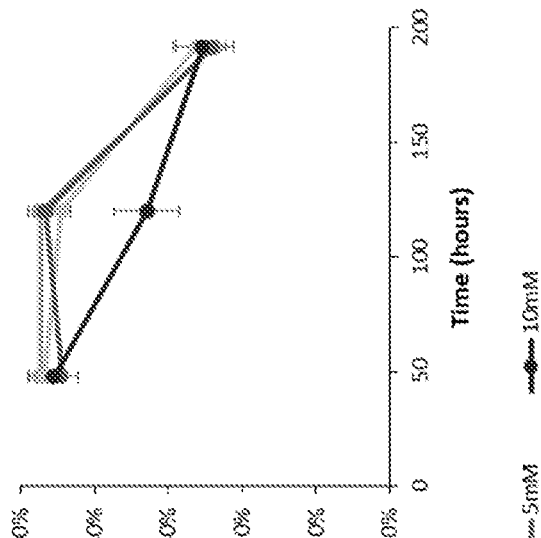
Figure 11A:
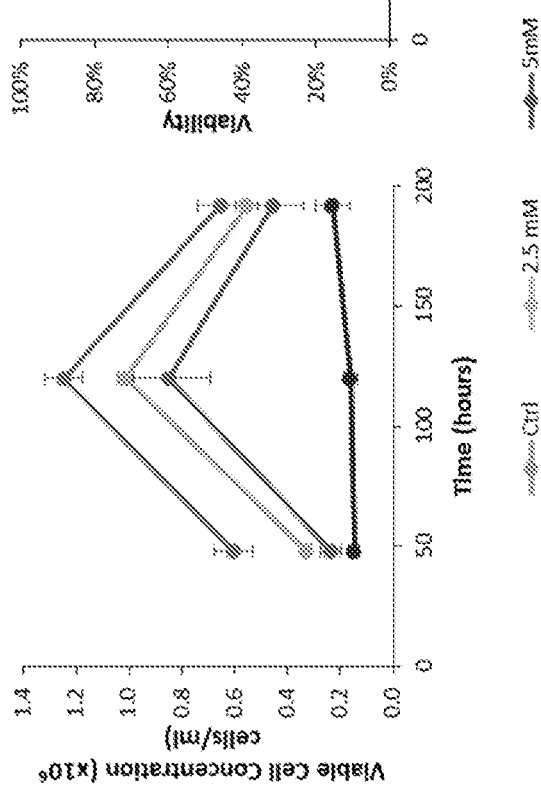

Data was obtained from cell pools constructed using the P5CS/eGFP vector (as outlined above) when cultured in media lacking proline but supplemented with different concentrations of the P5CS inhibitor L-azetidine-2-carboxylic acid. Cells were cultured in static 24 well plates and initially seeded at $0.2 \times 10^6$ cells/ml. Viable cell number (FIG. 11A), culture viability (FIG. 11B), mean fluorescence (FIG. 11C), cells expressing beyond a $10^2$ predetermined fluorescence threshold (FIG. 11D) and cells expressing beyond a $10^3$ predetermined fluorescence threshold (FIG. 11E) were all determined at 24, 96, 168 and 216 hours of culture. While an increase in inhibitor concentration resulted in slower cell growth, higher mean fluorescence was also observed showing that the addition of the inhibitor was able to enrich eGFP expression from an existing polyclonal population.

Figures 12A, 12B:
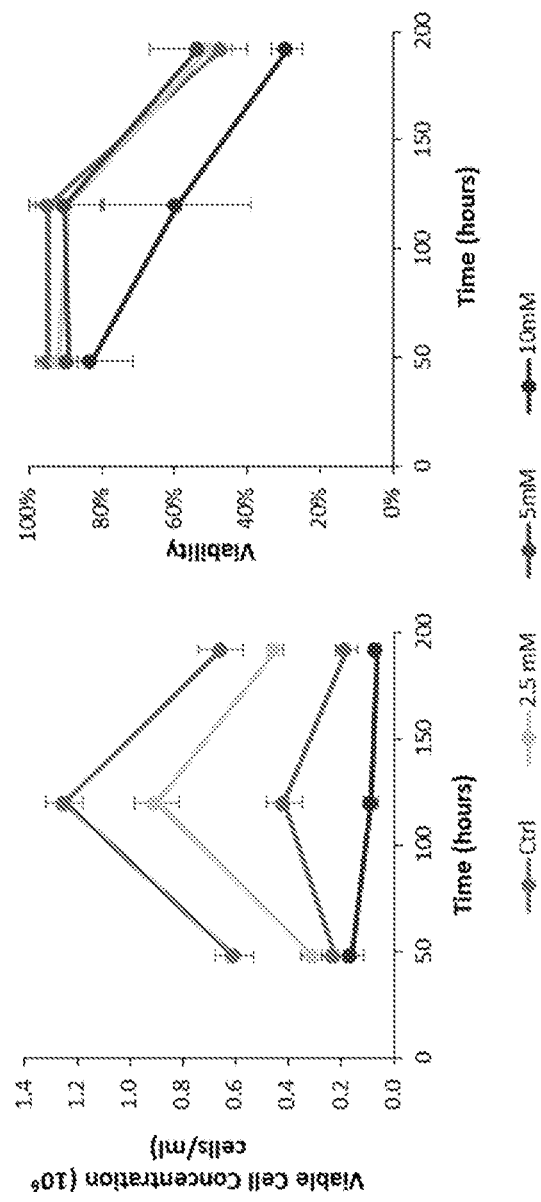

Data was obtained from cell pools constructed using the P5CS/eGFP vector (as outlined above) when cultured in media lacking proline but supplemented with different concentrations of the P5CS inhibitor3,4-dehydro-L-proline. Cells were cultured in static 24 well plates and initially seeded at $0.2 \times 10^6$ cells/ml. Viable cell number (FIG. 12A), culture viability (FIG. 12B), mean fluorescence (FIG. 12C), cells expressing beyond a $10^2$ predetermined fluorescence threshold (FIG. 12D) and cells expressing beyond a $10^3$ predetermined fluorescence threshold (FIG. 12E) were all determined at 24, 96, 168 and 216 hours of culture. While an increase in inhibitor concentration resulted in slower cell growth, higher mean fluorescence was also observed showing that the addition of the inhibitor was able to enrich eGFP expression from an existing polyclonal population.

Example 2: Lipid Metabolism Modifiers for Improving Host Cell Production of Antibodies Manipulation of lipid metabolism modifiers (LMMs) stearoyl-CoA desaturease-1 (SCD1), sterol regulatory element binding transcription factor 1 (SREBF1), and a truncated SREBF1 isoform, SREB411, comprising the portion of SREBF1 that migrates to the nucleus and lacking the regulatory domains of SREBF1, have been shown to improve CHOK1SV GS-KO host production and product quality of complex proteins and standard mAbs.

It was hypothesized that if the expression of these LMMs was modified in CHOK1SV GS-KO hosts in an industrial cGMP manner that it would result in a significant improvement in product titre and quality. The goal is to insert the desired LMM gene into an existing cell line or be able to create a new host cell line expressing one of the LLM genes with the commercial GS selection system intact.

To reach this goal and test the hypothesis the level of expression, and which of the LMM genes would be most applicable had to be determined. To this end several vectors were produced (Table 9): four vectors (A-D) expressing a recombinant protein and the GS selection marker, and ten (1-10) expressing a specific promoter+LMM gene combination.

TABLE 9

Vectors used to generate proof of concept cell pools which will contain a recombinant molecule and overexpress an LMM.

| Vector | Selection | Recombinant Molecule |
| --- | --- | --- |
| A | Glutamine Synthetase | B72.3 |
| B | Glutamine Synthetase | Infliximab |
| C | Glutamine Synthetase | Cergutuzumab |
| D | Glutamine Synthetase | Etanercept |

| Vector | Promoter | Lipid Metabolism Modifier (LMM) |
| --- | --- | --- |
| 1 | SV40 | SCD1 |
| 2 | SV40 | SREBF1 (CHO) |
| 3 | SV40 | SREB411 (CHO) |
| 4 | mCMV | SCD1 |
| 5 | mCMV | SREBF1 (CHO) |
| 6 | mCMV | SREB411 (CHO) |
| 7 | PGK | SCD1 |
| 8 | PGK | SREBF1 (CHO) |
| 9 | PGK | SREB411 (CHO) |
| 10 | mCMV | N/A |

All combinations of these vectors would then be screened by co-transfecting one recombinant molecule vector plus one promoter+LMM gene vector. Transfection was undertaken using the 4D-Nulcofector (Lonza) following the standard protocol; this would produce 96 replicate cultures per a condition (co-transfection). These replicate pools of transfected cells would then be assessed for cellular growth during culture and recombinant protein production in fed-batch conditions. These data would then be analyzed to determine which promoter+LMM combinations would make suitable candidates for further analysis and/or cell line construction.

Growth and Transfection of GSKO Cells

GS-KO CHO cells were cultured in CD-CHO+6 mM L-Glutamine. Every 4 days, the cultures were subcultured; 0.6 ml of each parent culture was counted using a Vicell-XR machine, recording 50 images per a culture. The daughter cultures were seeded at $0.2 \times 10^6$ viable cells/ml; cultures were then gassed with 5% CO2 and incubated at 36.5° C., 140 rpm.

On day 2 or 3 of subculture, GS-KO cells were counted using a ViCell-XR; a volume equal to $2 \times 10^7$ viable cells/ml was then taken and spun at 100 g for 10 minutes. After centrifugation, the supernatant was discarded via pipetting and the pellet re-suspended in 200 µl SF solution (provided with the 4D-nucleofector kit). The desired vectors from transfection were then added to the 200 µl cells/SF suspension at volumes to give 6 ug per a vector (LMM vector and recombinant protein). The DNA/cells/SF suspension was then split in equally in half and pipetted into a 4D nucleofector cuvette with care not to cause the formation of any bubbles in the cuvette. The volumes added to the cuvettes depended upon the total volume after addition of DNA vectors (usually between 103-108 µl).

Cuvettes were then placed into the 4D-nuclefector and pulsed using the pulse code DU158. If both pulses failed (denoted by a red '−', on the display) a new volume of $2 \times 10^7$ cells was taken and the method re-started. When pulse passed (denoted by a green '+', on the display), ~500 µl of pre-warmed (37° C.) 40 ml transfection medium (40 ml CD-CHO, 0.4 ml SP4, 0.04 ml concentrated (×1000) phenol red) was pipetted into the cuvette and the entire volume of culture was then transferred to the 40 ml of transfection medium; a pasture pipette was then used to 'flush' any residual cells from the cuvette using the transfection medium. The transfectant cell culture was then transferred to two 96 well plates (100 µl culture per a well) and incubated overnight at 36.5° C., 10% CO$_2$.

On day 1 post transfection, 100 µl per a well of transfection medium+100 µM MSX was added to each plate of transfected cultures. Plates/Cultures were then incubated at 36.5° C., 10% CO$_2$ for 6 days. On day 7 post transfection, 150 µl per a well/culture was carefully removed from each plate of transfected cultures and fresh transfection medium+ 50 µM MSX was added to each well/culture. Cultures were then monitored for recovery post transfection.

Cellular recovery post transfection was observed from around 10 days post transfection. This was done by observing the color of the transfection medium as well as using cloning mirrors to assess the confluence of each well by visual inspection. Well bottoms would appear opaque were cells had grown and the phenol red in the transfection medium would turn yellow upon production of lactic acid, which was used as an indicator of cellular growth. Once >75% of cultures were considered to be >75-80% confluent, the cultures in the plate were considered to be recovered and transferred to deep well plates.

Figure 13:
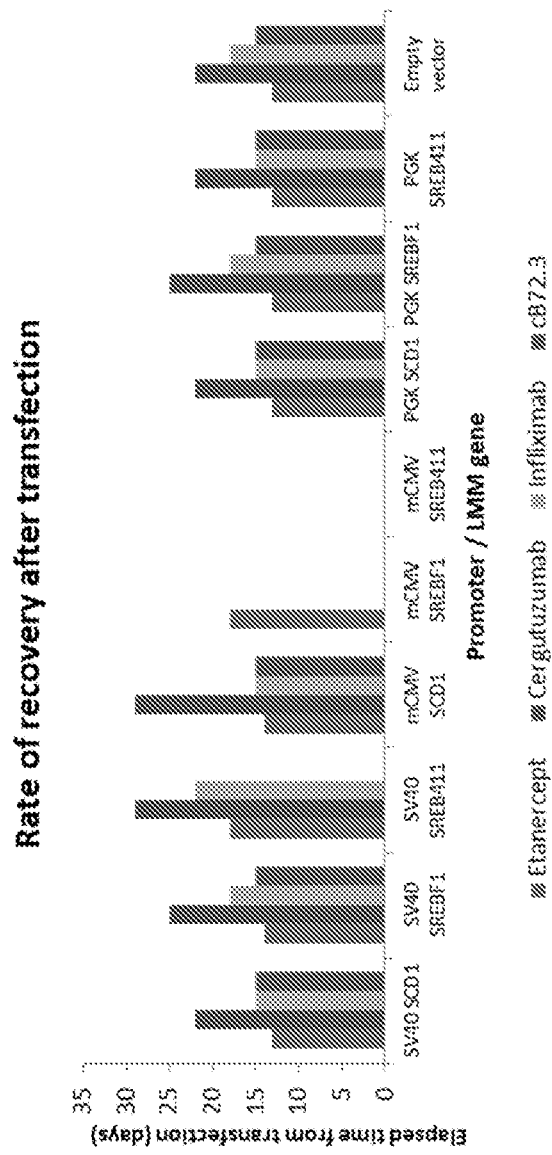
FIG. 13 is a diagram showing the rate of recovery, in days, of cultures co-transfected with an exemplary vector carrying the indicated lipid metabolism modifier (LMM) gene (SCD1, SREBF1, or SREB411) under the control of the indicated promoter (SV40, mCMV, or PGK promoter) and a second exemplary vector carrying a gene encoding the indicated recombinant protein of interest (Etanercept, Cergutuzumab, Infliximab, or cB72.3).
Figure 14A:
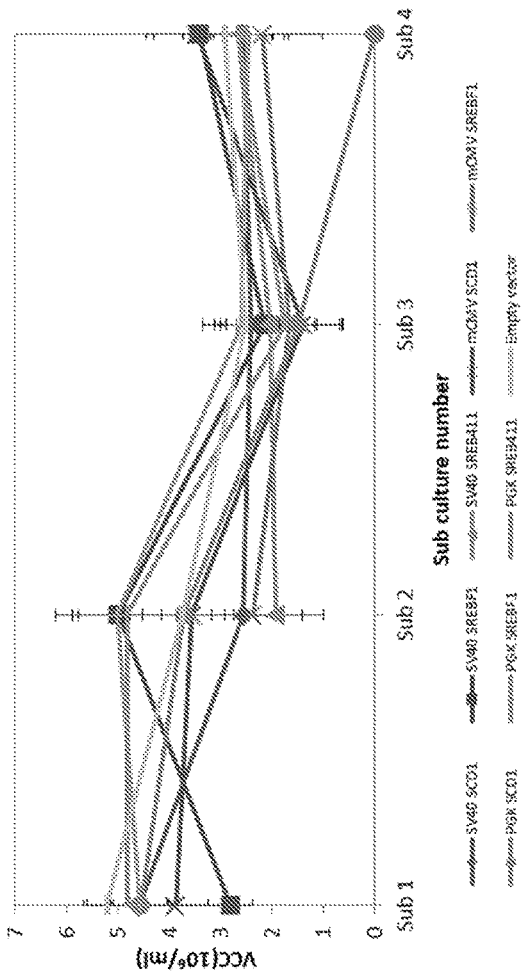
FIGS. 14A-14D are a series of graphs showing average viable cell concentration (VCC) at $10^6$/ml of cells transfected with the indicated LMM gene under the control of the indicated promoter and a gene encoding Etanercept (FIG. 14A), Cergutuzumab (FIG. 14B), Infliximab (FIG. 14C), or cB72.3 (FIG. 14D). Cell cultures were grown in deep well plates, and VCC was measured via Celigo cell counting of each culture/well.
Figure 14B:
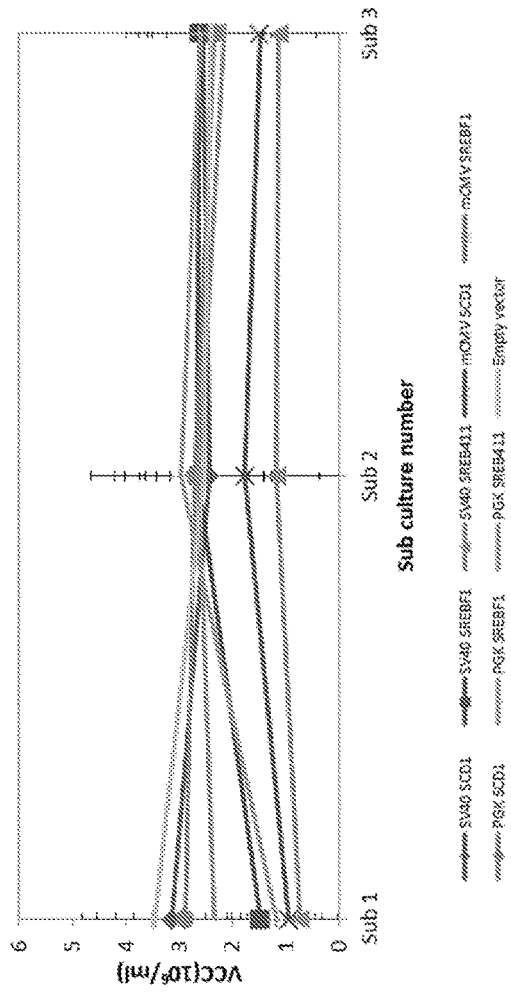
Figure 14C:
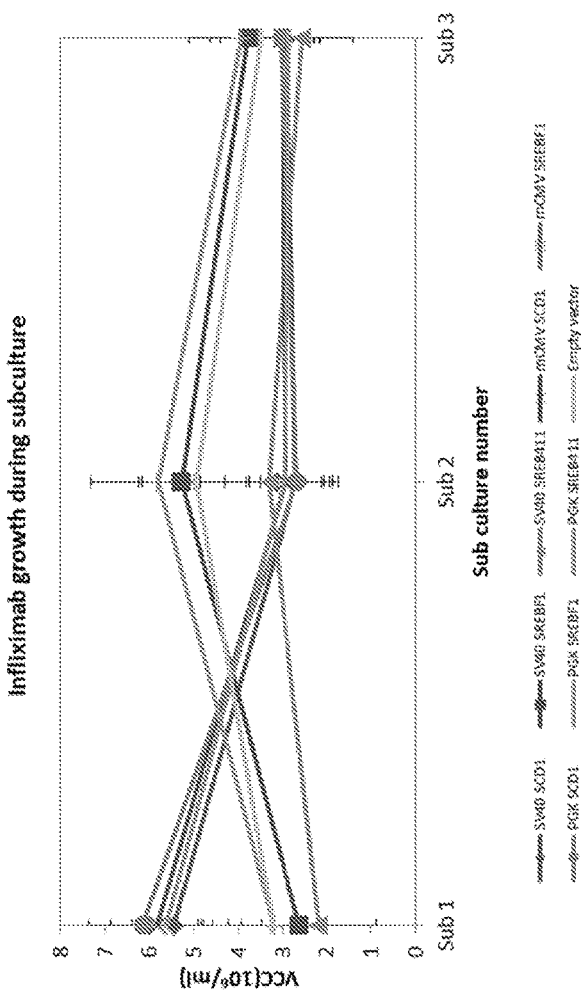
Figure 14D:
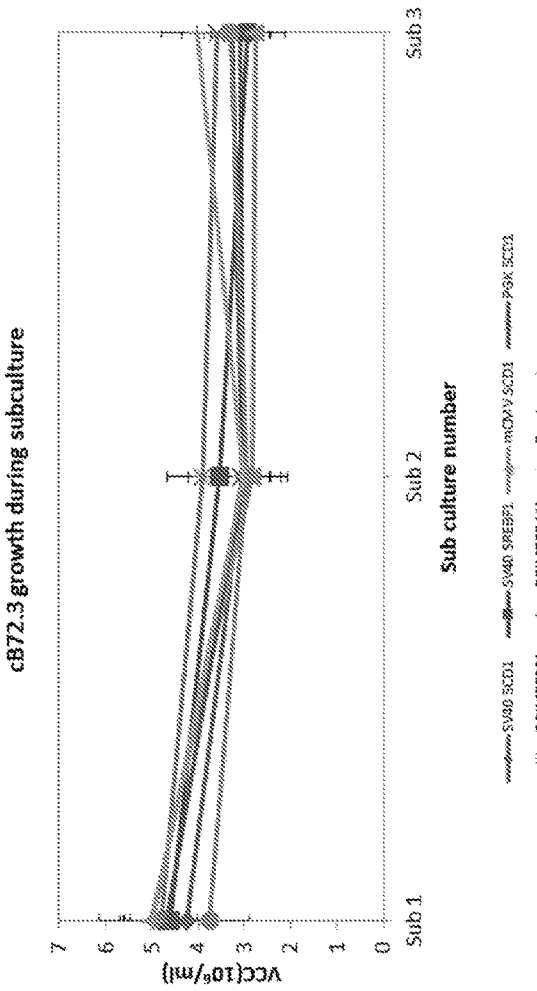
Figure 15A:
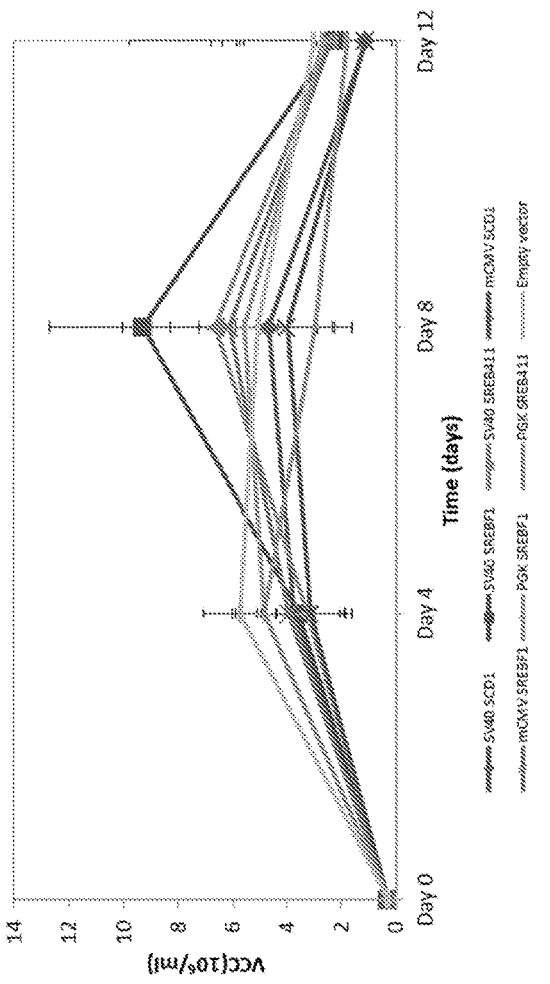
FIGS. 15A-15D are a series of graphs showing average viable cell concentration (VCC) at $10^6$/ml of cells during abridged fed-batch overgrow (aFOG). Cells were transfected with the indicated LMM gene under the control of the indicated promoter and a gene encoding Etanercept (FIG. 15A), Cergutuzumab (FIG. 15B), Infliximab (FIG. 15C), or cB72.3 (FIG. 15D). Cell cultures were grown in deep well plates, and VCC was measured via Celigo cell counting of each culture/well.
Figure 15B:
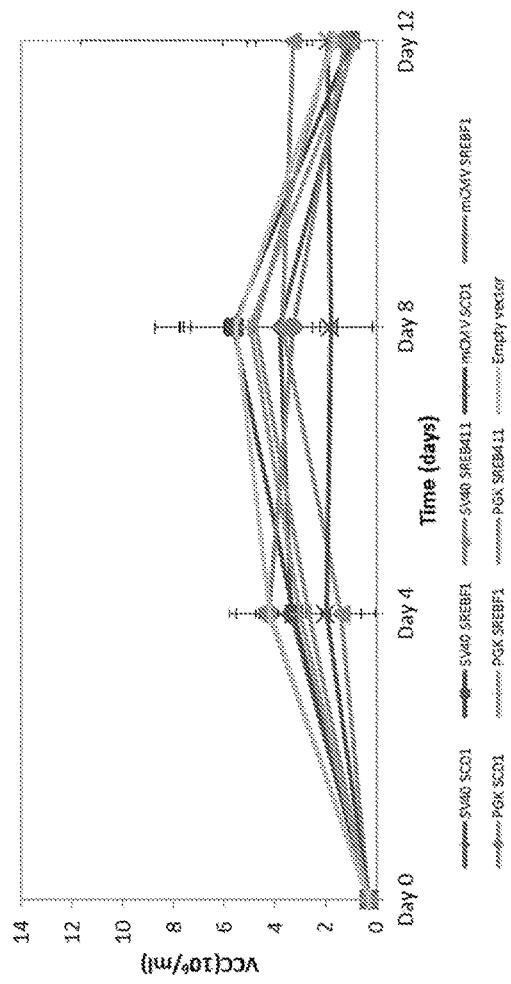
Figure 15C:
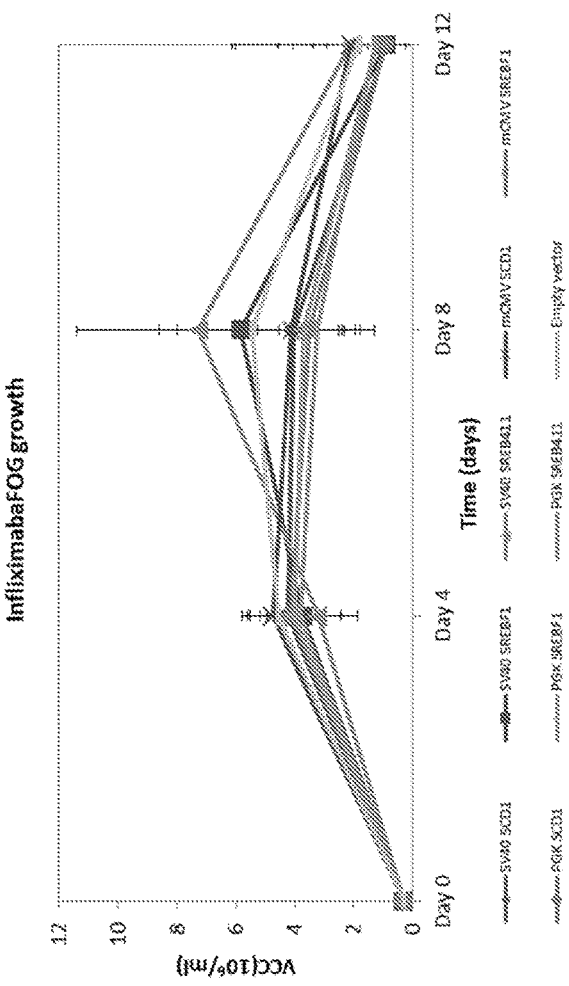
Figure 15D:
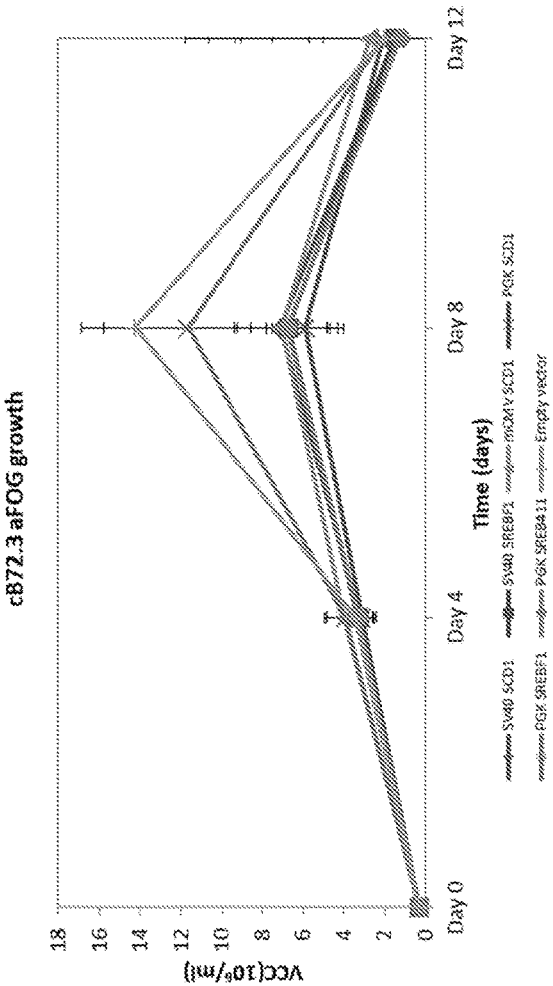
Figure 16C:
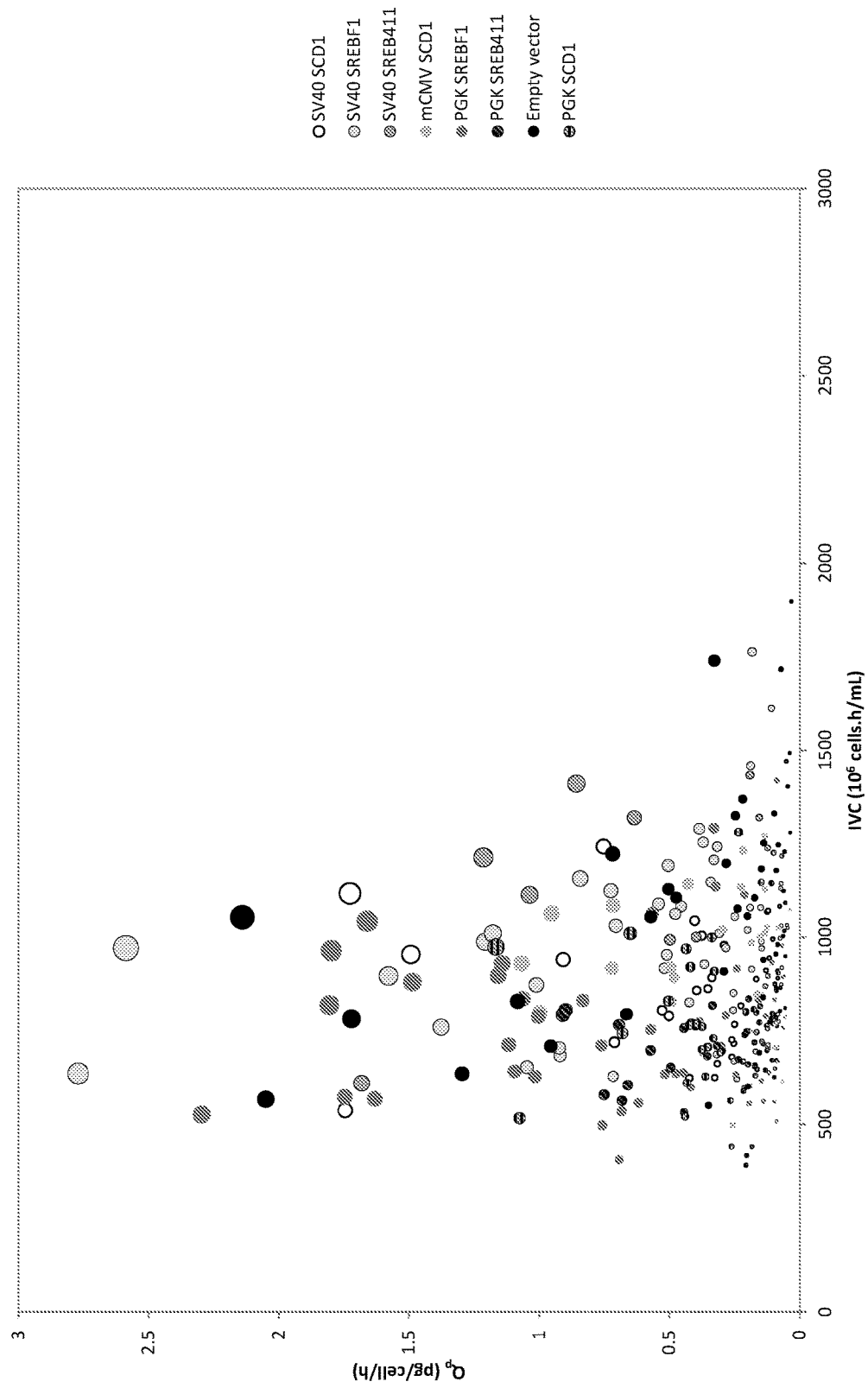
Figure 17A:
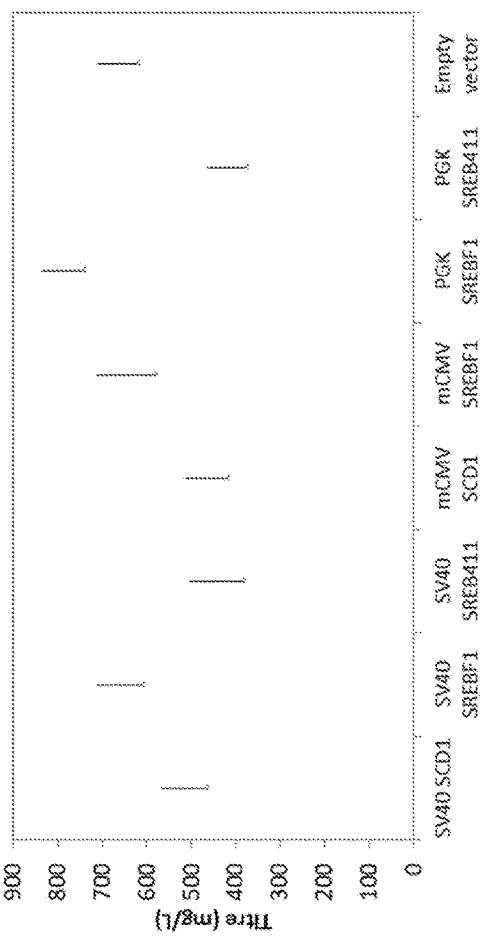
FIGS. 17A-17D are a series of graphs showing 95% confidence interval plots of product concentration for cell cultures expressing an LMM gene and a gene of interest during aFOG. Cells were transfected with the indicated LMM gene under the control of the indicated promoter and a gene encoding Etanercept (FIG. 17A), Cergutuzumab (FIG. 17B), Infliximab (FIG. 17C), or cB72.3 (FIG. 17D). Productivity was measured using an Octet with protein A biosensors. Each data point shows the mean value of the indicated culture's productivity with a confidence interval for p=0.95.
Figure 17B:
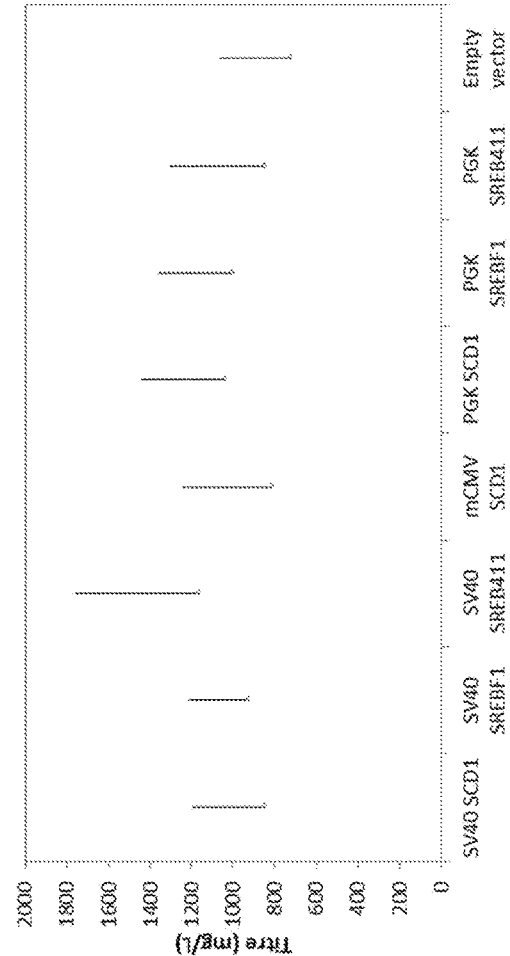
Figure 17C:
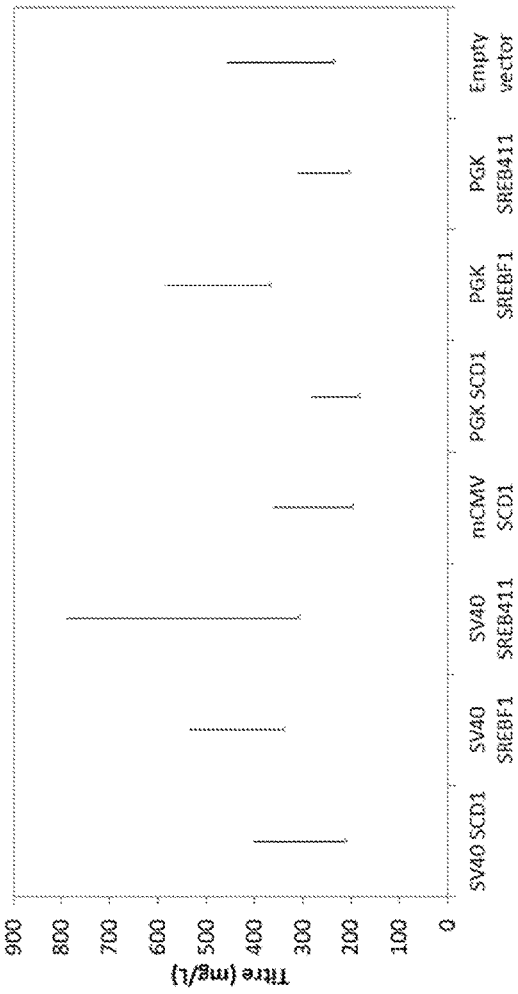
Figure 17D:
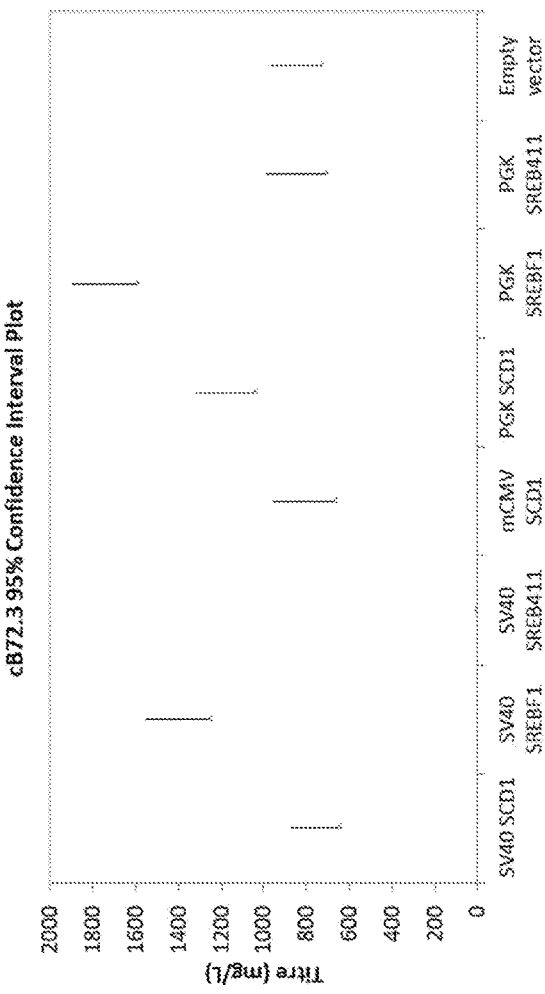

As shown in FIG. 13, the rate of recovery between the recombinant proteins with the exception of Cergutuzumab appeared to be similar. It is possible that this was due to the nature of Cergutuzumab's structure; it has a IL-2 (interleukin-2) molecule attached to the Fc region of the antibodies structure. It is possible that this IL-2 is inhibiting the grown rate of the transfected cells; possibly by its molecular action upon the cells after the Cergutuzumab molecule has been secreted from the cells. It could also be that it is due to the construction of the mAB-IL-2 is limiting the cellular resources, which will slow the recovery rate.

Growth of Transfected Cell Pools in Deep Well Plates

Once cultures had recovered, each well was mixed via pipetting to suspend the cells that were settled on the bottom. Once cells were suspended in culture, 150 μl was transferred in to 150 μl fresh medium (CD CHO, 1% SP4, 50 μM MSX) in a DWP. Deep well plates with cell culture were then incubated at 36.5° C., 5% $CO_2$, 200 rpm, and 90% humidity.

The first DWP subculture was done on either day 4, 5, or 6 dependent upon the growth rate of the cultures. Cells were counted via Celigo; cells were then seeded into 300 μl of CM66+50 μM MSX at a concentration of $0.5 \times 10^6$ viable cells/ml. Daughter DWPs were then incubated at 36.5° C., 5% $CO_2$, 200 rpm, and 90% humidity. Subsequent subcultures were then done a 4 day schedule. Individual cultures/wells were counted using the Celigo system; counts were then averaged across the condition to generate the results in FIG. 14. On the first subculture the medium was changed from the transfection medium to grown medium, and on sub culture 3 the grown medium was changed to production medium to commence the abridged fed batch over grow (aFOG).

FIGS. 14A-14D shows the average viable cell concentration (VCC) of all the recovered transfected cells in deep well plate cultures. The Etanercept+mCMV SREB411 and Etanercept+mCMV SREBF1 (FIG. 14A) recovered at a slower rate than the other conditions. It was decided that for practical reasons to subculture the other conditions one extra time to allow all of the conditions to enter into the aFOG at the same time. This was the reason for an extra subculture recorded for the Etanercept+LMM conditions.

Generally, the average VCC of the cultures across the conditions appeared to stabilize/equalize around the third subculture, with all of the conditions average VCCs grouping together.

Abridged Fed-Batch Overgrow of Transfectant Pools

In order to assess the productivity of the LMM cell pools, the pools were put into a fed batch overgrow to simulate conditions at bioreactor scale. Briefly, upon the third subculture in DWPs, cells were counted using the Celigo and subsequently seeded into 300 μl of CM71 at a concentration of $0.3 \times 10^6$ viable cells/ml. Cells were the incubated at 36.5° C., 5% $CO_2$, 200 rpm, and 90% humidity for 12 days. On day 4 and day 8 the cultures were fed and the cell concentrations counted via Celigo. On day 12, plates were centrifuged at 300 rpm for 10 minutes; 200 μl of the supernatant was collected into a sterile 96 well plate. The remaining cell pellets supernatant were washed with 200 μl PBS and centrifuged at 500 rpm for 10 minutes; as much as possible of the of the PBS wash (~200 μl) was then removed and the cell pellets transferred to −20° C. The collected supernatant was centrifuged at 3000 rpm and 180 μl was then transferred to a new 96 well plate. The collected supernatant was then stored at 4° C. overnight for analysis via an Octet instrument the next day.

Cells were seeded at a lower cell density than routine subculture ($0.3 \times 10^6$ VCC/ml: aFOG; $0.5 \times 10^6$ VCC/ml: Subculture), into production medium, which is very similar to the subculture growth medium, therefore any change in the growth profile due to the change of medium should be minimal (FIGS. 15A-15D). Measurement of the VCC was taken on the same days as feeding and harvest; this allowed for a rough outline of each of the conditions growth profiles during production. This method provides limited growth data and therefore it is possible that the peak of growth for some of the conditions were missed. These missing data will affect the calculation of the IVC (time integral of viable cell concentration in a culture per an hour per a millilitre) and Qp (Specific productivity as pg/cell/h); as all of the cultures and conditions have the same limitation, the data could be considered comparable.

The growth profiles of several of the conditions in the Etanercept and infliximab suggest that the VCC peaks between days 4 and 8. The expression of SREBF1 could delay the growth of the culture post day 4. This is suggested by the growth of the SV40/PGK SREBF1 conditions.

The variance in each time point is most likely due to the fact that the cultures being counted are each a pool of transfected cells; therefore the copy number of both vectors will vary and this will impact cellular growth. Mitigation for the variance was achieved by using 96 individual cultures per a condition and taking an average. With this the expectation is that if the combination of the promoter, LMM gene, and recombinant protein had a significant effect the entire variation of the condition would shift.

Measurement of Product Concentration Post-aFOG

The product concentration was measured using protein A biosensors in an Octet. The Octet is capable of probing individual wells in a 96 well format, although two columns are required for the plate standards and controls; therefore it was possible to measure a maximum of 80 samples per an Octet run. Standards were prepared between 100-5 mg/L, inter-plate controls were diluted to 25 mg/L, and the harvested supernatant of each pool was diluted in CD CHO to fit on to the standard curve produced.

The samples require a minimum concentration for the Octet sensors to quantify the product bound to the protein A biosensors. The number of culture that were quantifiable varied between each condition; the total number of cultures quantified are listed in Table 10. These data show a change in the total quantifiable cultures in some LMM gene conditions across the recombinant protein conditions i.e. the SV40 SREB411 showed a decrease in quantifiable cultures across all of the recombinant protein conditions; were as the SV40 SREBF1 condition shows an equal to or improved number of quantifiable culture.

TABLE 11

Mean productivity (mg/L), Standard deviation of the mean productivity, and the number of cultures quantified (n) using the Octet and protein A biosensors for each condition of promotor + LMM gene + recombinant molecule (cB72.3; Infl: infliximab; Cerg: cergutuzumab; Etan: etanercept)

| | Mean productivity (mg/L) | | | | Standard deviation | | | | n | | | |
|---|---|---|---|---|---|---|---|---|---|---|---|---|
| | | | | | Promoter + LMM | | | | | | | |
| | cB72.3 | Infl | Cerg | Etan | cB72.3 | Infl | Cerg | Etan | cB72.3 | Infl | Cerg | Etan |
| SV40 SCD1 | 753 | 304 | 1020 | 515 | 611 | 376 | 831 | 273 | 75 | 45 | 63 | 75 |
| SV40 SREBF1 | 1399 | 438 | 1070 | 660 | 829 | 456 | 635 | 281 | 79 | 60 | 52 | 77 |
| SV40 SREB411 | n/a | 548 | 1460 | 443 | n/a | 490 | 933 | 277 | n/a | 14 | 29 | 54 |
| mCMV SCD1 | 808 | 277 | 1028 | 464 | 710 | 278 | 750 | 246 | 64 | 33 | 35 | 68 |
| mCMV SREBF1 | n/a | n/a | n/a | 644 | n/a | n/a | n/a | 278 | n/a | n/a | n/a | 48 |
| PGK SCD1 | 1175 | 230 | 1238 | n/a | 731 | 198 | 926 | n/a | 77 | 45 | 59 | n/a |
| PGK SREBF1 | 1743 | 475 | 1181 | 787 | 834 | 453 | 818 | 259 | 79 | 50 | 56 | 80 |
| PGK SREB411 | 843 | 254 | 1077 | 418 | 718 | 174 | 1057 | 234 | 69 | 31 | 58 | 71 |
| Empty vector | 845 | 345 | 890 | 663 | 653 | 434 | 665 | 255 | 78 | 44 | 43 | 78 |

As pools of transfected cells were used, it would be expected that there would be a difference in copy number, of each transfected vector, and inherent productivity per a cell in each pool. A maximum of 80 cell polls were produced per a condition to mitigate this variability and give a more accurate picture of cellular growth and productivity in each condition. The number of quantifiable repeats varied between 14-80 pools.

Calculation of Specific Productivity

Once all the protein A and growth data was gathered it was then possible to calculate the specific productivity for each culture. This was done by calculating pictograms per a cell per an hour (Qp), and the time integral of viable cell concentration in a culture per an hour per a millilitre (IVC) which was calculated by solving the area under the growth curve for each of the cultures. These data can then be expressed in a bubble plot of Qp vs. IVC with each bubble (data point) showing the product titre by the diameter of the bubble. The resulting plots can be seen in FIGS. 16A-16D.

The 95% confidence interval for the mean productivity data shown in Table 11 was analyzed for the mean of each RPLC (recombinant protein+promoter+LMM condition); these data are shown in Table 12 and the resulting intervals are shown in Table 13.

TABLE 12

Statistical analysis of productivity data measured using protein A biosensors to give the 95% confidence interval around the mean productivity.

| | t(n − 1) | | | | t.stat (p = 0.95) | | | | X (t.stat*s)/√t(n − 1) | | | |
|---|---|---|---|---|---|---|---|---|---|---|---|---|
| | | | | | Promoter + LMM | | | | | | | |
| | cB72.3 | Infl | Cerg | Etan | cB72.3 | Infl | Cerg | Etan | cB72.3 | Infl | Cerg | Etan |
| SV40 SCD1 | 74 | 44 | 62 | 74 | 1.666 | 1.68 | 1.67 | 1.666 | 118.224 | 95.2266 | 176.269 | 52.822 |
| SV40 SREBF1 | 78 | 59 | 51 | 76 | 1.665 | 1.671 | 1.675 | 1.665 | 156.266 | 99.2402 | 149.005 | 53.586 |
| SV40 SREB411 | n/a | 13 | 28 | 53 | n/a | 1.771 | 1.701 | 1.674 | n/a | 240.777 | 299.881 | 63.637 |
| mCMV SCD1 | 63 | 32 | 34 | 67 | 1.669 | 1.694 | 1.691 | 1.668 | 149.319 | 83.2512 | 217.483 | 50.101 |
| mCMV SREBF1 | n/a | n/a | n/a | 47 | n/a | n/a | n/a | 1.678 | n/a | n/a | n/a | 67.941 |
| PGK SCD1 | 76 | 44 | 58 | n/a | 1.665 | 1.68 | 1.672 | n/a | 139.631 | 50.0515 | 203.198 | n/a |
| PGK SREBF1 | 78 | 49 | 55 | 79 | 1.665 | 1.677 | 1.673 | 1.664 | 157.159 | 108.584 | 184.573 | 48.569 |
| PGK SREB411 | 68 | 30 | 57 | 70 | 1.668 | 1.697 | 1.672 | 1.667 | 145.284 | 54.0411 | 234.012 | 46.613 |
| Empty vector | 77 | 43 | 42 | 77 | 1.665 | 1.681 | 1.682 | 1.665 | 123.916 | 111.331 | 172.553 | 48.419 |

TABLE 13

The final values calculated for the 95% confidence interval for the mean productivity of each of the recombinant protein + promoter + LMM conditions.

| | Upper | | | | Mean | | | | Lower | | | |
|---|---|---|---|---|---|---|---|---|---|---|---|---|
| | | | | | Promoter + LMM | | | | | | | |
| | cB72.3 | Infl | Cerg | Etan | cB72.3 | Infl | Cerg | Etan | cB72.3 | Infl | Cerg | Etan |
| SV40 SCD1 | 871 | 399 | 1196 | 568 | 753 | 304 | 1020 | 515 | 635 | 209 | 844 | 462 |
| SV40 SREBF1 | 1555 | 537 | 1219 | 714 | 1399 | 438 | 1070 | 660 | 1243 | 339 | 921 | 606 |
| SV40 SREB411 | n/a | 789 | 1760 | 507 | n/a | 548 | 1460 | 443 | n/a | 307 | 1160 | 379 |
| mCMV SCD1 | 957 | 360 | 1245 | 514 | 808 | 277 | 1028 | 464 | 659 | 194 | 811 | 414 |
| mCMV SREBF1 | n/a | n/a | n/a | 712 | n/a | n/a | n/a | 644 | n/a | n/a | n/a | 576 |
| PGK SCD1 | 1315 | 280 | 1441 | n/a | 1175 | 230 | 1238 | n/a | 1035 | 180 | 1035 | n/a |
| PGK SREBF1 | 1900 | 584 | 1366 | 836 | 1743 | 475 | 1181 | 787 | 1586 | 366 | 996 | 738 |
| PGK SREB411 | 988 | 308 | 1311 | 465 | 843 | 254 | 1077 | 418 | 698 | 200 | 843 | 371 |
| Empty vector | 969 | 456 | 1063 | 711 | 845 | 345 | 890 | 663 | 721 | 234 | 717 | 615 |

The data shown in Table 13 was then plotted for each recombinant protein transfection, as shown in FIGS. 17A-17D.

Discussion

By considering both the specific productivity plots and the 95% confidence interval plots (CIPs), it was possible to identify promoter+LMM combinations showing an improvement in the expression of the recombinant proteins under these conditions.

Etanercept

These data showed that on average the PGK+SREBF1 condition does increase the Etanercept titer. This was observed from an average of 80 pools of transfected cells.

Cergutuzumab

The SV40+SREB411 condition showed an increase in titer in the 95% CIP.

Infliximab

The number of measureable cultures for infliximab was generally lower when compared to the Etanercept and cB72.3 conditions.

The PGK/SV40+SREBF1 showed an increase in the titer of Infliximab. In the Infliximab bubble plot, the majority of the data points over Qp=1 appeared to be from those conditions. The PGK+SREBF1 condition had a lower IVC then the SV40+SREBF1 condition, although the PGK+SREBF1 condition had a larger average titer, which can also be seen by the compared number of data points above Qp=1. These two conditions also showed an increase in the number of measureable repeats, suggesting that expression of SREBF1 at these levels does increase cellular survivability when expressing Infliximab.

cB72.3

The cB72.3 recombinant protein is a standard monoclonal antibody and was easier for the cells to express compared to the other recombinant proteins discussed herein.

The 95% CIP, suggested that increasing the expression of SERBF1 may increase the final titer under these conditions. The SV40/PGK+SREBF1 conditions both showed a significant increase in titer. The PGK+SCD1 condition also showed an increase in titer. The cB72.3 bubble plot the SV40+SREBF1 data trended towards a higher Qp and a lower IVC, whereas the reverse was true for the PGK+SREBF1 condition. The SCD1 conditions appeared to group between Qp=0.5-3 and ICV=500-1250. The control condition trended towards a lower Qp with a higher IVC.

Promoter and LMM Combination Selection

The SV40/PGK+SREBF1 combinations have shown an improvement in product titer and either Qp or IVC of the cultures into which they were transfected. The differences between the mouse and CHO sequences for SCD1 can be desirably explored with strong promoters, such as hCMV or mCMV. It is contemplated that these combinations of promoters will improve the product titer.

Example 3: Application of the Pyrroline-5-Carboxylate Synthase Proline Metabolic Selection System for the Generation of Stably LMM Engineered GS-KO CHO Cell Pools Manipulation of lipid metabolism modifiers (LMMs) stearoyl-CoA desaturase-1 (SCD1), sterol regulatory element binding transcription factor 1 (SREBF1), and a truncated SREBF1 isoform, SREB411, comprising the portion of SREBF1 that migrates to the nucleus and lacking the regulatory domains of SREBF1, have been shown to improve CHOK1SV GS-KO host production and product quality of complex proteins and standard mAbs by the examples above. The P5CS proline metabolic selection was therefore utilized to generate stably expressing LMM modified GS-KO CHO cell pools over-expressing either SCD1 or SREBF1 under the control of different promoters.

The GS-KO CHO host was transfected, by electroporation, with either PGK SCD1 (CHO) or PGK SREBF1, using the P5CS selection system or PGK SCD1 (Mouse) or SV40 SREBF1 in Lonza proprietary chemically defined, protein free, medium lacking proline. The transfected cells were then plated into three 96 well plates (100 µl culture per a well) and incubated at 36.5° C., 10% $CO_2$. On day 7 post transfection, 150 µl per well/culture was removed from each plate of transfected cultures and fresh medium lacking proline was added to each well/culture. Cultures were then monitored for outgrowth and recovery post transfection. Cellular recovery post transfection was observed from around 14 days post transfection. Once >75% of cultures were considered to be >75-80% confluent, the cultures in the plate were considered to be recovered and transferred to 96 deep well plates.

After sub-culture in 96 deep well plates, cell pellet samples were collected and protein lysates generated and analyzed by Western blot for the expression of the target LMM (SCD1 or SREBF1), with P5CS expression and β-actin acting as controls. From the resulting analysis, cell pools in each well were classified as expressing 'high', 'medium' or 'low' amounts of the target LMM relative to each other and a control. The 'highest' 10 expressing cell wells were then combined to generate a 'high' expressing pool of cells, 10-15 wells spread across the 'medium' expressers pooled to generate a 'medium' expressing LMM pool and 10-15 wells spread across the 'low' expressers combined to generate a 'low' expressing LMM pool. In the case of the medium and low pools, wells were taken from each of the three plates. These LMM engineered cell pools were then expanded into shake flasks and grown in Lonza proprietary medium without proline. Cell lysates were then collected to assess LMM and P5CS expression in the engineered cell pools.

Figure 18:
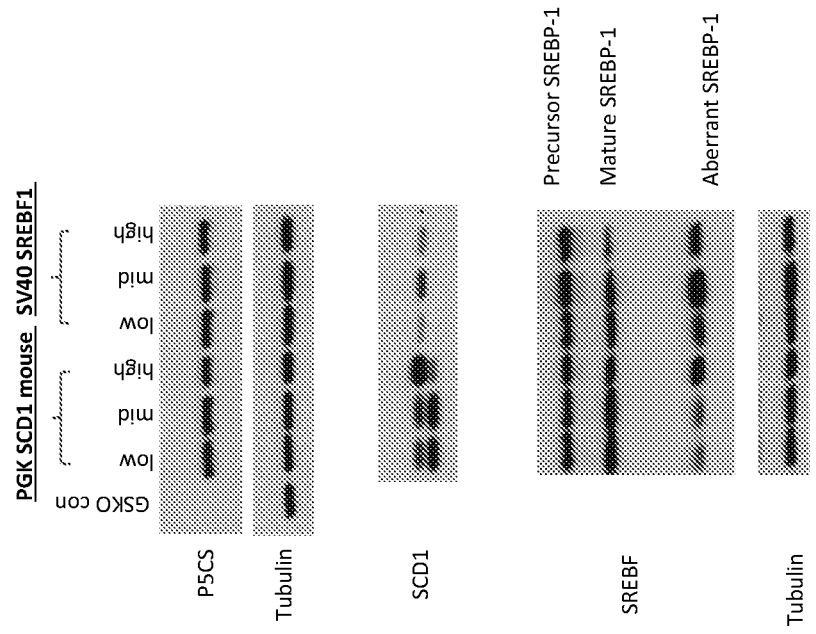
FIG. 18 is a series of western blots of cell lysates from SCD1 or SREBF1 engineered CHO cells isolated using a P5CS metabolic selection system and cells grown in the absence of proline in the media.
Figure 18:

FIG. 18 shows Western blot analysis of the cell pools generated, confirming no or very low P5CS expression in the host control GS-KO CHO cell line and similar amounts of P5CS expression in the different LMM pools. This confirms that the P5CS selection system results in the isolation of cells expressing the P5CS enzyme. Tubulin was used as a loading control. SCD1 amounts were shown to be elevated in the mid and high PGK SCD1 CHO pools compared to the low whilst the precursor SREBF1 molecule engineered in the cells was elevated in the mid and high PGK SREBF1 pools compared to the low pools as shown in FIG. 18. A similar observation was made for the PGK SCD1 mouse and SV40 SREBF1 engineered cells. Thus, FIG. 18 shows that the proline metabolic selection system based on P5CS coupled to LMM expression resulted in the successful isolation of P5CS expressing cells with increased LMM amounts growing in medium that lacked proline.

The different LMM expressing pools were then transfected with a vector for a recombinant biotherapeutic (Etanercept or Infliximab) and GS, transfected as described in Example 2 above, and then recovered in proline and glutamine free medium in 96 well plates. Cellular recovery post transfection was observed from around 14 days post transfection. Once >75% of cultures were considered to be >75-80% confluent, the cultures in the plate were considered to be recovered and transferred to deep well plates. The cells were subsequently subcultured and the titre assessed using an Octet instrument and then the highest 10 wells from each LMM engineered transfected pool combined and grown in shake flasks. The productivity and growth characteristics of these were then assessed in a miniature bioreactor under fed-batch culture conditions.

FIGS. 19A-19D shows a plot of Qp against the integral viable cell concentration (IVC) (IVC, time integral of viable cell concentration in a culture per an hour per a millilitre and Qp, Specific productivity as pg/cell/h) for each LMM engineered pool subsequently transfected with a recombinant molecule and assessed for productivity and growth in a Ambr™ 15 miniature bioreactor under fed-batch conditions on day 9 of culture in duplicate cultures.

Figure 19A:
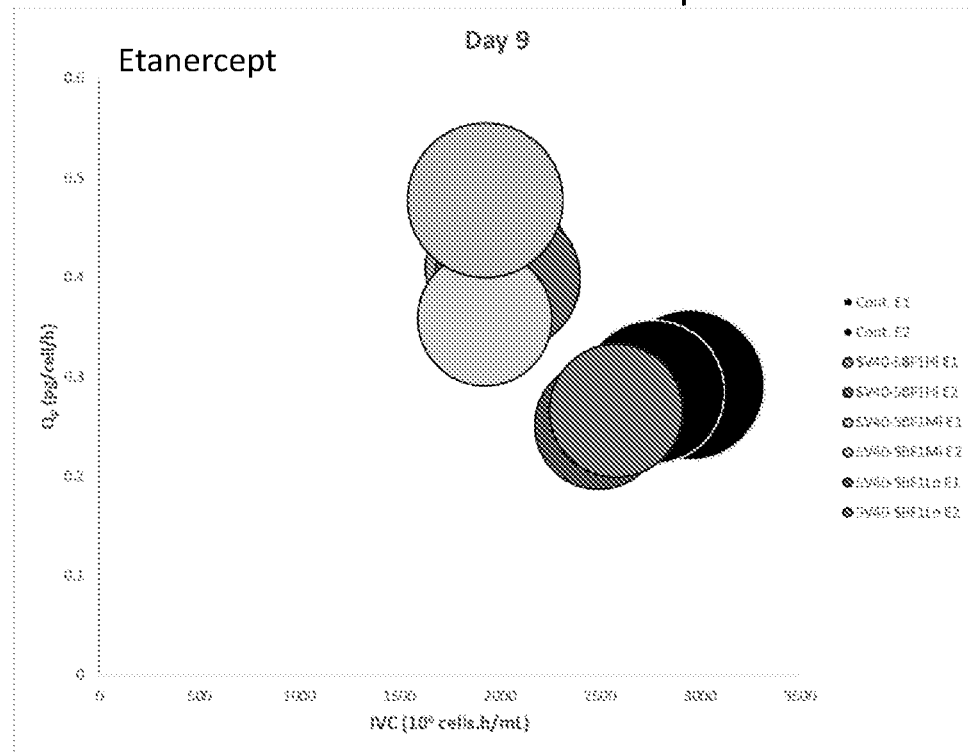
FIGS. 19A-D shows a series of graphs of the cell specific productivities (Qp) against the IVC of SREBF1 or SCD1 engineered CHO cell pools with different amounts of expression of these lipid metabolism modifying (LMM) genes subsequently transfected with the genes for either Etanercept or Infliximab alongside the selection marker glutamine synthetase and the secretory expression of the recombinant protein molecules assessed in miniature bioreactors under fed-batch conditions in the absence of glutamine or proline.
Figure 19A:
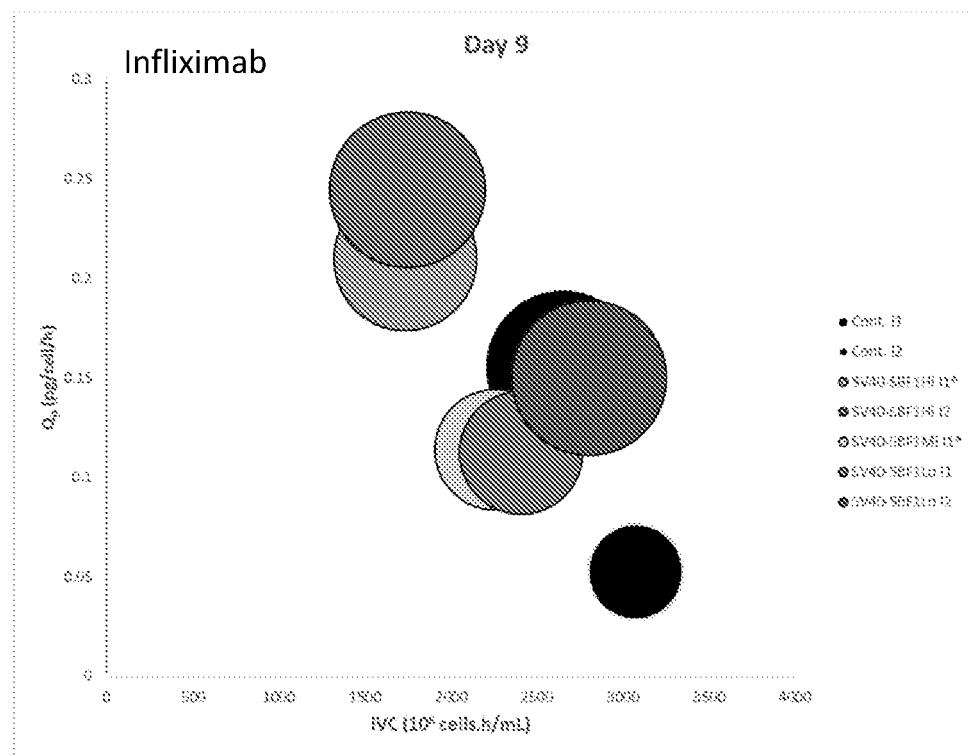
Figure 19B:
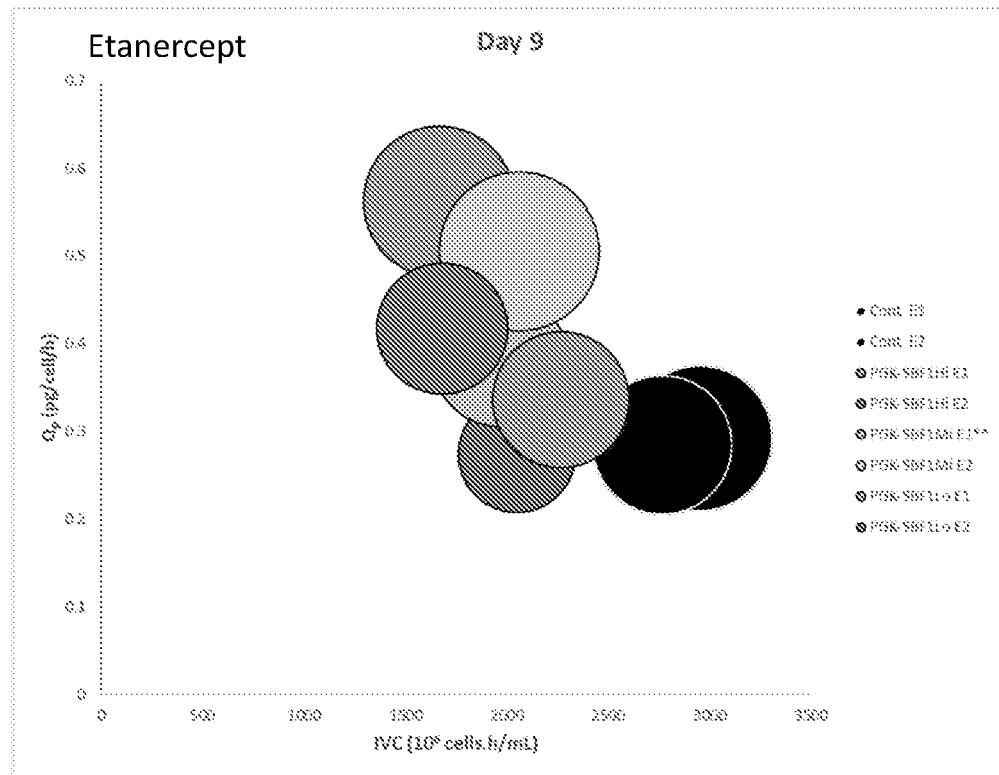
Figure 19B:
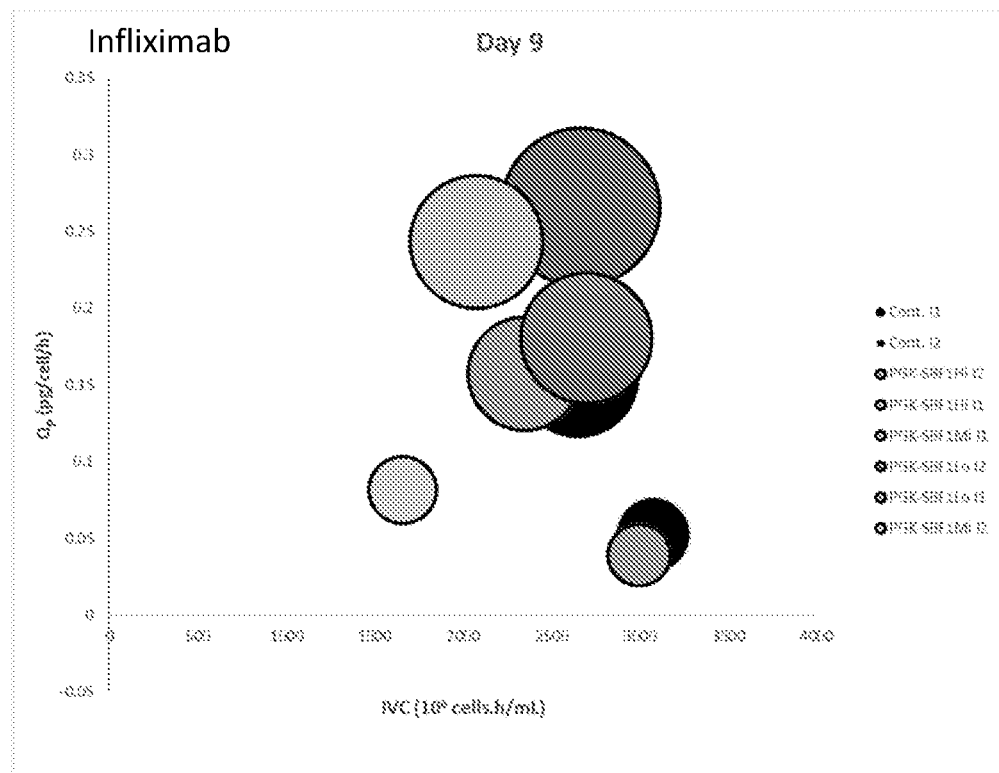
Figure 19C:
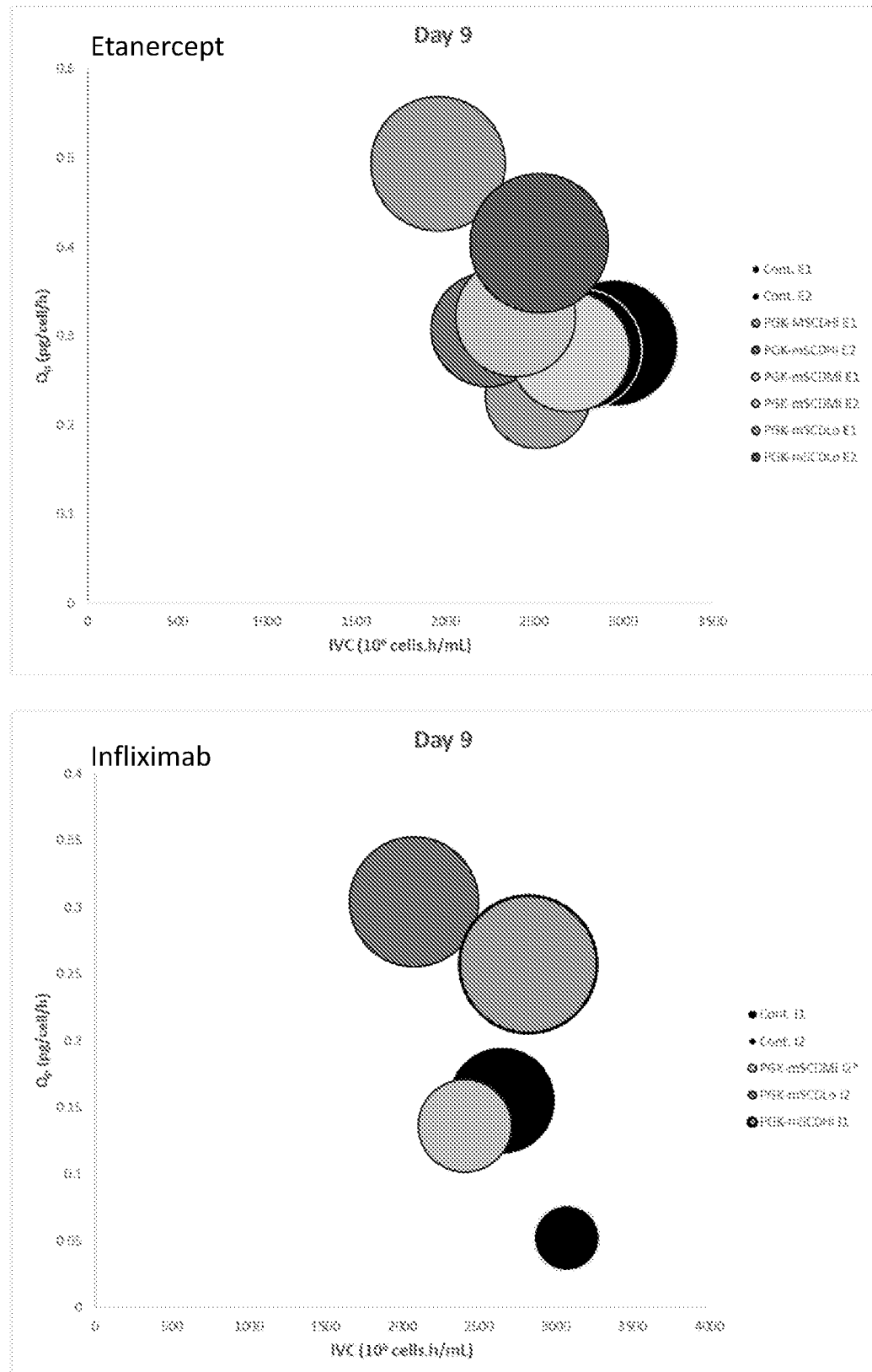
Figure 19D:
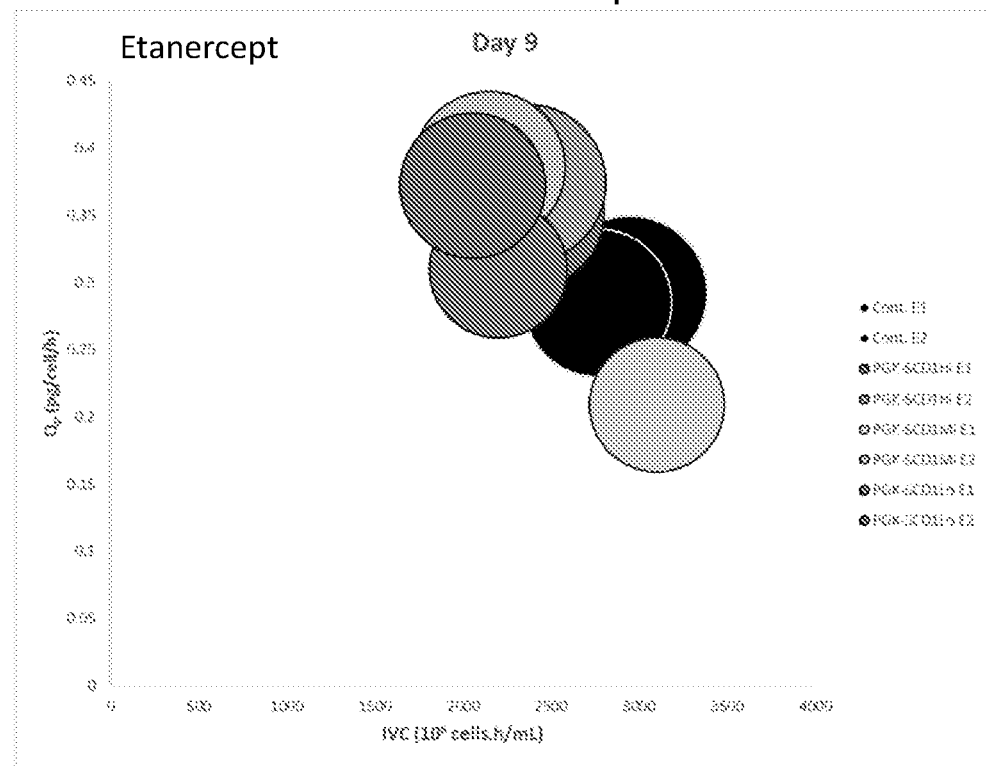
Figure 19D:
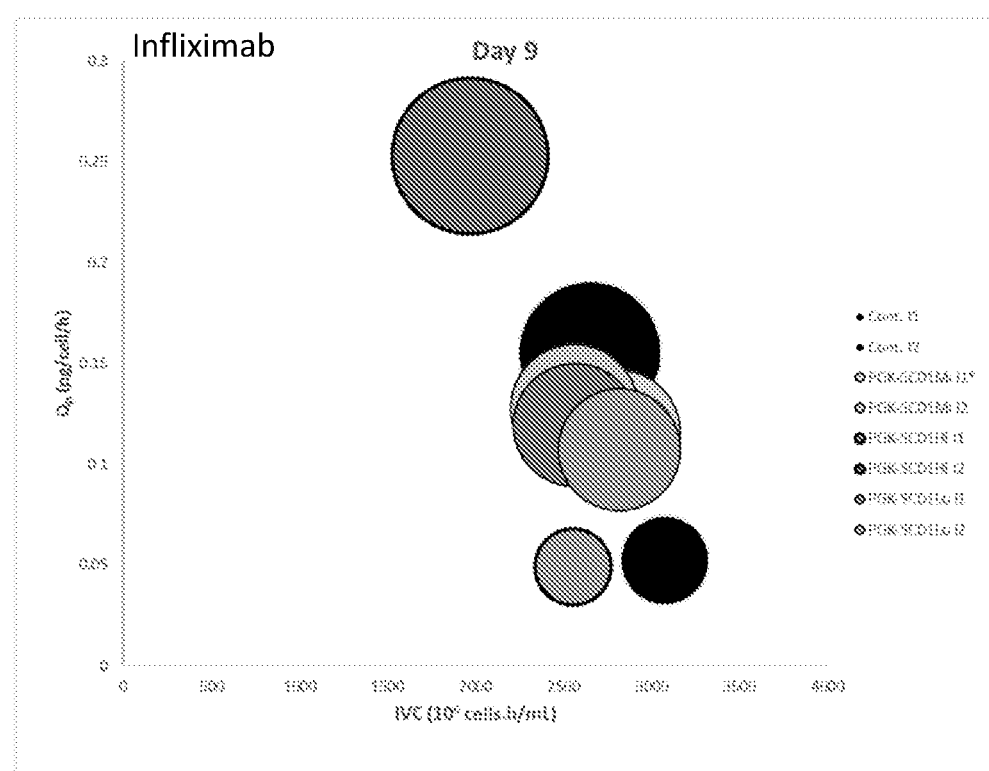

The legend of FIG. 19A, top, reads (top to bottom) Cont. E1, Cont. E2, SV40-SBF1Hi E1, SV40-SBF1HiE2, SV40-SBF1MiE1, SV40-SBF1MiE2, SV40-SBF1LoE1, SV40-SBF1LoE2. The y-axis begins, at bottom, with 0 and proceeds 0.1, 0.2, 0.3, 0.4, 0.5 and 0.6, labeled as $Q_p$ (pg/cell/h). The x-axis begins, at left, with 0 and proceeds 500, 1000, 1500, 2000, 2500, 3000, and 3500, labeled as IVC ($10^6$ cells·h/ml). The legend of FIG. 19A, bottom, reads (top to bottom) Cont. I1, Cont. I2, SV40-SBF1Hi I1*, SV40-SBF1HiI2, SV40-SBF1MiI1*, SV40-SBF1LoI1, SV40-SBF1LoI2. The y-axis begins, at bottom, with 0 and proceeds 0.05, 0.1, 0.15, 0.2, 0.25, and 0.3, labeled as $Q_p$ (pg/cell/h). The x-axis begins, at left, with 0 and proceeds 500, 1000, 1500, 2000, 2500, 3000, 3500, and 4000 labeled as IVC ($10^6$ cells·h/ml). The legend of FIG. 19B, top, reads (top to bottom) Cont. E1, Cont. E2, PGK-SBF1Hi E1, PGK-SBF1HiE2, PGK-SBF1MiE1**, PGK-SBF1MiE2, PGK-SBF1LoE1, PGK-SBF1LoE2. The y-axis begins, at bottom, with 0 and proceeds 0.1, 0.2, 0.3, 0.4, 0.5, 0.6, and 0.7 labeled as $Q_p$ (pg/cell/h). The x-axis begins, at left, with 0 and proceeds 500, 1000, 1500, 2000, 2500, 3000, and 3500, labeled as IVC ($10^6$ cells·h/ml). The legend of FIG. 19B, bottom, reads (top to bottom) Cont. I1, Cont. I2, PGK-SBF1Hi I2, PGK-SBF1HiI1, PGK-SBF1MiI1, PGK-SBF1LoI2, PGK-SBF1LoI1, PGK-SBF1MiI2. The y-axis begins, at bottom, with −0.05 and proceeds 0, 0.05, 0.1, 0.15, 0.2, 0.25, 0.3, and 0.35 labeled as $Q_p$ (pg/cell/h). The x-axis begins, at left, with 0 and proceeds 500, 1000, 1500, 2000, 2500, 3000, 3500, and 4000 labeled as IVC ($10^6$ cells·h/ml). The legend of FIG. 19C, top, reads (top to bottom) Cont. E1, Cont. E2, PGK-MSCDHi E1, PGK-mSCDHiE2, PGK-mSCDMiE1, PGK-mSCDMiE2, PGK-mSCDLoE1, PGK-mSCDLoE2. The y-axis begins, at bottom, with 0 and proceeds 0.1, 0.2, 0.3, 0.4, 0.5, and 0.6, and labeled as $Q_p$ (pg/cell/h). The x-axis begins, at left, with 0 and proceeds 500, 1000, 1500, 2000, 2500, 3000, and 3500, labeled as IVC ($10^6$ cells·h/ml). The legend of FIG. 19C, bottom, reads (top to bottom) Cont. I1, Cont. I2, PGK-mSCDMi I2*, PGK-mSCDLoI2, PGK-mSCDHiI1. The y-axis begins, at bottom, with 0 and proceeds 0.05, 0.1, 0.15, 0.2, 0.25, 0.3, 0.35, and 0.4 labeled as $Q_p$ (pg/cell/h). The x-axis begins, at left, with 0 and proceeds 500, 1000, 1500, 2000, 2500, 3000, 3500, and 4000 labeled as IVC ($10^6$ cells·h/ml). The legend of FIG. 19D, top, reads (top to bottom) Cont. E1, Cont. E2, PGK-SCDHi E1, PGK-SCDHiE2, PGK-SCDMiE1, PGK-SCDMiE2, PGK-SCDLoE1, PGK-SCDLoE2. The y-axis begins, at bottom, with 0 and proceeds 0.05, 0.1, 0.15, 0.2, 0.25, 0.3, 0.35, 0.4, and 0.45 labeled as $Q_p$ (pg/cell/h). The x-axis begins, at left, with 0 and proceeds 500, 1000, 1500, 2000, 2500, 3000, 3500, and 4000 labeled as IVC ($10^6$ cells·h/ml). The legend of FIG. 19D, bottom, reads (top to bottom) Cont. I1, Cont. I2, PGK-SCDMi I1*, PGK-SCDMi I2, PGK-SCDHiI1, PGK-SCDHiI2, PGK-SCDLoI1, PGK-SCDLoI2. The y-axis begins, at bottom, with 0 and proceeds 0.05, 0.1, 0.15, 0.2, 0.25, and 0.3 labeled as $Q_p$ (pg/cell/h). The x-axis begins, at left, with 0 and proceeds 500, 1000, 1500, 2000, 2500, 3000, 3500, and 4000 labeled as IVC ($10^6$ cells·h/ml).

The IVC of the control cells (Black circles, FIG. 19, non-LMM engineered) was generally amongst the highest but in each case there was a number of LMM pools with higher Qp than the control and similar IVCs to the control when expressing these model difficult to express proteins ("*" denotes vessel was harvested on day 12 and "**" denotes harvested on day 14). This is consistent with the idea that LMM engineered cells, produced and cultured using P5CS selection methods, can have increased Qp when producing difficult to express proteins and comparable IVC to non-LMM engineered cells under similar conditions.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

We claim:

1. A method of identifying, selecting or culturing a mammalian cell comprising a subject nucleic acid sequence, the method comprising:
    a) providing a cell comprising a heterologous nucleic acid comprising:
        (i) the subject nucleic acid sequence; and
        (ii) a nucleic acid sequence encoding a pyroline-5-carboxylate synthase (P5CS) molecule; and
    b) culturing the cell comprising the heterologous nucleic acid sequence in the presence of media having an insufficient level of proline to support growth of a cell not having elevated P5CS enzymatic activity that is the same cell type as in step a), under conditions sufficient to allow for growth of a cell comprising the heterologous nucleic acid sequence, wherein the media further comprises an inhibitor of enzymatic activity of the P5CS molecule and wherein the inhibitor is a proline analog, thereby identifying, selecting or culturing, a cell comprising the heterologous nucleic acid sequence.

2. The method of claim 1, wherein the heterologous nucleic acid is a vector.

3. The method of claim 1, wherein the inhibitor is L-azetidine-2-carboxylic acid, 3,4-dehydro-L-proline, or L-4-thiazolidinecarboxylic acid.

4. The method of claim 1, comprising selecting a cell comprising the heterologous nucleic acid sequence.

5. The method of claim 1, wherein the heterologous nucleic acid is integrated into the genome of the cell.

6. The method of claim 1, further comprising selecting a cell that exhibits growth.

7. The method of claim 1, wherein the mammalian cell is a CHO cell.

8. The method of claim 1, wherein an endogenous copy of a sequence that encodes the P5CS molecule has been inactivated.

9. The method of claim 1, wherein the subject nucleic acid sequence encodes a heterologous polypeptide molecule.

10. The method of claim 1, comprising recovering a polypeptide product encoded by the subject nucleic acid sequence from the cell or media.

* * * * *

UNITED STATES PATENT AND TRADEMARK OFFICE
CERTIFICATE OF CORRECTION

| | | |
|---|---|---|
| PATENT NO. | : 12,077,786 B2 | Page 1 of 1 |
| APPLICATION NO. | : 16/966768 | |
| DATED | : September 3, 2024 | |
| INVENTOR(S) | : Robert Young et al. | |

It is certified that error appears in the above-identified patent and that said Letters Patent is hereby corrected as shown below:

On the Title Page

Item (72) The listed inventor "Joanne ROBOOL" should read --Joanne ROOBOL--.

Signed and Sealed this
Sixth Day of January, 2026

John A. Squires
*Director of the United States Patent and Trademark Office*